US007273885B2

(12) United States Patent
Pitlik et al.

(10) Patent No.: US 7,273,885 B2
(45) Date of Patent: Sep. 25, 2007

(54) INHIBITORS OF SERINE PROTEASES, PARTICULARLY HCV NS3-NS4A PROTEASE

(75) Inventors: Janos Pitlik, Westborough, MA (US); Kevin M. Cottrell, Cambridge, MA (US); Luc J. Farmer, Foxboro, MA (US); Robert B. Perni, Marlborough, MA (US); Lawrence F. Courtney, Medway, MA (US); John H. van Drie, Andover, MA (US); Mark A. Murcko, Holliston, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 232 days.

(21) Appl. No.: 10/412,600

(22) Filed: Apr. 11, 2003

(65) Prior Publication Data

US 2004/0018986 A1 Jan. 29, 2004

Related U.S. Application Data

(60) Provisional application No. 60/371,846, filed on Apr. 11, 2002.

(51) Int. Cl.
*A61K 31/403* (2006.01)
*A61K 31/435* (2006.01)
*C07D 209/02* (2006.01)
*C07D 221/00* (2006.01)

(52) U.S. Cl. .................... 514/414; 546/79; 546/85; 546/112; 548/134; 548/146; 548/182; 548/225; 548/250; 548/262.2; 548/452; 548/465; 514/292; 514/299

(58) Field of Classification Search ................ 548/452, 548/465, 134, 182, 225, 262.2; 514/414, 514/292, 299; 546/79, 85, 112
See application file for complete search history.

(56) References Cited

U.S. PATENT DOCUMENTS

| | | | |
|---|---|---|---|
| 5,866,684 | A | 2/1999 | Attwood et al. |
| 6,018,020 | A | 1/2000 | Attwood et al. |
| 6,211,338 | B1 * | 4/2001 | Malcolm et al. ............ 530/350 |
| 6,800,434 | B2 * | 10/2004 | Saksena et al. ................ 435/5 |
| 2002/0016294 | A1 | 2/2002 | Venkatraman et al. |
| 2002/0016442 | A1 | 2/2002 | Llinas-brunet et al. |
| 2002/0177725 | A1 | 11/2002 | Priestly et al. |
| 2003/0008828 | A1 | 1/2003 | Priestly et al. |

FOREIGN PATENT DOCUMENTS

| | | |
|---|---|---|
| WO | WO97/43310 | 11/1997 |
| WO | WO98/17679 | 4/1998 |
| WO | WO98/22496 | 5/1998 |
| WO | WO98/46630 | 10/1998 |
| WO | WO99/07733 | 2/1999 |
| WO | WO99/07734 | 2/1999 |
| WO | 1999/37666 A1 | 7/1999 |
| WO | WO99/38888 | 8/1999 |
| WO | WO99/50230 | 10/1999 |
| WO | WO99/64442 | 12/1999 |
| WO | WO 00/09543 | 2/2000 |
| WO | WO 00/09558 | 2/2000 |
| WO | WO 00/31129 | 6/2000 |
| WO | WO 00/59929 | 10/2000 |
| WO | 2002/08244 A1 | 1/2001 |
| WO | WO 01/07407 | 2/2001 |
| WO | 2001/16300 A2 | 3/2001 |
| WO | 2001/40262 A1 | 6/2001 |
| WO | WO 01/64678 | 9/2001 |
| WO | WO 01/74768 | 10/2001 |
| WO | WO 01/77113 | 10/2001 |
| WO | WO 01/81325 | 11/2001 |
| WO | WO 02/08187 | 1/2002 |
| WO | WO 02/08198 | 1/2002 |
| WO | WO 02/08244 | 1/2002 |
| WO | WO 02/08251 | 1/2002 |
| WO | WO 02/08256 | 1/2002 |
| WO | WO 02/18369 | 3/2002 |
| WO | WO 02/48116 | 6/2002 |
| WO | WO 02/48157 | 6/2002 |
| WO | WO 02/060926 | 8/2002 |
| WO | WO 02/079234 | 10/2002 |
| WO | WO 03/006490 | 1/2003 |

OTHER PUBLICATIONS

Han, Wei et al., "α-Ketoamides, α-Ketoesters and α-Diketones as HCV NS3 Protease Inhibitors," Bioorganic & Medicinal Chemistry Letters, 2000, vol. 10, No. 8, pp. 711-713.

* cited by examiner

*Primary Examiner*—Golam M. M. Shameem
(74) *Attorney, Agent, or Firm*—Susan C. Kelly; Lisa A. Dixon

(57) ABSTRACT

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention. The invention further relates to processes for preparing these compounds.

29 Claims, No Drawings

INHIBITORS OF SERINE PROTEASES, PARTICULARLY HCV NS3-NS4A PROTEASE

CROSS-REFERENCE TO RELATED APPLICATIONS

This application claims the benefit of U.S. Provisional Application No. 60/371,846, filed Apr. 11, 2002, which is hereby incorporated by reference.

TECHNICAL FIELD OF THE INVENTION

The present invention relates to compounds that inhibit serine protease activity, particularly the activity of hepatitis C virus NS3–NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology*, 31., (Suppl. 1), pp. 17–24 (1999)]. Nearly four million individuals may be infected in the United States alone [M. J. Alter et al., "The Epidemiology of Viral Hepatitis in the United States, *Gastroenterol. Clin. North Am.*, 23, pp. 437–455 (1994); M. J. Alter "Hepatitis C Virus Infection in the United States," *J. Hepatology*, 31., (Suppl. 1), pp. 88–91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201–204 (1994); D. Lavanchy, "Global Surveillance and Control of Hepatitis C," *J. Viral Hepatitis*, 6, pp. 35–47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211–220 (1994); I. Saito et. al., "Hepatitis C Virus Infection is Associated with the Development of Hepatocellular Carcinoma," *Proc. Natl. Acad. Sci. USA*, 87, pp. 6547–6549 (1990)]. Unfortunately, there are no broadly effective treatments for the debilitating progression of chronic HCV.

The HCV genome encodes a polyprotein of 3010–3033 amino acids [Q. L. Choo, et. al., "Genetic Organization and Diversity of the Hepatitis C Virus." *Proc. Natl. Acad. Sci. USA*, 88, pp. 2451–2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524–9528 (1990); A. Takamizawa et. al., "Structure and Organization of the Hepatitis C Virus Genome Isolated From Human Carriers," *J. Virol.*, 65, pp. 1105–1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.*, 67, pp. 3835–3844 (1993); A. Grakoui et. al., "Characterization of the Hepatitis C Virus-Encoded Serine Proteinase: Determination of Proteinase-Dependent Polyprotein Cleavage Sites," *J. Virol.*, 67, pp. 2832–2843 (1993); A. Grakoui et. al., "Expression and Identification of Hepatitis C Virus Polyprotein Cleavage Products," *J. Virol.*, 67, pp. 1385–1395 (1993); L. Tomei et. al., "NS3 is a serine protease required for processing of hepatitis C virus polyprotein", *J. Virol.*, 67, pp. 4017–4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898–8902 (1990)]. The first 181 amino acids of NS3 (residues 1027–1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147–8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery.

Several potential HCV protease inhibitors have been described in the prior art [PCT publication Nos. WO 02/18369, WO 02/08244, WO 00/09558, WO 00/09543, WO 99/64442, WO 99/07733, WO 99/07734, WO 99/50230, WO 98/46630, WO 98/17679 and WO 97/43310, U.S. Pat. No. 5,990,276, M. Llinas-Brunet et al., *Bioorg. Med. Chem. Lett.*, 8, pp. 1713–18 (1998); W. Han et al., *Bioorg. Med. Chem. Lett.*, 10, 711–13 (2000); R. Dunsdon et al., *Bioorg. Med. Chem. Lett.*, 10, pp. 1571–79 (2000); M. Llinas-Brunet et al., *Bioorg. Med. Chem. Lett.*, 10, pp. 2267–70 (2000); and S. LaPlante et al., *Bioorg. Med. Chem. Lett.*, 10, pp. 2271–74 (2000)].

Furthermore, the current understanding of HCV has not led to any other satisfactory anti-HCV agents or treatments. The only established therapy for HCV disease is interferon treatment. However, interferons have significant side effects [M. A. Wlaker et al., "Hepatitis C Virus: An Overview of Current Approaches and Progress," *DDT*, 4, pp. 518–29 (1999); D. Moradpour et al., "Current and Evolving Therapies for Hepatitis C," *Eur. J. Gastroenterol. Hepatol.*, 11, pp. 1199–1202 (1999); H. L. A. Janssen et al. "Suicide Associated with Alfa-Interferon Therapy for Chronic Viral Hepatitis," *J. Hepatol.*, 21, pp. 241–243 (1994); P. F. Renault et al., "Side Effects of Alpha Interferon," *Seminars in Liver Disease*, 9, pp. 273–277. (1989)] and induce long term remission in only a fraction (~25%) of cases [O. Weiland, "Interferon Therapy in Chronic Hepatitis C Virus Infection", FEMS Microbiol. Rev., 14, pp. 279–288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention provides a compound of formulae (IA):

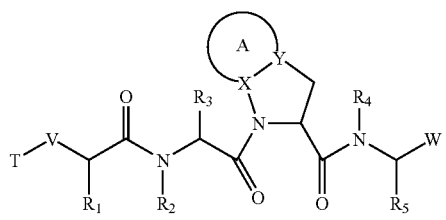

(IA)

wherein:
A, together with X and Y, is:
a 3- to 6-membered aromatic or non-aromatic ring having up to 3 heteroatoms independently selected from N, NH, O, SO, or $SO_2$;
wherein said ring is optionally fused to a (C6–C10)aryl, (C5–C10)heteroaryl, (C3–C10)cycloalkyl or (C3–C10)heterocyclyl;
wherein A has up to 3 substituents selected independently from J;
J is halogen, —OR', —$NO_2$, —$CF_3$, —$OCF_3$, —R', oxo, —OR', —O-benzyl, —O-phenyl, 1,2-methylenedioxy, —N(R')$_2$, —SR', —SOR', —$SO_2$R', —C(O)R', —COOR' or —CON(R')$_2$, wherein R' is independently selected from:
hydrogen,
(C1–C12)-aliphatic,
(C3–C10)-cycloalkyl or -cycloalkenyl,
[(C3–C10)-cycloalkyl or -cycloalkenyl]-(C1–C12)-aliphatic,
(C6–C10)-aryl,
(C6–C10)-aryl-(C1–C12)aliphatic,
(C3–C10)-heterocyclyl,
(C6–C10)-heterocyclyl-(C1–C12)aliphatic,
(C5–C10)-heteroaryl, or
(C5–C10)-heteroaryl-(C1–C12)-aliphatic;
$R_1$ and $R_3$ are independently:
(C1–C12)-aliphatic,
(C3–C10)-cycloalkyl or -cycloalkenyl,
[(C3–C10)-cycloalkyl or -cycloalkenyl]-(C1–C12)-aliphatic,
(C6–C10)-aryl,
(C6–C10)-aryl-(C1–C12)aliphatic,
(C3–C10)-heterocyclyl,
(C6–C10)-heterocyclyl-(C1–C12)aliphatic,
(C5–C10)-heteroaryl, or
(C5–C10)-heteroaryl-(C1–C12)-aliphatic,
wherein each of $R_1$ and $R_3$ is independently and optionally substituted with up to 3 substituents independently selected from J;

wherein up to 3 aliphatic carbon atoms in $R_1$ and $R_3$ may be replaced by a heteroatom selected from O, NH, S, SO, or $SO_2$ in a chemically stable arrangement;
$R_2$ and $R_4$ are independently
hydrogen,
(C1–C12)-aliphatic,
(C3–C10)-cycloalkyl-(C1–C12)-aliphatic, or
(C6–C10)aryl-(C1–C12)-aliphatic,
wherein each of $R_2$ and $R_4$ is independently and optionally substituted with up to 3 substituents independently selected from J;
wherein up to two aliphatic carbon atoms in $R_2$ and $R_4$ may be replaced by a heteroatom selected from O, NH, S, SO, or $SO_2$;
$R_5$ is ($C_1$–$C_{12}$)-aliphatic, wherein any hydrogen is optionally replaced with halogen, and wherein any hydrogen or halogen atom bound to any terminal carbon atom of $R_5$ is optionally substituted with sulfhydryl or hydroxy;
W is selected from:

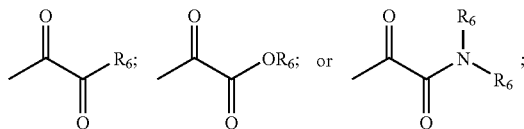

wherein each $R_6$ is independently:
hydrogen,
(C1–C12)-aliphatic,
(C6–C10)-aryl,
(C6–C10)-aryl-(C1–C12)aliphatic,
(C3–C10)-cycloalkyl or -cycloalkenyl,
[(C3–C10)-cycloalkyl or -cycloalkenyl]-(C1–C12)-aliphatic,
(C3–C10)-heterocyclyl,
(C3–C10)-heterocyclyl-(C1–C12)-aliphatic,
(C5–C10)heteroaryl, or
(C5–C10)heteroaryl-(C1–C12)-aliphatic, or
two $R_6$ groups, which are bound to the same nitrogen atom, form together with that nitrogen atom, a (C3–C10)-heterocyclic ring;
wherein $R_6$ is optionally substituted with up to 3 J substituents;
V is —C(O)N($R_8$)—, —S(O)N($R_8$)—, or —S(O)$_2$N($R_8$)—;
wherein $R_8$ is hydrogen or (C1–C12)-aliphatic;
T is selected from:
(C6–C10)-aryl,
(C6–C10)-aryl-(C1–C12)aliphatic,
(C3–C10)-cycloalkyl or -cycloalkenyl,
[(C3–C10)-cycloalkyl or -cycloalkenyl]-(C1–C12)-aliphatic,
(C3–C10)-heterocyclyl,
(C3–C10)-heterocyclyl-(C1–C12)-aliphatic,
(C5–C10)heteroaryl, or
(C5–C10)heteroaryl-(C1–C12)-aliphatic; or
T is selected from:

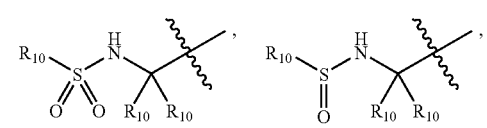

-continued

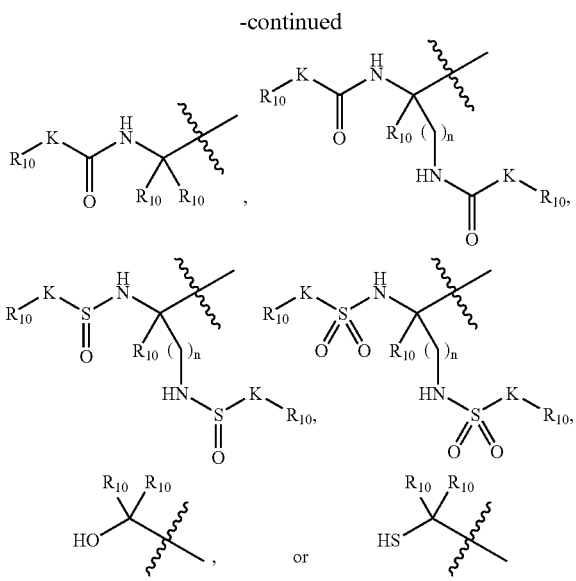

wherein:
R₁₀ is:
hydrogen,
(C1–C12)-aliphatic,
(C6–C10)-aryl,
(C6–C10)-aryl-(C1–C12)aliphatic,
(C3–C10)-cycloalkyl or -cycloalkenyl,
[(C3–C10)-cycloalkyl or -cycloalkenyl]-(C1–C12)-aliphatic,
(C3–C10)-heterocyclyl,
(C3–C10)-heterocyclyl-(C1–C12)-aliphatic,
(C5–C10)-heteroaryl, or
(C5–C10)-heteroaryl-(C1–C12)-aliphatic,
wherein each T is optionally substituted with up to 3 J substituents;
K is a bond, (C1–C12)-aliphatic, —O—, —S—, —NR₉—, —C(O)—, or —C(O)—NR₉—, wherein R₉ is hydrogen or (C1–C12)-aliphatic; and
n is 1–3.

The invention also provides compounds of formula (IB):

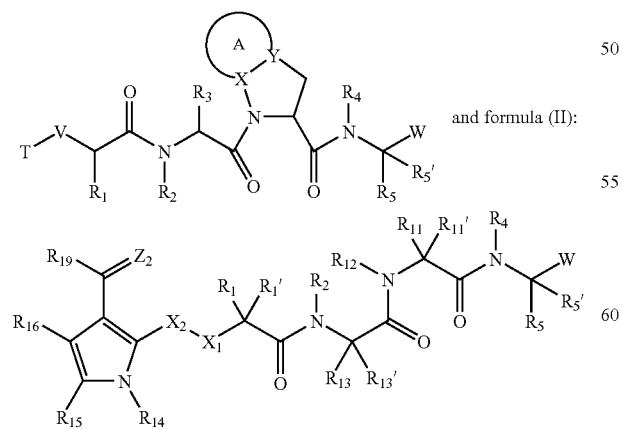

and formula (II):

wherein the variables are as defined herein.

The invention also relates to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

The invention also relates to processes for preparing the compounds of formulae (IA), (IB), and (II).

DETAILED DESCRIPTION OF THE INVENTION

The present invention provides a compound of formula (I):

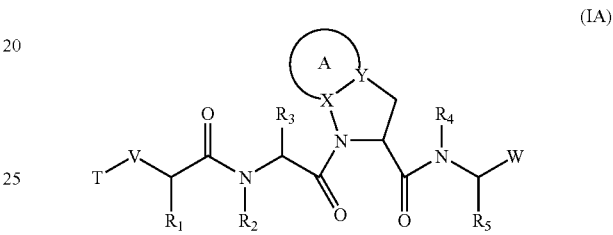

(IA)

wherein:
A, together with X and Y, is:
a 3- to 6-membered aromatic or non-aromatic ring having up to 3 heteroatoms independently selected from N, NH, O, SO, or SO₂;
wherein said ring is optionally fused to a (C6–C10)aryl, (C5–C10)heteroaryl, (C3–C10)cycloalkyl or (C3–C10)heterocyclyl;
wherein A has up to 3 substituents selected independently from J;
J is halogen, —OR', —NO₂, —CF₃, —OCF₃, —R', oxo, —OR', —O-benzyl, —O-phenyl, 1,2-methylenedioxy, —N(R')₂, —SR', —SOR', —SO₂R', —C(O)R', —COOR' or —CON(R')₂, wherein R' is independently selected from:
hydrogen,
(C1–C12)-aliphatic,
(C3–C10)-cycloalkyl or -cycloalkenyl,
[(C3–C10)-cycloalkyl or -cycloalkenyl]-(C1–C12)-aliphatic,
(C6–C10)-aryl,
(C6–C10)-aryl-(C1–C12)aliphatic,
(C3–C10)-heterocyclyl,
(C6–C10)-heterocyclyl-(C1–C12)aliphatic,
(C5–C10)-heteroaryl, or
(C5–C10)-heteroaryl-(C1–C12)-aliphatic;
R₁ and R₃ are independently:
(C1–C12)-aliphatic,
(C3–C10)-cycloalkyl or -cycloalkenyl,
[(C3–C10)-cycloalkyl or -cycloalkenyl]-(C1–C12)-aliphatic,
(C6–C10)-aryl,
(C6–C10)-aryl-(C1–C12)aliphatic,
(C3–C10)-heterocyclyl,
(C6–C10)-heterocyclyl-(C1–C12)aliphatic,
(C5–C10)-heteroaryl, or
(C5–C10)-heteroaryl-(C1–C12)-aliphatic, wherein each of $R_1$ and $R_3$ is independently and optionally substituted with up to 3 substituents independently selected from J;

wherein up to 3 aliphatic carbon atoms in $R_1$ and $R_3$ may be replaced by a heteroatom selected from O, NH, S, SO, or $SO_2$ in a chemically stable arrangement;

$R_2$ and $R_4$ are independently
hydrogen,
(C1–C12)-aliphatic,
(C3–C10)-cycloalkyl-(C1–C12)-aliphatic, or
(C6–C10)aryl-(C1–C12)-aliphatic, wherein each of $R_2$ and $R_4$ is independently and optionally substituted with up to 3 substituents independently selected from J;

wherein up to two aliphatic carbon atoms in $R_2$ and $R_4$ may be replaced by a heteroatom selected from O, NH, S, SO, or $SO_2$;

$R_5$ is (C1–C12)-aliphatic, wherein any hydrogen is optionally replaced with halogen, and wherein any hydrogen or halogen atom bound to any terminal carbon atom of $R_5$ is optionally substituted with sulfhydryl or hydroxy;

W is selected from:

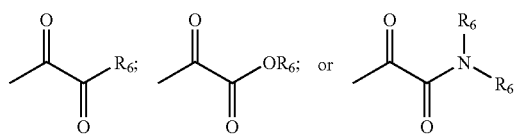

wherein each $R_6$ is independently:
hydrogen,
(C1–C12)-aliphatic,
(C6–C10)-aryl,
(C6–C10)-aryl-(C1–C12)aliphatic,
(C3–C10)-cycloalkyl or -cycloalkenyl,
[(C3–C10)-cycloalkyl or -cycloalkenyl]-(C1–C12)-aliphatic,
(C3–C10)-heterocyclyl,
(C3–C10)-heterocyclyl-(C1–C12)-aliphatic,
(C5–C10)heteroaryl, or
(C5–C10)heteroaryl-(C1–C12)-aliphatic, or two $R_6$ groups, which are bound to the same nitrogen atom, form together with that nitrogen atom, a (C3–C10)-heterocyclic ring;

wherein $R_6$ is optionally substituted with up to 3 J substituents;

V is —C(O)N($R_8$)—, —S(O)N($R_8$)—, or —S(O)$_2$N($R_8$)—;

wherein $R_8$ is hydrogen or (C1–C12)-aliphatic;

T is selected from:
(C6–C10)-aryl,
(C6–C10)-aryl-(C1–C12)aliphatic,
(C3–C10)-cycloalkyl or -cycloalkenyl,
[(C3–C10)-cycloalkyl or -cycloalkenyl]-(C1–C12)-aliphatic,
(C3–C10)-heterocyclyl,
(C3–C10)-heterocyclyl-(C1–C12)-aliphatic,
(C5–C10)heteroaryl, or
(C5–C10)heteroaryl-(C1–C12)-aliphatic; or T is selected from:

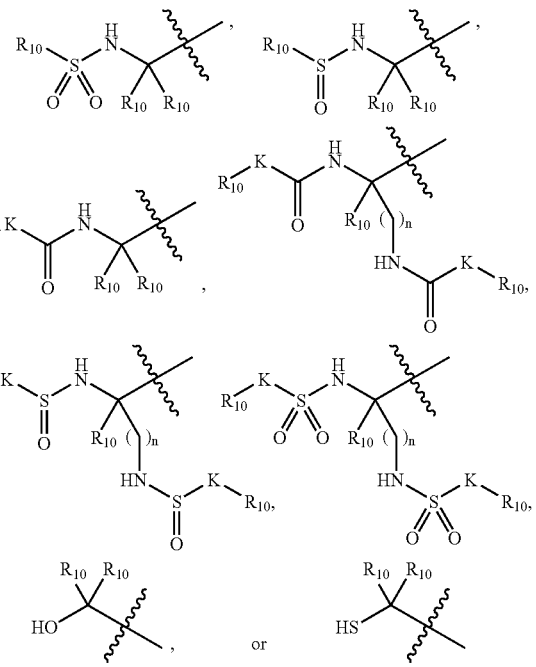

wherein:
$R_{10}$ is:
hydrogen,
(C1–C12)-aliphatic,
(C6–C10)-aryl,
(C6–C10)-aryl-(C1–C12)aliphatic,
(C3–C10)-cycloalkyl or -cycloalkenyl,
[(C3–C10)-cycloalkyl or -cycloalkenyl]-(C1–C12)-aliphatic,
(C3–C10)-heterocyclyl,
(C3–C10)-heterocyclyl-(C1–C12)-aliphatic,
(C5–C10)-heteroaryl, or
(C5–C10)-heteroaryl-(C1–C12)-aliphatic, wherein each T is optionally substituted with up to 3 J substituents;

K is a bond, (C1–C12)-aliphatic, —O—, —S—, —NR$_9$—, —C(O)—, or —C(O)—NR$_9$—, wherein $R_9$ is hydrogen or (C1–C12)-aliphatic; and n is 1–3.

In another embodiment, the invention provides a compound of formula (IB):

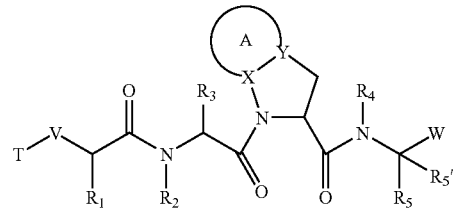

(IB)

wherein:
A, together with X and Y, is:
a 3- to 6-membered aromatic or non-aromatic ring having up to 3 heteroatoms independently selected from N, NH, O, S, SO, or $SO_2$;
wherein said ring is optionally fused to a (C6–C10)aryl, (C5–C10)heteroaryl, (C3–C10)cycloalkyl, or (C3–C10)heterocyclyl;
wherein A has up to 3 substituents selected independently from J and wherein the 5-membered ring to which A is fused has up to 4 substituents selected independently from J; and
wherein X and Y are independently C(H) or N;
J is halogen, —OR', —OC(O)N(R')$_2$, —NO$_2$, —CN, —CF$_3$, —OCF$_3$, —R', oxo, thioxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'); wherein:
two R' groups together with the atoms to which they are bound form a 3- to 10-membered aromatic or non-aromatic ring having up to 3 heteroatoms independently selected from N, NH, O, S, SO, or $SO_2$, wherein the ring is optionally fused to a (C6–C10)aryl, (C5–C10)heteroaryl, (C3–C10)cycloalkyl, or a (C3–C10)heterocyclyl, and wherein any ring has up to 3 substituents selected independently from J$_2$; or
each R' is independently selected from:
hydrogen-,
(C1–C12)-aliphatic-,
(C3–C10)-cycloalkyl or -cycloalkenyl-,
[(C3–C10)-cycloalkyl or -cycloalkenyl]-(C1–C12)-aliphatic-,
(C6–C10)-aryl-,
(C6–C10)-aryl-(C1–C12)aliphatic-,
(C3–C10)-heterocyclyl-,
(C6–C10)-heterocyclyl-(C1–C12)aliphatic-,
(C5–C10)-heteroaryl-, or
(C5–C10)-heteroaryl-(C1–C12)-aliphatic-;

wherein R' has up to 3 substituents selected independently from J$_2$; and
J$_2$ is halogen, —OR', —OC(O)N(R')$_2$, —NO$_2$, —CN, —CF$_3$, —OCF$_3$, —R', oxo, thioxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR').

R$_1$ and R$_3$ are independently:
(C1–C12)-aliphatic-,
(C3–C10)-cycloalkyl- or -cycloalkenyl-,
[(C3–C10)-cycloalkyl- or -cycloalkenyl]-(C1–C12)—aliphatic-,
(C6–C10)-aryl-,
(C6–C10)-aryl-(C1–C12)aliphatic-,
(C3–C10)-heterocyclyl-,
(C6–C10)-heterocyclyl-(C1–C12)aliphatic-,
(C5–C10)-heteroaryl-, or
(C5–C10)-heteroaryl-(C1–C12)-aliphatic-,
wherein each of R$_1$ and R$_3$ is independently and optionally substituted with up to 3 substituents independently selected from J;
wherein up to 3 aliphatic carbon atoms in R$_1$ and R$_3$ may be replaced by a heteroatom selected from O, N, NH, S, SO, or $SO_2$ in a chemically stable arrangement;
R$_2$ and R$_4$ are independently:
hydrogen-,
(C1–C12)-aliphatic-,
(C3–C10)-cycloalkyl-(C1–C12)-aliphatic-, or
(C6–C10)aryl-(C1–C12)-aliphatic-,
wherein each of R$_2$ and R$_4$ is independently and optionally substituted with up to 3 substituents independently selected from J;
wherein up to two aliphatic carbon atoms in R$_2$ and R$_4$ may be replaced by a heteroatom selected from O, N, NH, S, SO, or $SO_2$;
R$_5$ is (C1–C12)-aliphatic, wherein any hydrogen is optionally replaced with halogen, and wherein any terminal carbon atom of R$_5$ is optionally substituted with sulfhydryl or hydroxy;
R$_{5'}$ is hydrogen or (C1–C12)-aliphatic, wherein any hydrogen is optionally replaced with halogen, and wherein any hydrogen or halogen atom bound to any terminal carbon atom of R$_5$ is optionally substituted with sulfhydryl or hydroxy;
W is:

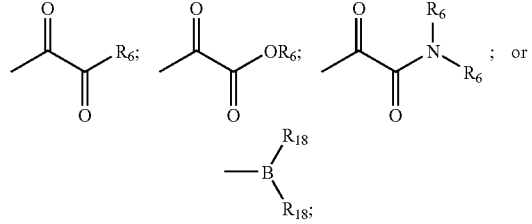

wherein each R$_6$ is independently:
hydrogen-,
(C1–C12)-aliphatic-,
(C6–C10)-aryl-,
(C6–C10)-aryl-(C1–C12)aliphatic-,
(C3–C10)-cycloalkyl or -cycloalkenyl-,
[(C3–C10)-cycloalkyl or -cycloalkenyl]-(C1–C12)-aliphatic-,
(C3–C10)-heterocyclyl-,
(C3–C10)-heterocyclyl-(C1–C12)-aliphatic-,
(C5–C10)heteroaryl-, or
(C5–C10)heteroaryl-(C1–C12)-aliphatic-, or
two R$_6$ groups, which are bound to the same nitrogen atom, form together with that nitrogen atom, a (C3–C10)-heterocyclic ring;
wherein R$_6$ is optionally substituted with up to 3 J substituents;
each R$_{18}$ is independently —OR'; or the R$_{18}$ groups together with the boron atom, is a (C3–C10)-membered heterocyclic ring having in addition to the boron up to 3 additional heteroatoms selected from N, NH, O, S, SO, and $SO_2$;

V is —C(O)N($R_8$)—, —S(O)N($R_8$)—, —S(O)$_2$N($R_8$)—, —OS(O)—, —OS(O)$_2$—, —OC(O)—, or —O—; wherein $R_8$ is hydrogen or (C1–C12)-aliphatic;

T is:
- (C1–C12)-aliphatic-;
- (C6–C10)-aryl-,
- (C6–C10)-aryl-(C1–C12)aliphatic-,
- (C3–C10)-cycloalkyl or -cycloalkenyl-,
- [(C3–C10)-cycloalkyl or -cycloalkenyl]-(C1–C12)-aliphatic-,
- (C3–C10)-heterocyclyl-,
- (C3–C10)-heterocyclyl-(C1–C12)-aliphatic-,
- (C5–C10)heteroaryl-, or
- (C5–C10)heteroaryl-(C1–C12)-aliphatic-; or T is:

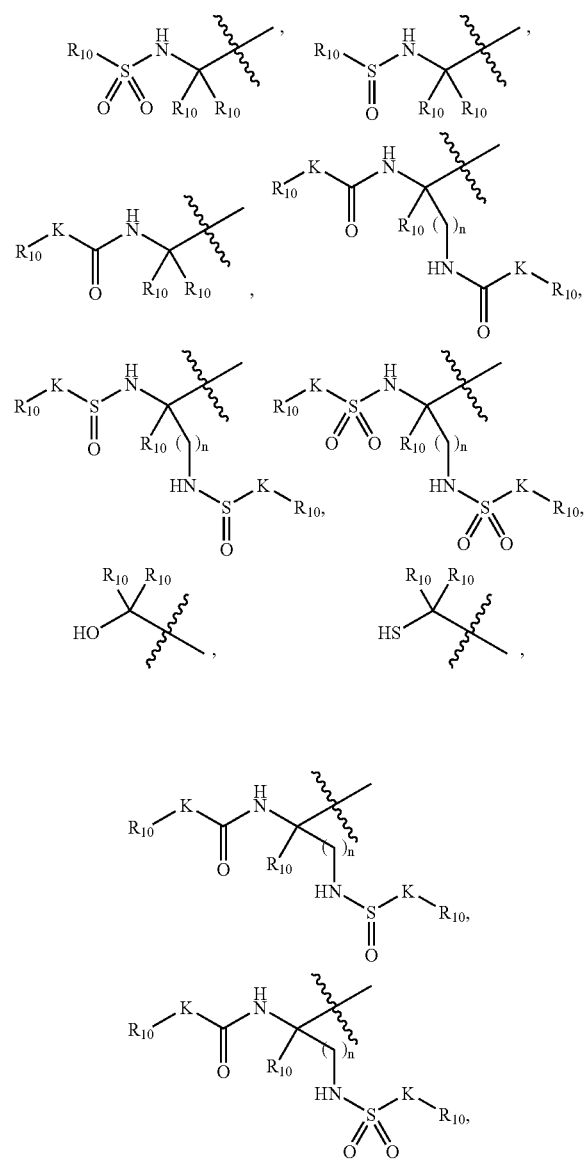

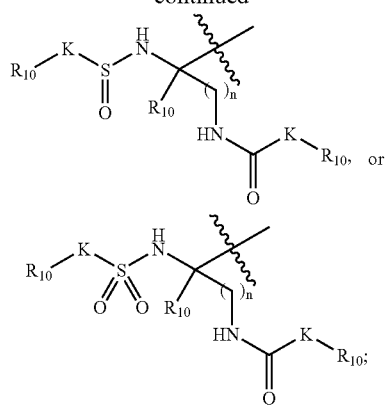

wherein:

$R_{10}$ is:
- Hydrogen-,
- (C1–C12)-aliphatic-,
- (C6–C10)-aryl-,
- (C6–C10)-aryl-(C1–C2)aliphatic-,
- (C3–C10)-cycloalkyl or -cycloalkenyl-,
- [(C3–C10)-cycloalkyl or -cycloalkenyl]-(C1–C12)-aliphatic-,
- (C3–C10)-heterocyclyl-,
- (C3–C10)-heterocyclyl-(C1–C12)-aliphatic-,
- (C5–C10)-heteroaryl-, or
- (C5–C10)-heteroaryl-(C1–C12)-aliphatic-, wherein each T is optionally substituted with up to 3 J substituents;

K is a bond, (C1–C12)-aliphatic, —O—, —S—, —N$R_9$—, —C(O)—, or —C(O)—N$R_9$—, wherein $R_9$ is hydrogen or (C1–C12)-aliphatic; and n is 1–3.

In yet another embodiment, the invention provides a compound of formula (II):

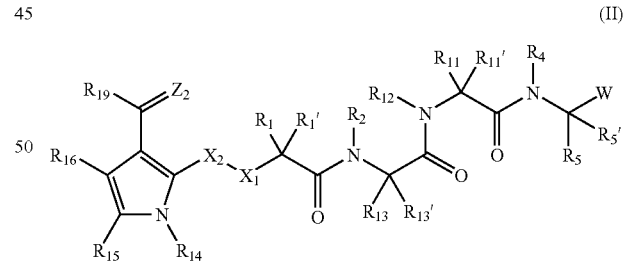

(II)

wherein:

$X_1$ is —N($R_{20}$)—, —O—, —S—, or —C(R)$_2$—;
$X_2$ is —C(O)—, —C(S)—, —S(O)—, or —S(O)$_2$—;
W is:

 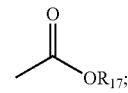 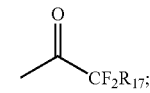

-continued

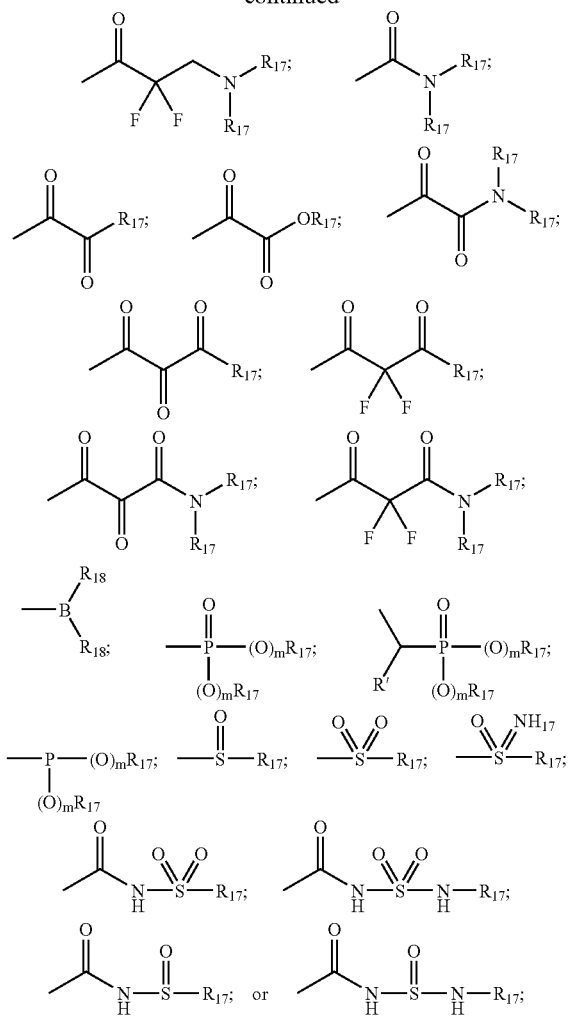

m is 0 or 1;
each $R_{17}$ is independently:
  hydrogen-,
  (C1–C12)-aliphatic-,
  (C3–C10)-cycloalkyl or -cycloalkenyl-,
  [(C3–C10)-cycloalkyl or -cycloalkenyl]-(C1–C12)-aliphatic-,
  (C6–C10)-aryl-,
  (C6–C10)-aryl-(C1–C12)aliphatic-,
  (C3–C10)-heterocyclyl-,
  (C3–C10)-heterocyclyl-(C1–C12)-aliphatic-,
  (C5–C10)heteroaryl-, or
  (C5–C10)heteroaryl-(C1–C12)-aliphatic-, or
  two $R_{17}$ groups, which are bound to the same nitrogen atom, form together with that nitrogen atom, a (C3–C10)-membered heterocyclic ring having in addition to the nitrogen up to 2 additional heteroatoms selected from N, NH, O, S, SO, and $SO_2$;
wherein $R_{17}$ is optionally substituted with up to 3 J substituents;
each $R_{18}$ is independently —OR'; or both OR' groups together with the boron atom, is a (C5–C20)-membered heterocyclic ring having in addition to the boron up to 3 additional heteroatoms selected from N, NH, O, S, SO, and $SO_2$;

$R_5$ and $R_{5'}$ are independently hydrogen or (C1–C12)-aliphatic, wherein any hydrogen is optionally replaced with halogen, and wherein any terminal carbon atom is optionally substituted with sulfhydryl or hydroxy, and wherein up to two aliphatic carbon atoms may be replaced by a heteroatom selected from N, NH, O, S, SO, or $SO_2$; or $R_5$ and $R_{5'}$ together with the atom to which they are bound is a 3- to 6-membered ring having up to 2 heteroatoms selected from N, NH, O, S, SO, or $SO_2$; wherein the ring has up to 2 substituents selected independently from J;

$R_1$, $R_{1'}$, $R_{11}$, $R_{11'}$, $R_{13}$, and $R_{13'}$ are independently:
  hydrogen-,
  (C1–C12)-aliphatic-,
  (C3–C10)-cycloalkyl or -cycloalkenyl-,
  [(C3–C10)-cycloalkyl or -cycloalkenyl]-(C1–C12)-aliphatic-,
  (C6–C10)-aryl-,
  (C6–C10)-aryl-(C1–C12)aliphatic-,
  (C3–C10)-heterocyclyl-,
  (C6–C10)-heterocyclyl-(C1–C12)aliphatic,
  (C5–C10)-heteroaryl-, or
  (C5–C10)-heteroaryl-(C1–C12)-aliphatic-; or $R_1$ and $R_{1'}$ together with the atom to which they are bound is a 3- to 6-membered ring having up to 2 heteroatoms selected from N, NH, O, S, SO, or $SO_2$; wherein the ring has up to 2 substituents selected independently from J; or $R_{11}$ and $R_{11'}$ together with the atom to which they are bound is a 3- to 6-membered ring having up to 2 heteroatoms selected from N, NH, O, S, SO, or $SO_2$; wherein the ring has up to 2 substituents selected independently from J; or $R_{13}$ and $R_{13'}$ together with the atom to which they are bound is a 3- to 6-membered ring having up to 2 heteroatoms selected from N, NH, O, S, SO, or $SO_2$; wherein the ring has up to 2 substituents selected independently from J;
  wherein each of $R_1$, $R_{1'}$, $R_{11}$, $R_{11'}$, $R_{13}$, and $R_{13'}$ is independently and optionally substituted with up to 3 substituents independently selected from J; and wherein any ring is optionally fused to a (C6–C10) aryl, (C5–C10)heteroaryl, (C3–C10)cycloalkyl, or (C3–C10)heterocyclyl; and wherein up to 3 aliphatic carbon atoms in each of $R_1$, $R_{1'}$, $R_{11}$, $R_{11'}$, $R_{13}$, and $R_{13'}$ may be replaced by a heteroatom selected from O, N, NH, S, SO, or $SO_2$ in a chemically stable arrangement;

$R_2$, $R_4$, $R_{12}$, and $R_{20}$ are independently
  hydrogen-,
  (C1–C12)-aliphatic-,
  (C3–C10)-cycloalkyl-,
  (C3–C10)-cycloalkyl-(C1–C12)-aliphatic-, or
  (C6–C10)aryl-(C1–C12)-aliphatic-,
  wherein each $R_2$, $R_4$, $R_{12}$, and $R_{20}$ is independently and optionally substituted with up to 3 substituents independently selected from J;
  wherein up to two aliphatic carbon atoms in $R_2$, $R_4$, $R_{12}$, and $R_{20}$ may be replaced by a heteroatom selected from O, N, NH, S, SO, or $SO_2$; or $R_{11}$ and $R_{12}$ together with the atoms to which they are bound form a 3- to a 20-membered mono-, a 4- to 20-membered bi-, or a 5- to 20-membered tri-cyclic carbocyclic or heterocyclic ring system;
  wherein, in the bi- and tri-cyclic ring system, each ring is linearly fused, bridged, or spirocyclic;

wherein each ring is either aromatic or nonaromatic;
wherein each heteroatom in the heterocyclic ring system is selected from the group consisting of N, NH, O, S, SO, and $SO_2$;
wherein each ring is optionally fused to a (C6–C10) aryl, (C5–C10)heteroaryl, (C3–C10)cycloalkyl, or (C3–C10)heterocyclyl; and
wherein said ring has up to 3 substituents selected independently from J; or $R_{12}$ and $R_{13}$ together with the atoms to which they are bound form a 4- to a 20-membered mono-, a 5- to 20-membered bi-, or a 6- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6–C10) aryl, (C5–C10)heteroaryl, (C3–C10)cycloalkyl, or (C3–C10)heterocyclyl; and
wherein said ring has up to 3 substituents selected independently from J; or $R_{11}$ and $R_{13}$ together with the atoms to which they are bound form a 5- to a 20-membered mono-, a 6- to 20-membered bi-, or a 7- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6–C10) aryl, (C5–C10)heteroaryl, (C3–C10)cycloalkyl, or (C3–C10)heterocyclyl; and
wherein said ring has up to 3 substituents selected independently from J; or $R_{11}$, $R_{12}$, and $R_{13}$ together with the atoms to which they are bound form a 5- to a 20-membered bi-, or a 6- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6–C10) aryl, (C5–C10)heteroaryl, (C3–C10)cycloalkyl, or (C3–C10)heterocyclyl; and
wherein said ring has up to 3 substituents selected independently from J; or $R_{13'}$ and $R_2$ together with the atoms to which they are bound form a 3- to a 20-membered mono-, a 4- to 20-membered bi-, or a 5- to 20-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6–C10) aryl, (C5–C10)heteroaryl, (C3–C10)cycloalkyl, or (C3–C10)heterocyclyl; and
wherein said ring has up to 3 substituents selected independently from J;

$R_5$ and $R_{13}$ together with the atoms to which they are bound form a 18- to a 23-membered mono-, a 19- to 24-membered bi-, or a 20- to 25-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6–C10) aryl, (C5–C10)heteroaryl, (C3–C10)cycloalkyl, or (C3–C10)heterocyclyl; and
wherein said ring has up to 6 substituents selected independently from J; or $R_1$ and $R_{12}$ together with the atoms to which they are bound form a 18- to a 23-membered mono-, a 19- to 24-membered bi-, or a 20- to 25-membered tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6–C10) aryl, (C5–C10)heteroaryl, (C3–C10)cycloalkyl, or (C3–C10)heterocyclyl; and wherein said ring has up to 6 substituents selected independently from J; or $R_{14}$ is —H, —S(O)R', —S(O)$_2$R', —C(O)R', —C(O)OR', —C(O)N(R')$_2$, —N(R')C(O)R', —N(COR')COR', —SO$_2$N(R')$_2$, —SO$_3$R', —C(O)C(O)R', —C(O)CH$_2$C(O)R', —C(S)R', —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR')

$R_{15}$ and $R_{16}$ are independently halogen, —OR', —OC(O)N(R')$_2$, —NO$_2$, —CN, —CF$_3$, —OCF$_3$, —R', oxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');

$Z_2$ is =O, =NR', =NOR', or =C(R')$_2$;

$R_{19}$ is —OR', —CF$_3$, —OCF$_3$, —R', —N(R')$_2$, —SR', —C(O)R', —COOR'—CON(R')$_2$, —N(R')COR', or —N(COR')COR';

J is halogen, —OR', —OC(O)N(R')$_2$, —NO$_2$, —CN, —CF$_3$, —OCF$_3$, —R', oxo, thioxo, 1,2-methylenedioxy, 1,2-ethyenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'); wherein:

two R' groups together with the atoms to which they are bound form a 3- to 10-membered aromatic or non-aromatic ring having up to 3 heteroatoms independently selected from N, NH, O, S, SO, or SO$_2$, wherein the ring is optionally fused to a (C6–C10)aryl, (C5–C10)heteroaryl, (C3–C10)cycloalkyl, or a (C3–C10)heterocyclyl, and wherein any ring has up to 3 substituents selected independently from J$_2$; or each R' is independently selected from:
hydrogen-,
(C1–C12)-aliphatic-,
(C3–C10)-cycloalkyl or -cycloalkenyl-,
[(C3–C10)-cycloalkyl or -cycloalkenyl]-(C1–C12)-aliphatic-,
(C6–C10)-aryl-,
(C6–C10)-aryl-(C1–C12)aliphatic-,
(C3–C10)-heterocyclyl-,
(C6–C10)-heterocyclyl-(C1–C12)aliphatic-,
(C5–C10)-heteroaryl-, or
(C5–C10)-heteroaryl-(C1–C12)-aliphatic-;

wherein R' has up to 3 substituents selected independently from J$_2$; and

J$_2$ is halogen, —OR', —OC(O)N(R')$_2$, —NO$_2$, —CN, —CF$_3$, —OCF$_3$, —R', oxo, thioxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR').

Definitions

References herein to formula (I) are meant to include both formula (IA) and formula (IB).

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin.

The term "heterocyclyl" as used herein means a monocyclic or bicyclic non-aromatic ring system having 1 to 3 heteroatom or heteroatom groups in each ring selected from O, N, NH, S, SO, or SO$_2$ in a chemically stable arrangement. In a bicyclic non-aromatic ring system embodiment of "heterocyclyl" one or both rings may contain said heteroatom or heteroatom groups.

The term "heteroaryl" as used herein means a monocyclic or bicyclic aromatic ring system having 1 to 3 heteroatom or heteroatom groups in each ring selected from O, N, NH or S in a chemically stable arrangement. In such a bicyclic aromatic ring system embodiment of "heteroaryl":

one or both rings may be aromatic; and
one or both rings may contain said heteroatom or heteroatom groups.

The term "aliphatic" as used herein means a straight chained or branched alkyl, alkenyl or alkynyl. It is understood that alkenyl or alkynyl embodiments need at least two carbon atoms in the aliphatic chain.

The term "cycloalkyl or cycloalkenyl" refers to a monocyclic or fused or bridged bicyclic carbocyclic ring system that is not aromatic. Cycloalkenyl rings have one or more units of unsaturation. Preferred cycloalkyl groups include cyclopropyl, cyclobutyl, cyclopentyl, cyclohexyl, cyclohexenyl, cycloheptyl, cycloheptenyl, nornbornyl, adamantyl and decalin-yl.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

The compounds of formulae (IA) and (IB) of the present invention represent a selection from the genus of WO 02/18369. Applicants have invented a subgenus within the genus of WO 02/18369 that contain one or both of the following two distinct structural elements:

1. a fused azaheterocyclic ring system containing ring A, wherein ring A in formula (I) is adjacent to the ring nitrogen atom (i.e., atom X in formula (I) is adjacent to the ring nitrogen atom of the backbone);

2. a hydrogen bond donor in the P4 cap part of the compounds of formula (I) [radical T in formula (I)].

Without wishing to be bound by theory, applicants believe that the first structural element, namely, ring A, by being adjacent to the ring nitrogen atom on the backbone of compounds of formula (I), provides a facile orientation such that compounds of the present invention have an enhanced interaction with the P2 region of the active site of the serine protease. Applicants believe that the second structural element, a hydrogen bond donor in radical T in formula (I), provides an additional point of interaction between the compounds of the present invention and the serine protease active site, thereby enhancing the binding affinity.

In a preferred embodiment, the second structural element comprises the following moiety:

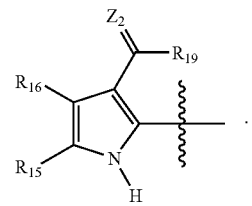

Without being bound by theory, applicants further believe that this pyrrole moiety (as the second structural element) provides particularly favorable hydrogen bond interactions with the serine protease active site, thereby enhancing the binding affinity of compounds having this moiety. This favorable interaction enhances the binding affinity of compounds having the first structural element (i.e., ring A) as well as those having other structural elements.

As would be recognized by a skilled practitioner, the hydrogen on the 1-position of the pyrrole could be substituted with an appropriate group (e.g., $R_{14}$ as defined herein) to enhance biological properties. Therefore, one embodiment of this invention provides a compound of formula (III), wherein P1, P2, P3, and P4 designate the residues of a serine protease inhibitor as known to those skilled in the art and $R_{14}$, $R_{15}$, $R_{16}$, $R_{19}$, and $Z_2$ are as defined herein:

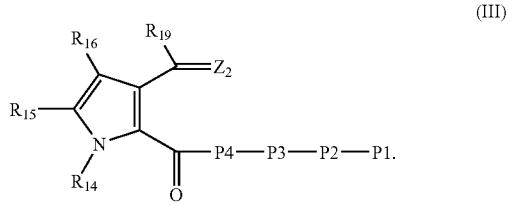

(III)

All compounds, therefore, having: 1) structural elements of a serine protease inhibitor; and 2) the pyrrole-moiety are considered part of this invention. Compounds having the structural elements of a serine protease inhibitor include, but are not limited to, the compounds of the following publications: WO 97/43310, US20020016294, WO 01/81325, WO 02/08198, WO 01/77113, WO 02/08187, WO 02/08256, WO 02/08244, WO 03/006490, WO 01/74768, WO 99/50230, WO 98/17679, WO 02/48157, US20020177725, WO 02/060926, US20030008828, WO 02/48116, WO 01/64678, WO 01/07407, WO 98/46630, WO 00/59929, WO 99/07733, WO 00/09588, US20020016442, WO 00/09543, WO 99/07734, U.S. Pat. No. 6,018,020, WO 98/22496, U.S. Pat. No. 5,866,684, WO 02/079234, WO 00/31129, WO 99/38888, WO 99/64442, and WO 02/18369, which are incorporated herein by reference.

Thus, any compound of the above publications may be modified to have this pyrrole moiety, or a derivative thereof. Any such compound is part of this invention. For example, compound A in WO 02/18369 (p. 41):

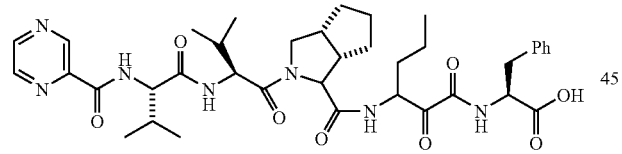

may be modified to provide the following compound of this invention:

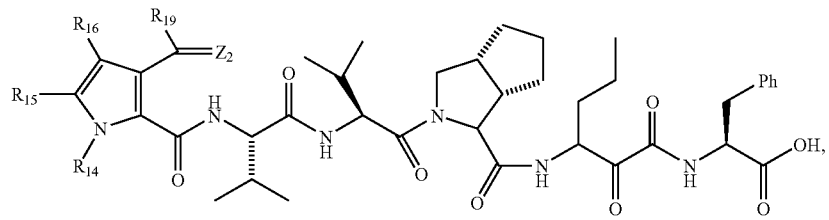

wherein $R_{14}$, $R_{15}$, $R_{16}$, $R_{19}$, and $Z_2$ are as defined herein.

PREFERRED EMBODIMENTS

According to a preferred embodiment of formula (I), A together with X and Y is a 3–6 membered carbocyclic non-aromatic or aromatic ring. More preferably, A together with X and Y is cyclopropyl, cyclobutyl, cyclopentyl, cyclohexyl or phenyl. Even more preferably, A together with X and Y is cylcohexyl or cyclopentyl. Most preferably, A together with X and Y is cyclohexyl.

According to another preferred embodiment, A together with X and Y is a 3–6 membered heterocyclic ring. More preferably, A together with X and Y is a 5–6 membered heterocyclic ring.

According to another preferred embodiment, A together with X and Y is a 5–6 membered heteroaryl ring.

According to yet another preferred embodiment, A together with X and Y is fused to a (C6–C10)aryl, (C5–C10) heteroaryl, (C3–C10)cycloalkyl or (C3–C10)-heterocyclyl. Preferably, A together with X and Y is fused to cyclohexyl, cyclopentyl, phenyl or pyridyl.

According to another preferred embodiment, the ring system

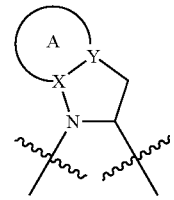

in formula (I) is selected from Table 1 below:

TABLE 1
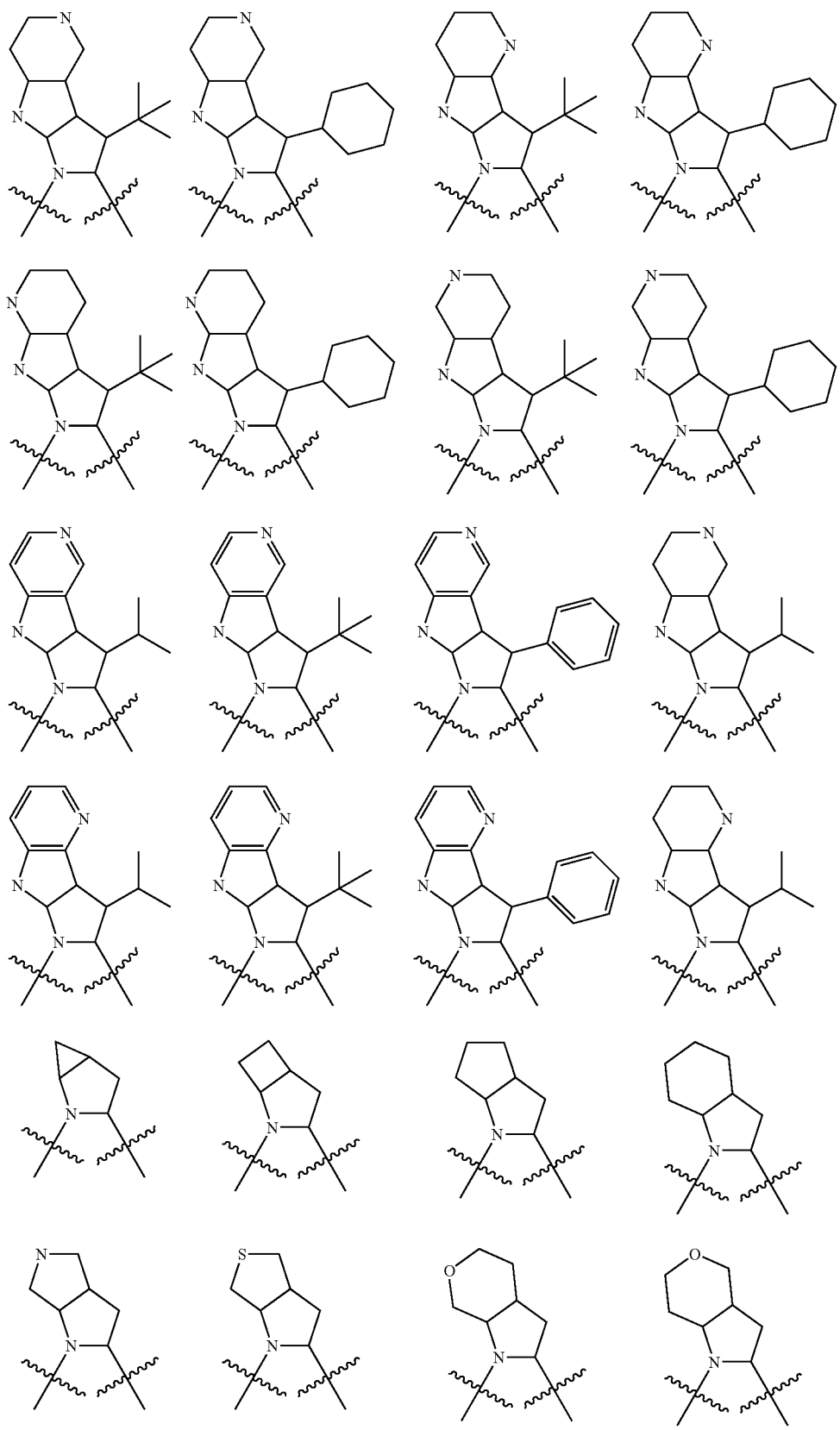

TABLE 1-continued
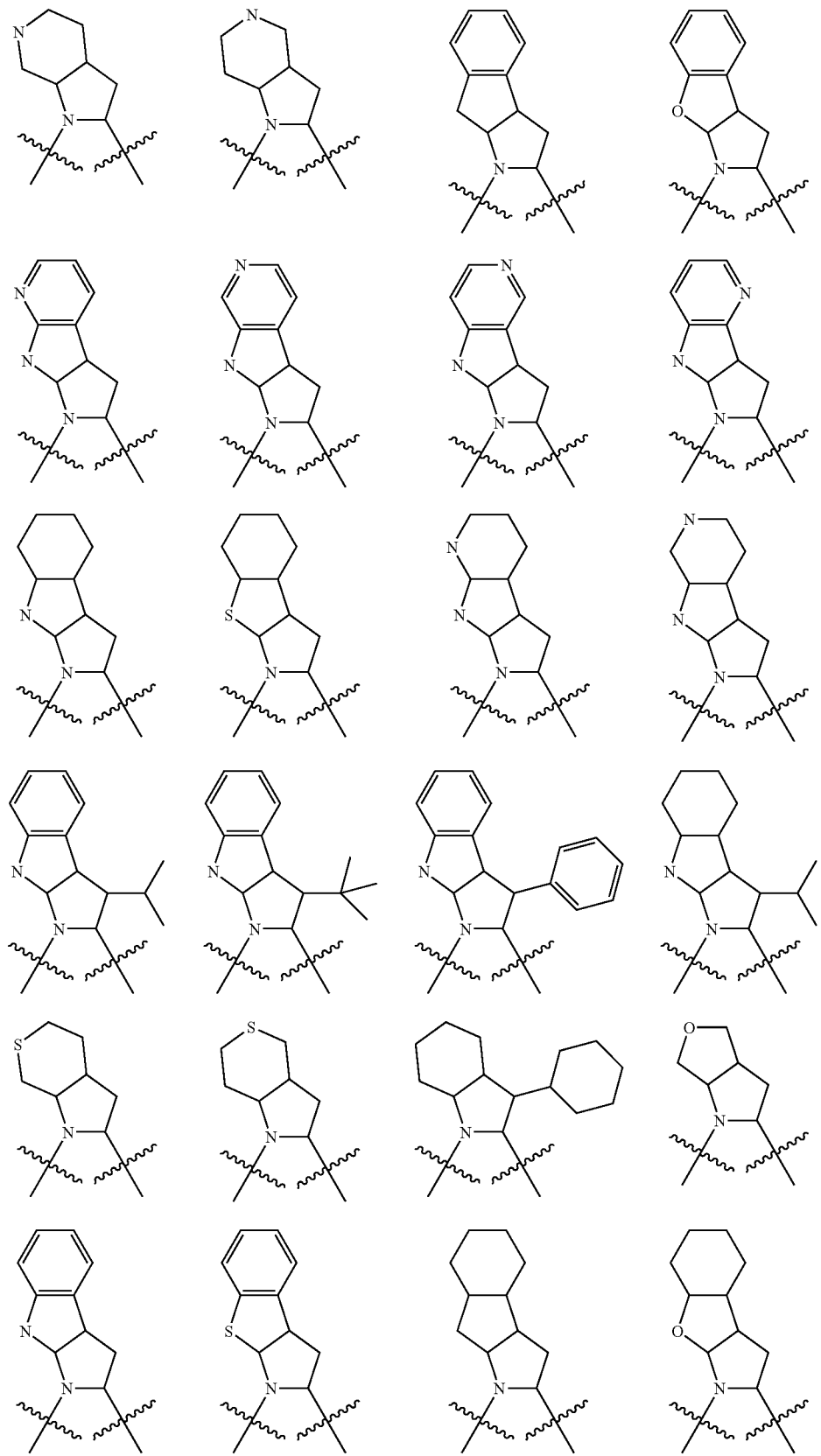

TABLE 1-continued
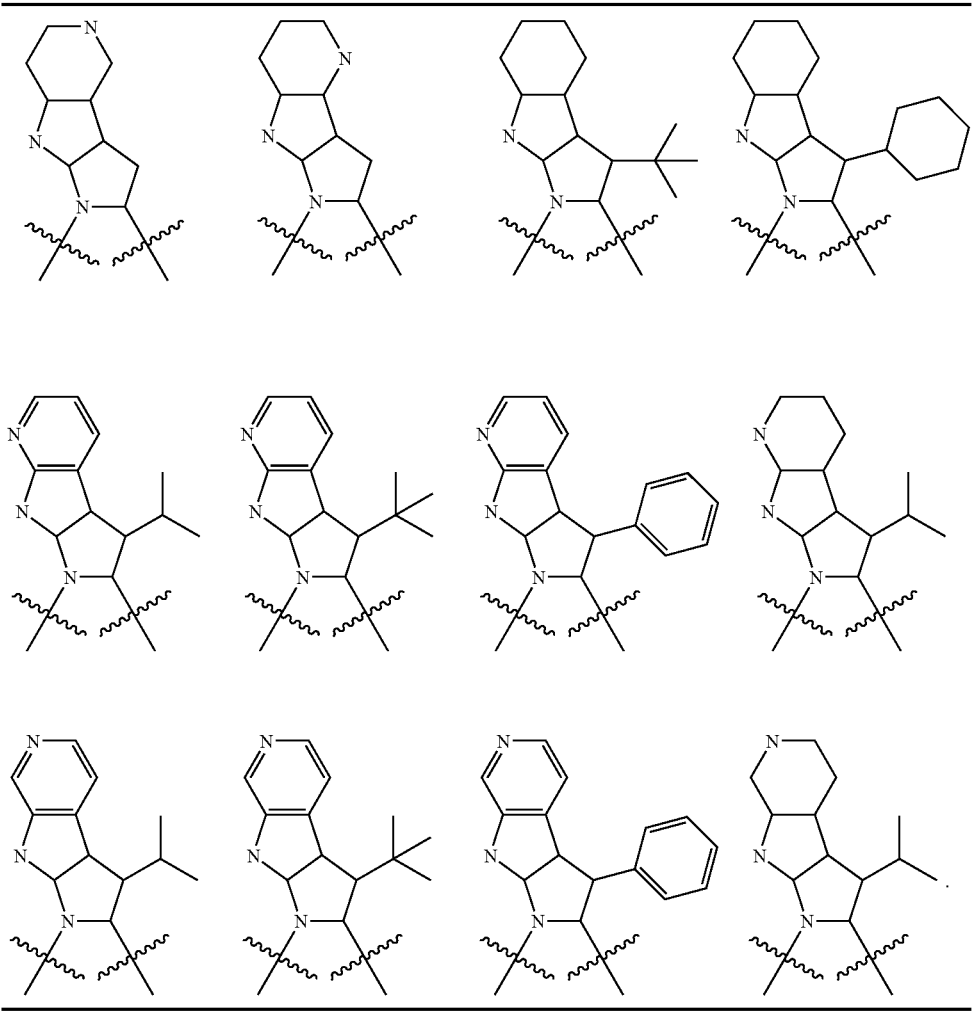
According to a more preferred embodiment, the ring system
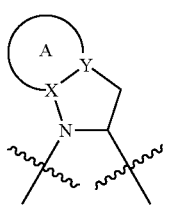
in formula (I) is selected from:
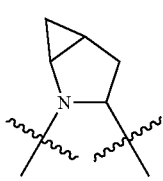 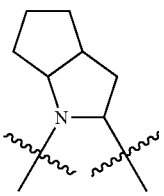
-continued
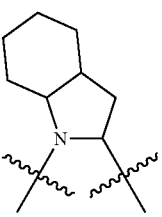 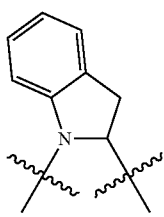
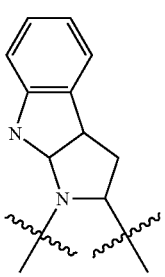 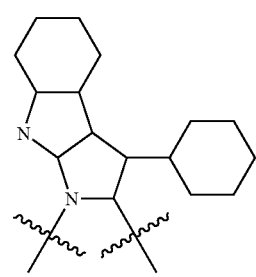

-continued

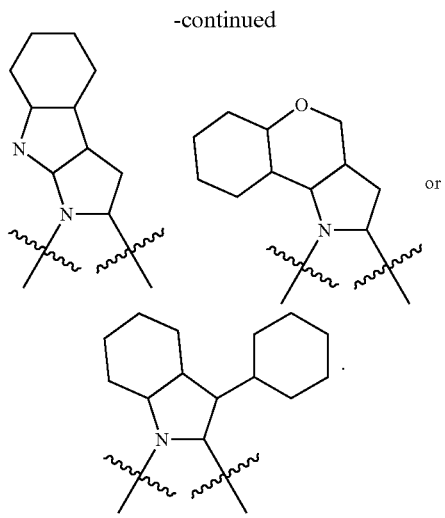

According to another more preferred embodiment, A, together with X, Y and the ring containing the nitrogen atom, is:

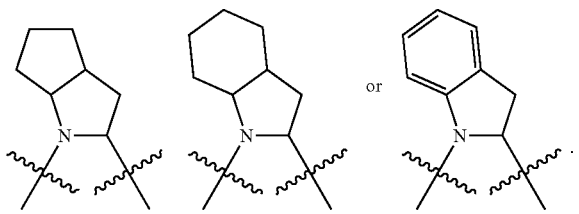

More preferably, A, together with X, Y and the ring containing the nitrogen atom, is:

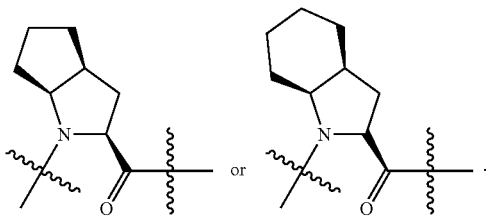

According to a preferred embodiment, T is selected from: (C6–C10)-aryl, (C6–C10)-aryl-(C1–C12)aliphatic, (C3–C10)-cycloalkyl or -cycloalkenyl, [(C3–C10)-cycloalkyl or -cycloalkenyl]-(C1–C12)-aliphatic, (C3–C10)-heterocyclyl, (C3–C10)-heterocyclyl-(C1–C12)-aliphatic, (C5–C10)heteroaryl, or (C5–C10)heteroaryl-(C1–C12)-aliphatic, wherein each T is optionally substituted with up to 3 J substituents.

According to another preferred embodiment, T is:

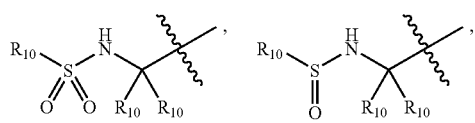

-continued

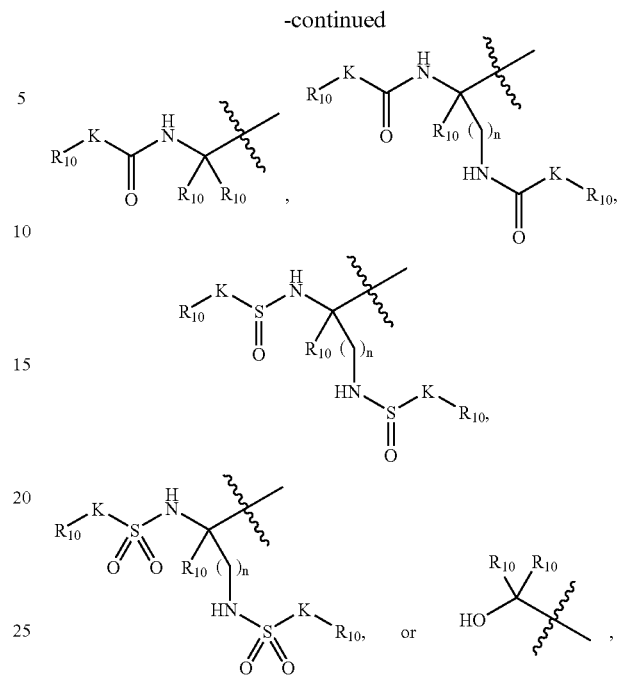

wherein:
R$_{10}$ is:
  hydrogen,
  (C1–C12)-aliphatic,
  (C6–C10)-aryl,
  (C6–C10)-aryl-(C1–C12)aliphatic,
  (C3–C10)-cycloalkyl or -cycloalkenyl,
  [(C3–C10)-cycloalkyl or -cycloalkenyl]-(C1–C12)-aliphatic,
  (C3–C10)-heterocyclyl,
  (C3–C10)-heterocyclyl-(C1–C12)-aliphatic,
  (C5–C10)heteroaryl, or
  (C5–C10)heteroaryl-(C1–C12)-aliphatic,
wherein each T is optionally substituted with up to 3 J substituents;
K is a bond, —R$_9$—, —O—, —S—, —NR$_9$—, —C(O)—, or —C(O)—NR$_9$—, wherein R$_9$ is hydrogen or C1–C12 aliphatic; and
n is 1–3.
In the above embodiment, T may also be:

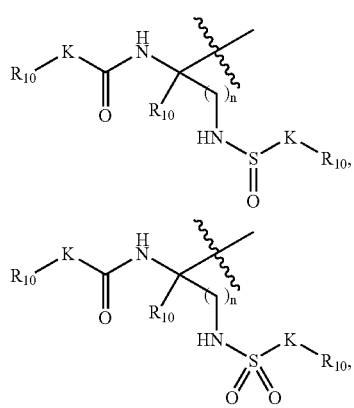

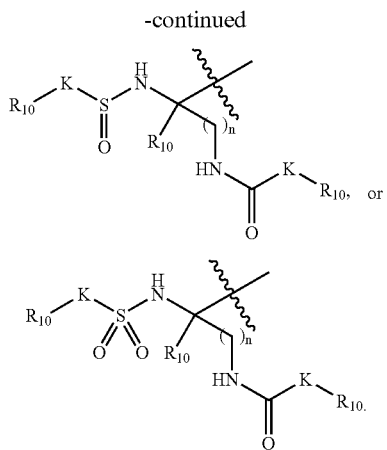
In a preferred embodiment, T is:
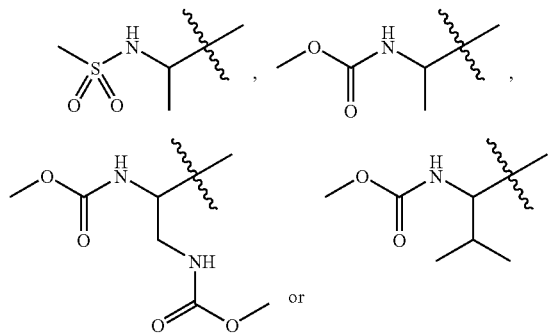
According to a more preferred embodiment, T contains at least one hydrogen bond donor moiety selected from —NH$_2$, —NH—, —OH or —SH.
According to another more preferred embodiment, T is selected from:
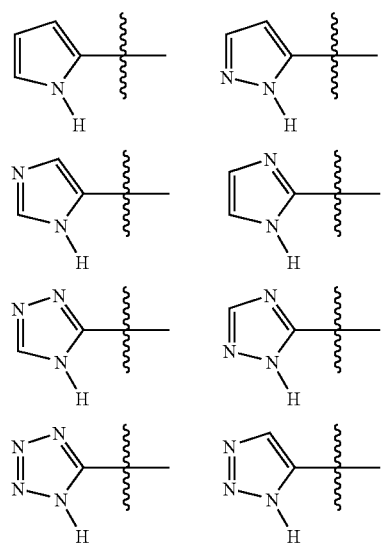
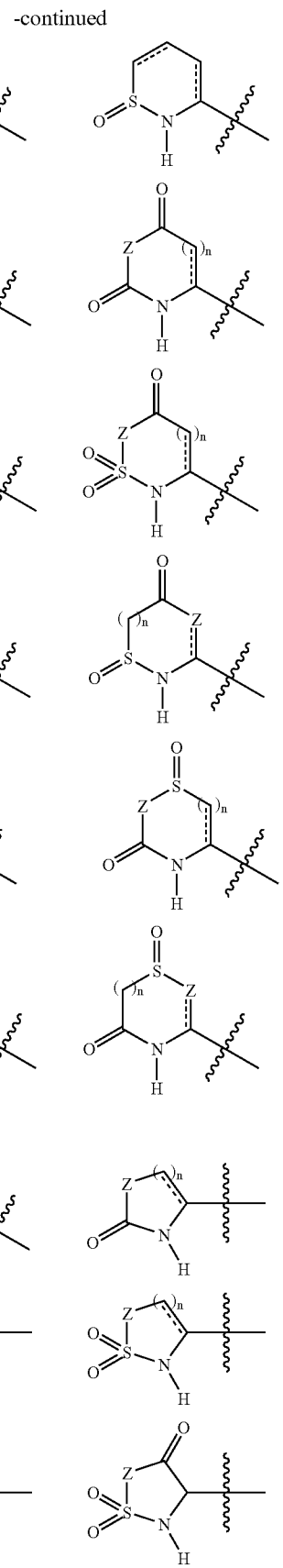

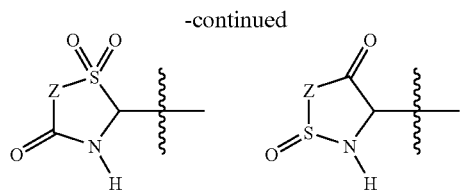

wherein:
  T is optionally substituted with up to 3 J substituents;
  z is independently O, S, $NR_{10}$, $C(R_{10})_2$;
  n is independently 1 or 2; and
  ----- is independently a single bond or a double bond.

According to yet another preferred embodiment, T is selected from:

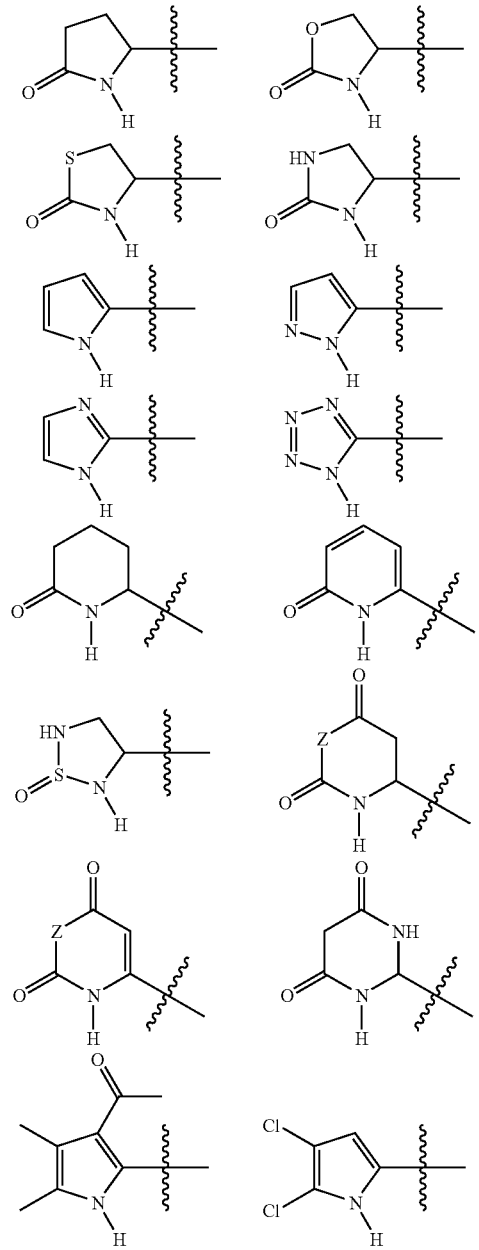

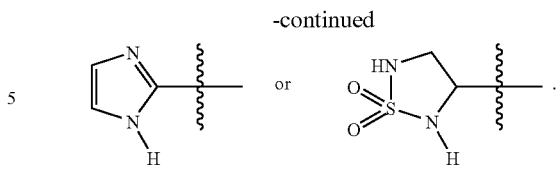

wherein Z is as defined above.

In a more preferred embodiment, T is:

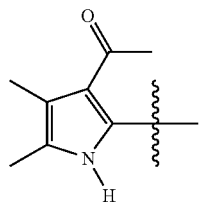

According to a preferred embodiment, W is —C(O)—C(O)—$R_6$ (or, in formula (II), —C(O)—C(O)—$R_{17}$).

Preferably, $R_6$ (and/or $R_{17}$) are: phenyl, pyridyl, (C3–C6)-alkyl, (C3–C6)-cycloalkyl, —OH, —O—(C1–C6)-alkyl, —N(H)—(C3–C6)-cycloalkyl, —N(H)—C(H)(CH$_3$)—(C6–C10)aryl, —N(H)—C(H)(CH$_3$)-(C3–C10)-heterocyclyl, or —N(H)—C(H)(CH$_3$)—(C5–C10)-heteroaryl, wherein each aryl, heterocyclyl, and heteroaryl is optionally substituted with halogen. Preferred embodiments are selected from:

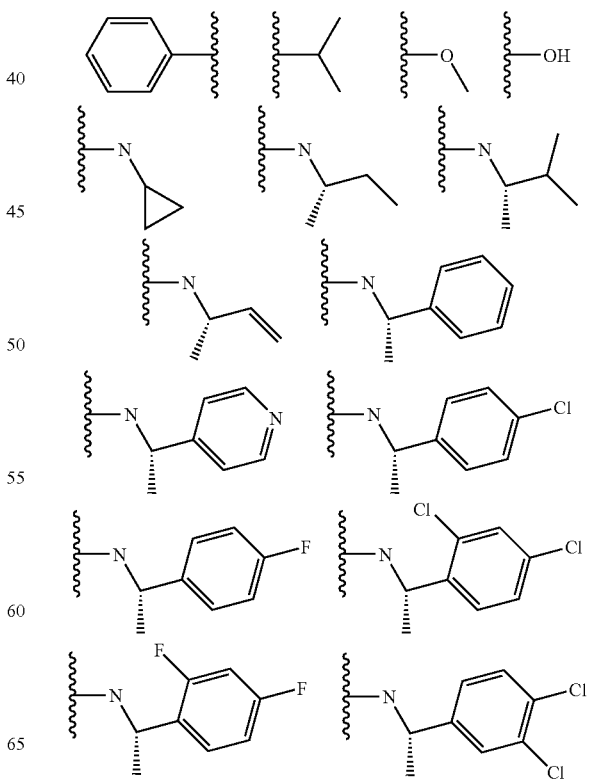

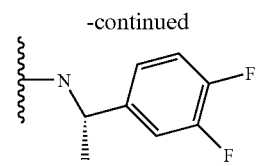

More preferably, $R_6$ (and/or $R_{17}$) are isopropyl.

According to another preferred embodiment of formula (II), W is —C(O)—H.

According to another preferred embodiment, W is —C(O)—C(O)—$OR_6$. More preferably, $R_6$ is H or methyl.

According to a more preferred embodiment, $R_6$ is selected from hydrogen, (C1–C12)-aliphatic, (C6–C10)-aryl, (C3–C10)-cycloalkyl or -cycloalkenyl, (C3–C10)-heterocyclyl or (C5–C10)heteroaryl.

According to another preferred embodiment, W is —C(O)—C(O)—$N(R_6)_2$. More preferably, $R_6$ is selected from hydrogen, (C3–C10)-cycloalkyl or -cycloalkenyl, or (C3–C10)-heterocyclyl. Alternatively, one $R_6$ is hydrogen and the other $R_6$ is: (C6–C10)-aryl-(C1–C3)alkyl-, wherein the alkyl is optionally substituted with $CO_2H$; (C3–C6) cycloalkyl-; (C5)-heterocylyl-(C1–C3)alkyl-; (C3–C6)alkenyl-; or each $R_6$ is (C1–C6)-alkyl-. Alternatively, each $R_6$ is (C1–C3)-alkyl-.

Most preferably, —$NHR_6$ in W is selected from:

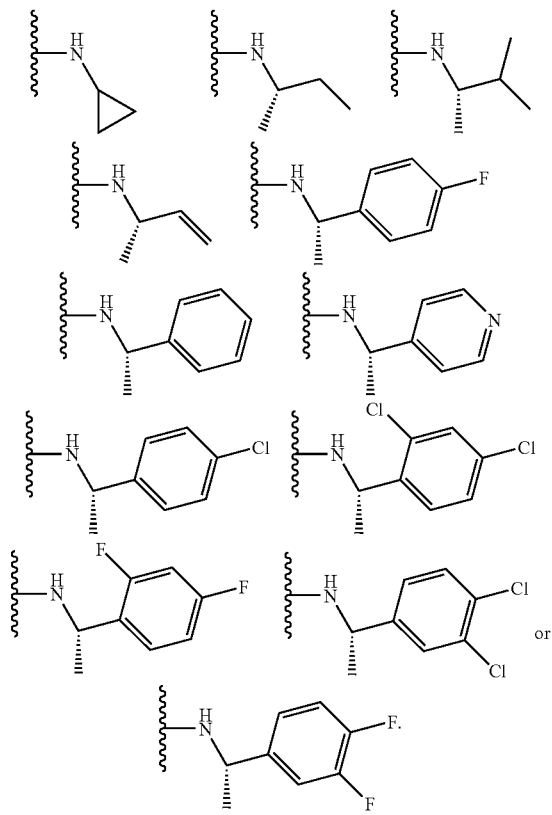

According to a preferred embodiment of formula (II), W is:

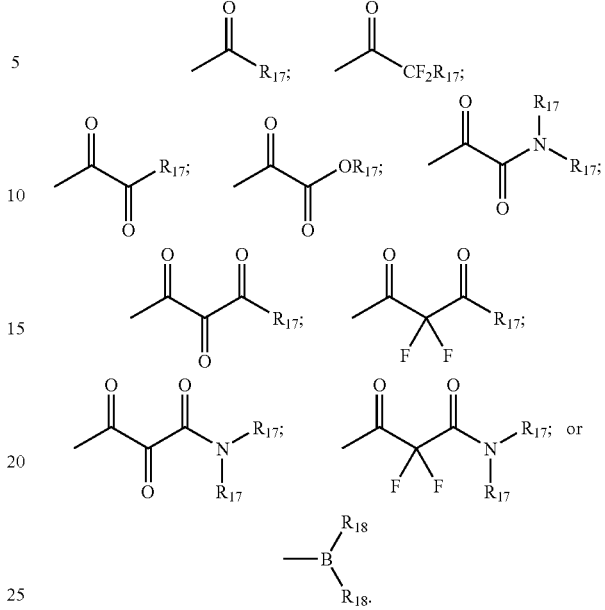

More preferred embodiments of W are as follows:

W is:

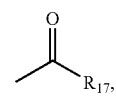

wherein $R_{17}$ is hydrogen or C5-heteroaryl, or C9-heteroaryl, wherein $R_{17}$ has up to 3 substituents selected from J.

W is:

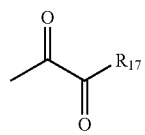

wherein $R_{17}$ is hydrogen, (C1–C6)-alkyl, (C6–C10)-aryl, or C3–C6-cycloalkyl-(C1–C3)-alkyl, wherein the cycloalkyl is preferably a cyclopropyl group. The aryl group is optionally substituted with up to 3 J groups, wherein J is halogen, preferably chloro or fluoro.

W is:

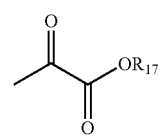

wherein $R_{17}$ is hydrogen or (C1–C6)-alkyl.

W is:

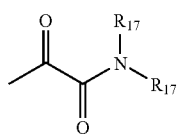

wherein $R_{17}$ is hydrogen, (C1–C6)-alkyl, (C1–C6)-alkenyl, (C6–C10)-aryl-(C1–C6)-alkyl-, or (C6–C10)-heteroaryl-(C1–C6)-alkyl-, wherein $R_{17}$ is optionally substituted with up to 3 J groups. Preferred J substituents on the alkyl and aryl groups are halogen, carboxy, and heteroaryl. More preferred substituents on the aryl groups are halogen (preferably chloro or fluoro) and more preferred J substituents on the alkyl groups are carboxy and heteroaryl.

According to yet other preferred embodiments of formula (II), W is:

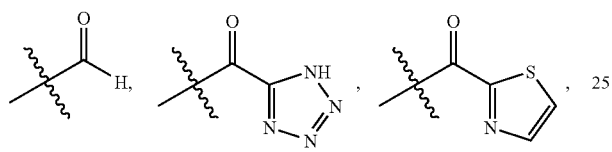

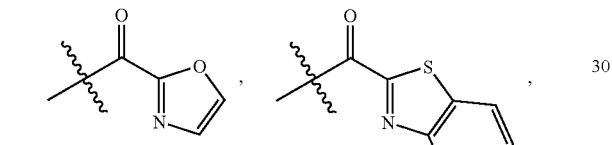

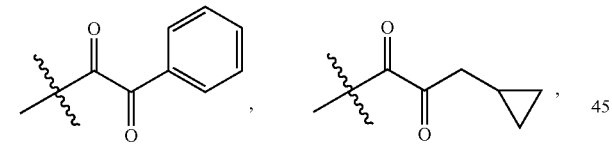

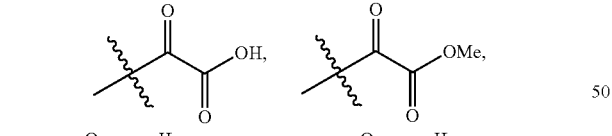

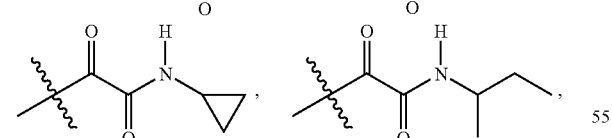

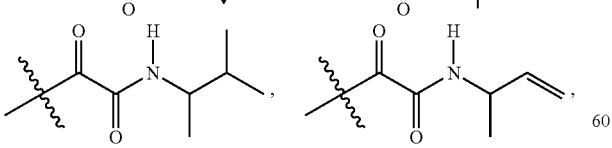

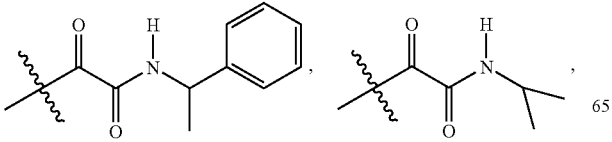

-continued

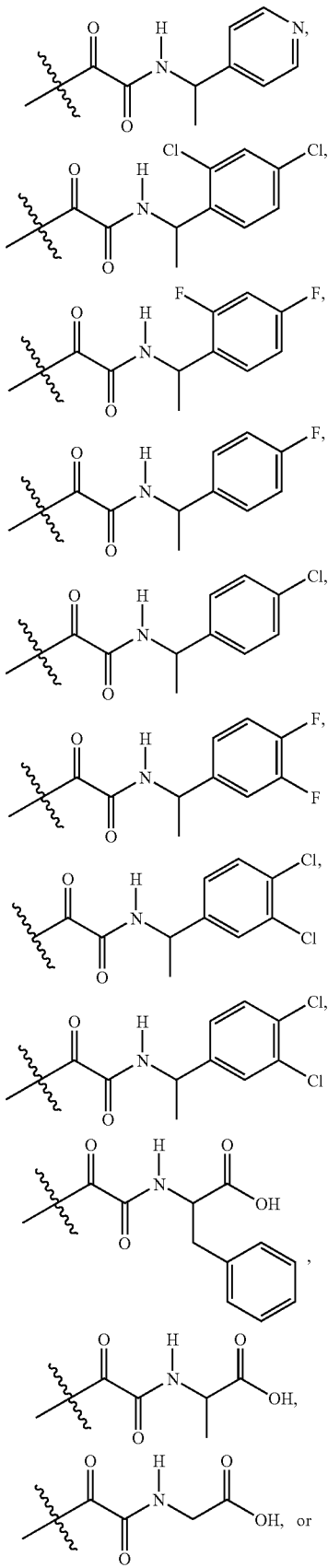

-continued

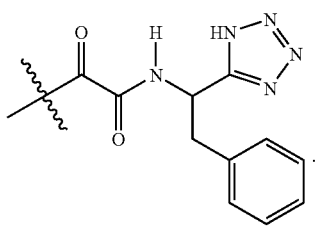

According to a preferred embodiment, each $R_{18}$ together with the boron atom, is a (C5–C7)-membered heterocyclic ring having no additional heteroatoms other than the boron and the two oxygen atoms. Preferred groups are selected from:

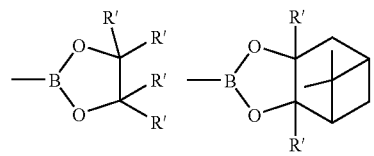

wherein R' is, preferably, (C1–C6)-alkyl) and is, most preferably, methyl.

According to a preferred embodiment, $R_1$ is selected from:

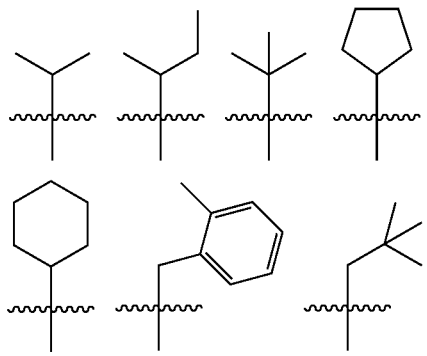

According to a preferred embodiment, $R_3$ is selected from:

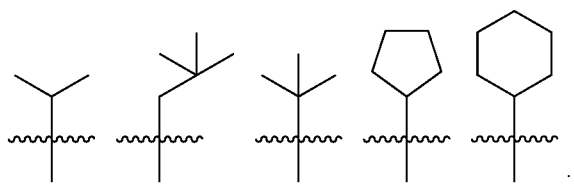

According to a preferred embodiment, $R_3$ is:

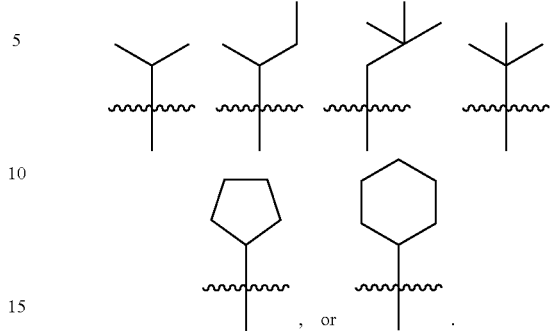

, or .

According to a preferred embodiment, $R_5$ is:

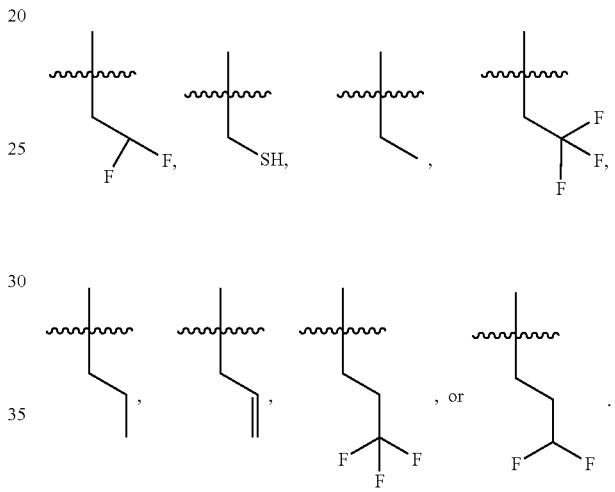

, or .

According to a preferred embodiment, $R_5$ is selected from:

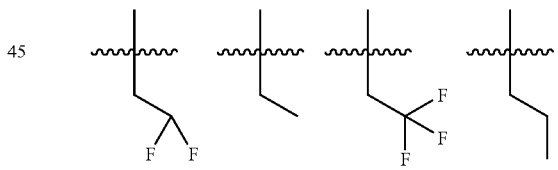

According to a preferred embodiment, $R_{5'}$ is hydrogen and $R_5$ is other than hydrogen.

According to a preferred embodiment, $R_2$ and $R_4$ are each independently selected from H, methyl, ethyl or propyl.

According to a preferred embodiment, V is —C(O)—$NR_8$—. More preferably, V is —C(O)—NH—.

According to a preferred embodiment, J is halogen —OR', —$NO_2$, —$CF_3$, —$OCF_3$, —R', oxo, 1,2-methylenedioxy, —N(R')$_2$, —SR', —SOR', —$SO_2$R', —C(O)R', —COOR'—CON(R')$_2$, —N(R')COR', —N(COR')COR', —CN, or —$SO_2$N(R')$_2$.

According to a preferred embodiment, $J_2$ is halogen, —OR', —$NO_2$, —$CF_3$, —$OCF_3$, —R', oxo, 1,2-methylenedioxy, —N(R')$_2$, —SR', —SOR', —$SO_2$R', —C(O)R', —COOR'—CON(R')$_2$, —N(R')COR', —N(COR')COR', —CN, or —$SO_2$N(R')$_2$.

In J and $J_2$ the halogen is preferably chloro or fluoro. More preferably, the halogen is fluoro.

According to a preferred embodiment of formula (II), $X_1$ is —N($R_{20}$)—, —O—, or —C(R')$_2$—. More preferably, $X_1$ is —N($R_{20}$)—.

According to a preferred embodiment of formula (II), $X_2$ is —C(O)—.

According to a preferred embodiment of formula (II), $R_2$, $R_4$, and $R_{20}$, are each independently selected from H or (C1–C3)-alkyl-. More preferably, each of $R_2$, $R_4$, and $R_{20}$, are H.

According to a preferred embodiment of formula (II), $R_{14}$ is —H, —S(O)R', —S(O)$_2$R', —C(O)R', —C(O)OR', —C(O)N(R')$_2$, —N(R')C(O)R', —N(COR')COR', or —SO$_2$N(R')$_2$. More preferably, $R_{14}$ is hydrogen.

According to a preferred embodiment of formula (II), $R_{15}$ and $R_{16}$ are independently halogen, —OR', —NO$_2$, —CF$_3$, —OCF$_3$, —R', oxo, 1,2-methylenedioxy, —N(R')$_2$, —SR', —SOR', —SO$_2$R', —C(O)R', —COOR'—CON(R')$_2$, —N(R')COR', —N(COR')COR', —CN, or —SO$_2$N(R')$_2$. More preferably, $R_{15}$ and $R_{16}$ are independently (C1–C6)-alkyl-. Even more preferably, each $R_{15}$ and $R_{16}$ is methyl.

According to a preferred embodiment of formula (II), Z is O and $R_{19}$ is: (C1–C6)-alkyl-(C3–C10)-cycloalkyl-, [(C3–C10)-cycloalkyl]-(C1–C12)-aliphatic-, (C6–C10)-aryl-, (C6–C10)-aryl-(C1–C6)alkyl, (C3–C10)-heterocyclyl, (C6–C10)-heterocyclyl-(C1–C6)alkyl, (C5–C10)-heteroaryl, or (C5–C10)-heteroaryl-(C1–C6)-alkyl; wherein $R_{19}$ has up to 3 substituents selected independently from $J_2$; and wherein up to 3 aliphatic carbon atoms in $R_{19}$ may be replaced by a heteroatom selected from O, NH, S, SO$_1$ or SO$_2$ in a chemically stable arrangement. More preferably, $R_{19}$ is (C1–C6)-alkyl-. Most preferably, $R_{19}$ is methyl.

According to a preferred embodiment of formula (II), $R_{14}$ is H; $Z_2$ is CH$_2$; or $R_{19}$ is:

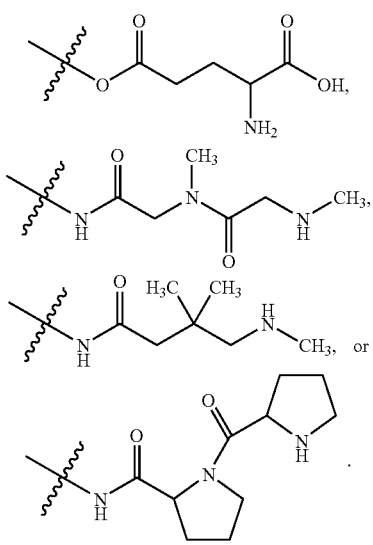

More preferably, $R_{14}$ is H; $Z_2$ is CH$_2$; and $R_{19}$ is as depicted immediately above.

According to another preferred embodiment of formula (II), each $R_{19}$ is methyl; $Z_2$ is O; or $R_{14}$ is:

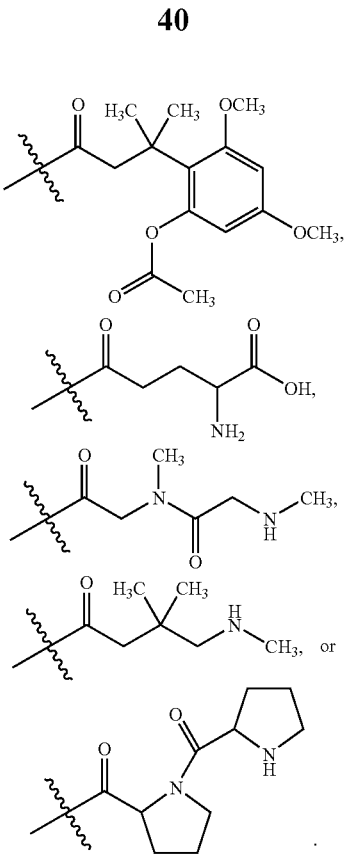

More preferably, each $R_{19}$ is methyl; $Z_2$ is O; and $R_{14}$ is as depicted immediately above. Even more preferably $R_{14}$ is:

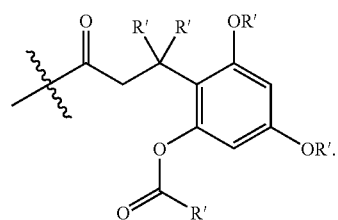

In this embodiment, R' is, preferably, (C1–C6)alkyl.

According to another preferred embodiment of formula (II), $Z_2$ is:

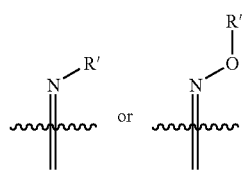

More preferably, each $R_{19}$ is methyl; $R_{14}$ is H; and $Z_2$ is as depicted immediately above.

According to another preferred embodiment of formula (II), $Z_2$ is:

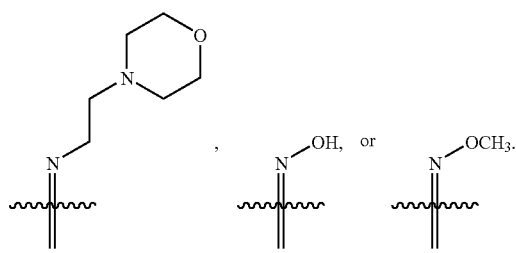

According to a preferred embodiment of formula (II), $R_{1'}$ is H.

According to a preferred embodiment of formula (II), $R_{13'}$ is H.

According to a preferred embodiment of formula (II), $R_{11'}$ is H.

According to a preferred embodiment of formula (II), $R_{12}$ is H.

According to a preferred embodiment of formula (II), $R_{12}$ is: (C1–C6)-alkyl-, (C3–C10)-cycloalkyl, [(C3–C10)-cycloalkyl]-(C1–C12)-alkyl-, (C6–C10)-aryl-, (C6–C10)-aryl-(C1–C6)alkyl-, (C3–C10)-heterocyclyl-, (C6–C10)-heterocyclyl-(C1–C6)alkyl-, (C5–C10)-heteroaryl-, or (C5–C10)-heteroaryl-(C1–C6)-alkyl-. More preferably, $R_{12}$ is isobutyl, cyclohexyl, cyclohexylmethyl, benzyl, or phenylethyl. Even more preferably, $R_{11}$ is H.

According to a preferred embodiment of formula (II), $R_{11}$ is (C1–C6)-alkyl-, (C3–C10)-cycloalkyl, [(C3–C10)-cycloalkyl]-(C1–C12)-alkyl-,(C6–C10)-aryl-, (C6–C10)-aryl-(C1–C6)alkyl-; (C3–C10)-heterocyclyl-, (C6–C10)-heterocyclyl-(C1–C6)alkyl-, (C5–C10)-heteroaryl-, or (C5–C10)-heteroaryl-(C1–C6)-alkyl-. More preferably, $R_{11}$ is (C1–C6)-alkyl-, (C3–C10)-cycloalkyl, [(C3–C10)-cycloalkyl]-(C1–C12)-alkyl-, (C6–C10)-aryl-(C1–C6)alkyl-; (C6–C10)-heterocyclyl-(C1–C6)alkyl-, or (C5–C10)-heteroaryl-(C1–C6)-alkyl-. Even more preferably, $R_{11'}$ and $R_{12}$ are H.

According to a preferred embodiment of formula (II), the

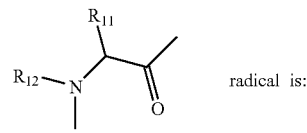

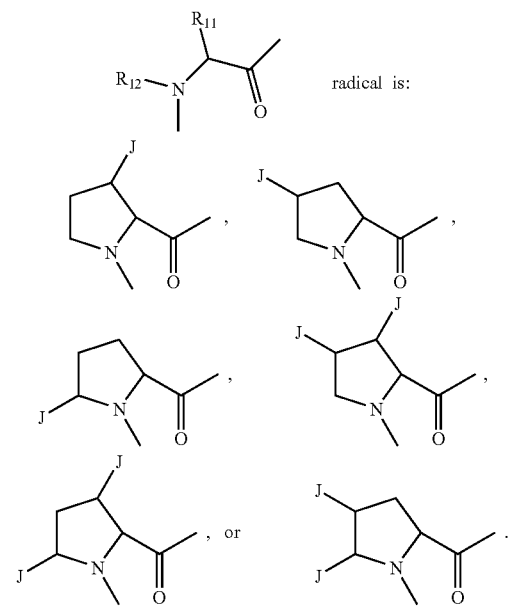

More preferably, the radical is:

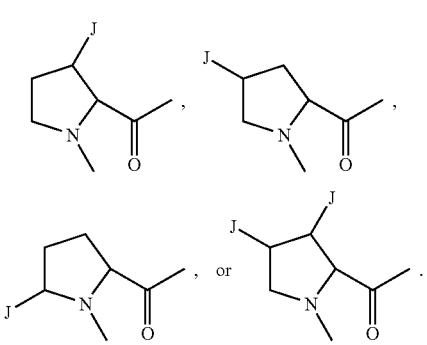

According to a preferred embodiment of formula (II), the

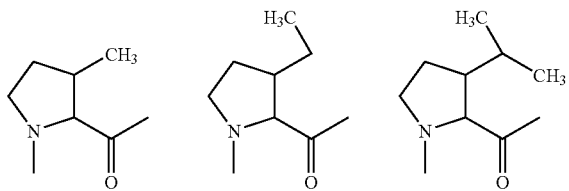

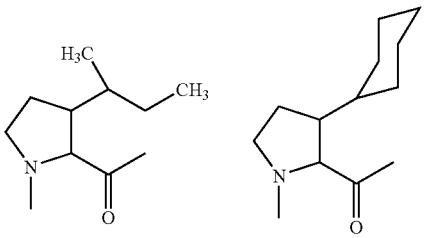

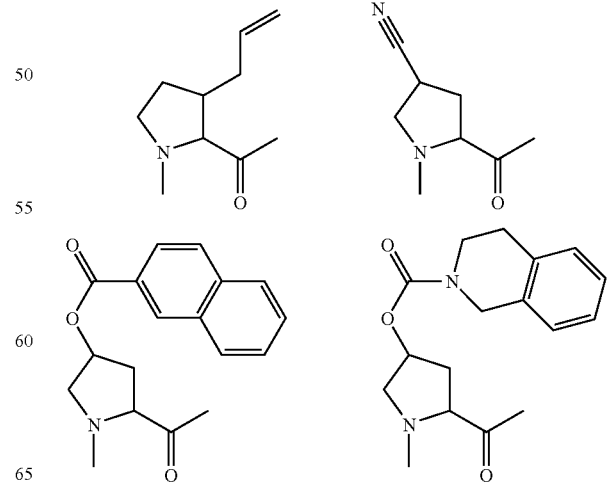

-continued
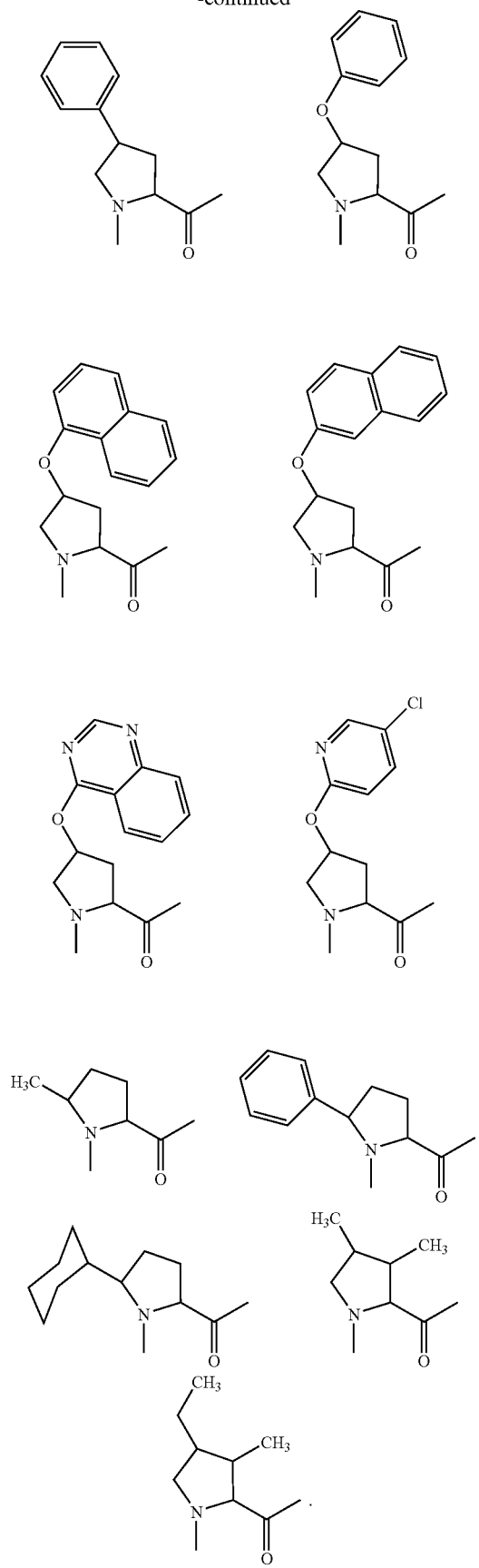
Alternatively, this radical is:
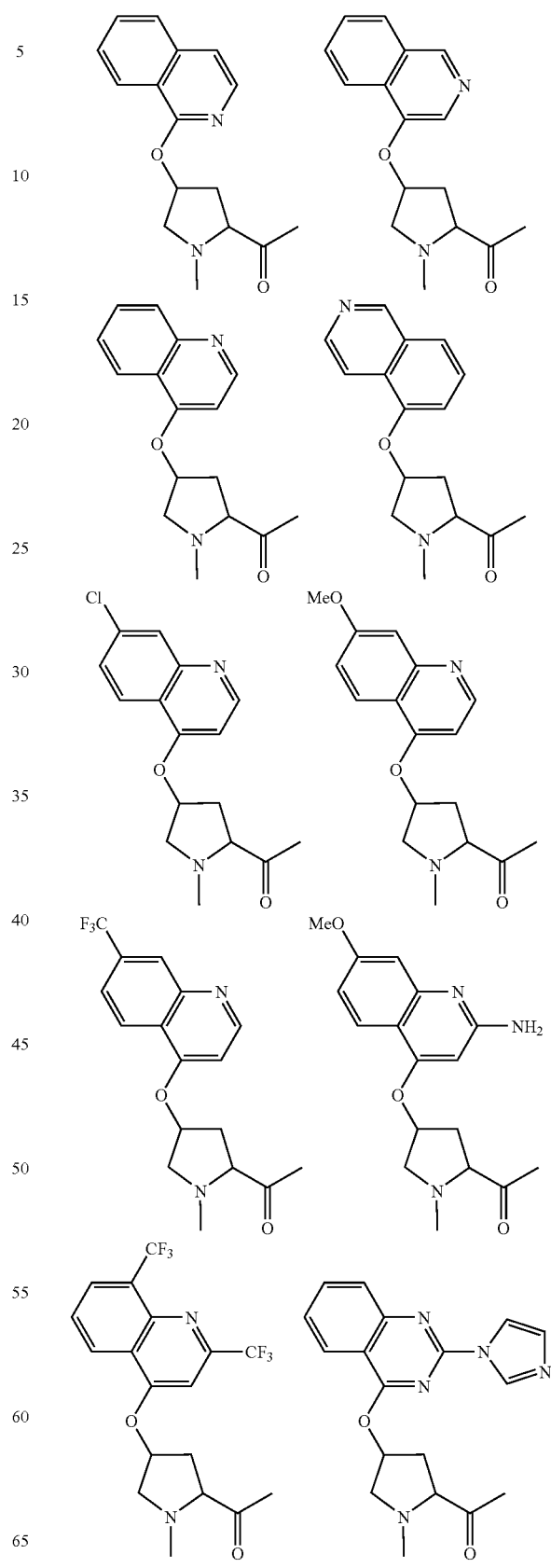

-continued

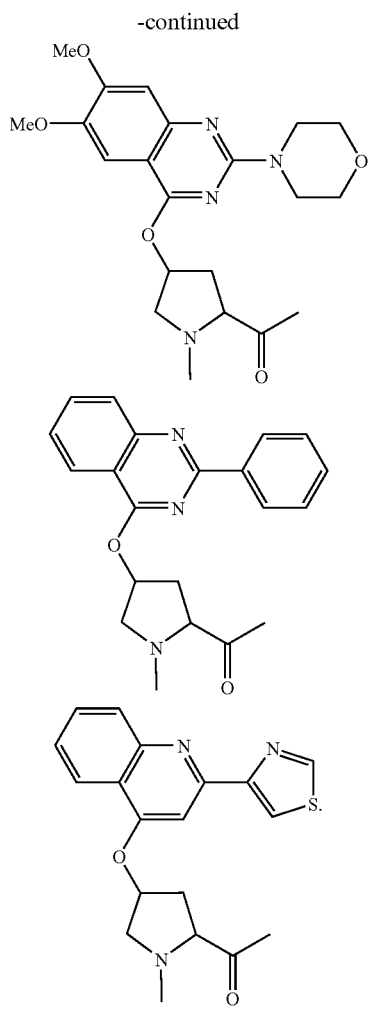

According to a preferred embodiment of formula (II), the

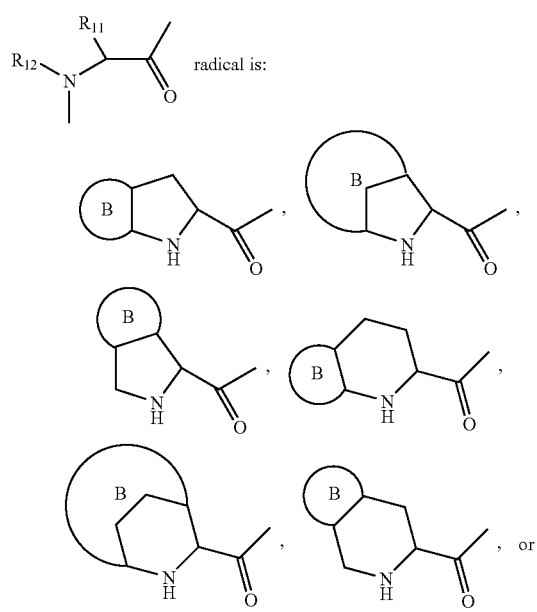

-continued

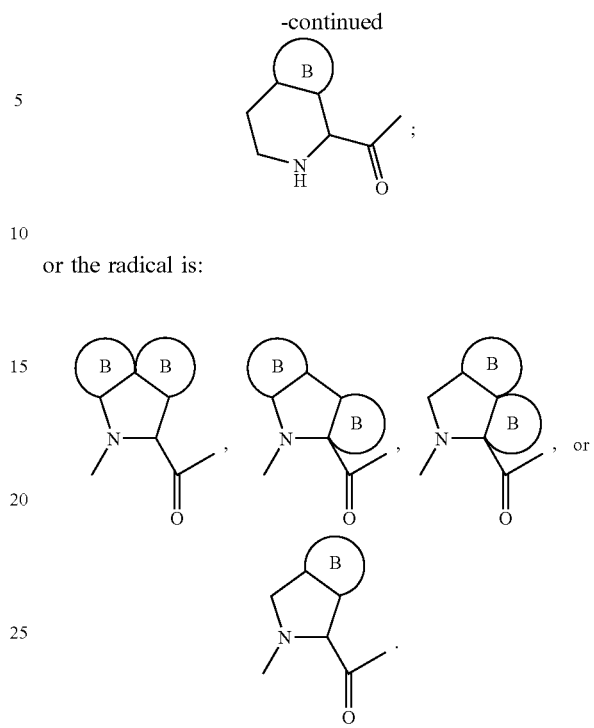

or the radical is:

wherein each B independently forms a 3- to a 20-membered carbocyclic or heterocyclic ring system;
wherein each ring B is either aromatic or nonaromatic;
wherein each heteroatom in the heterocyclic ring system is N, NH, O, S, SO, or $SO_2$;
wherein each ring is optionally fused to a (C6–C10)aryl, (C5–C10)heteroaryl, (C3–C10)cycloalkyl, or (C3–C10)heterocyclyl; and
wherein each ring has up to 3 substituents selected independently from J.

In the embodiment immediately above, a preferred ring systems is:

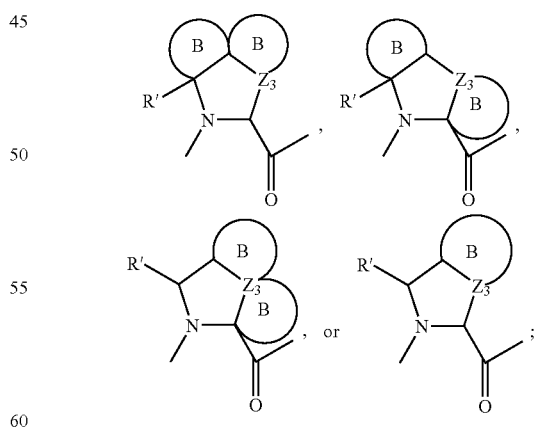

wherein $Z_3$ is a carbon atom, —CHR'—N—, —HN—CR'— or —CHR'—CHR'—, —O—CHR'—, —S—CHR'—, —SO—CHR'—, —$SO_2$—CHR'—, or —N—. R' is, preferably, (C1–C12)-aliphatic, (C6–C10)-aryl, (C6–C10)aryl-(C1–C12)-aliphatic, or (C3–C10)-cycloalkyl. The aliphatic is, more preferably, a (C1–C6)-alkyl and the cycloalkyl is more preferably, a (C3–C7)-cycloalkyl. These ring systems are described more fully below.
Preferred embodiments of ring systems 1, 2, 3, and 4, are described below; ring systems 1, 2, 3, and 4, are respectively:
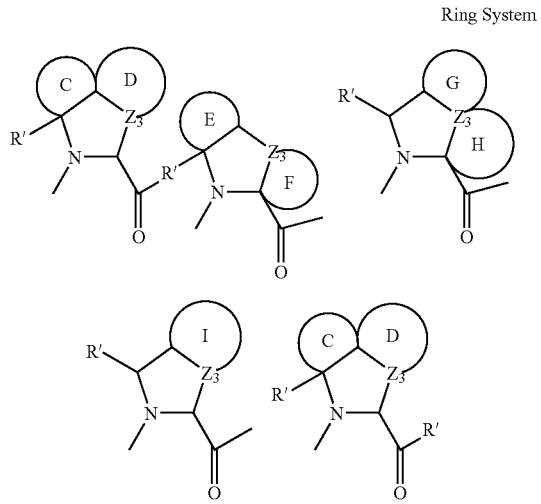
Ring System 1
In ring system 1, ring C is preferably selected from:
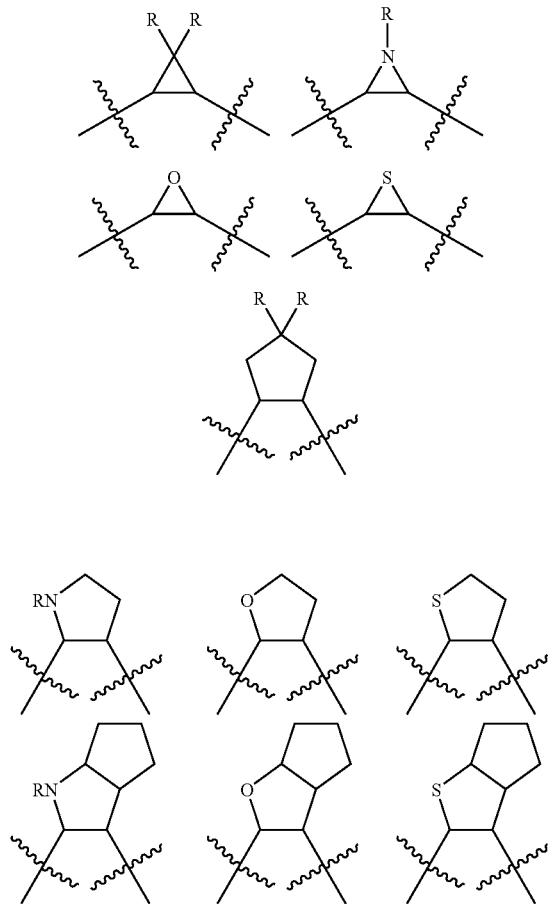
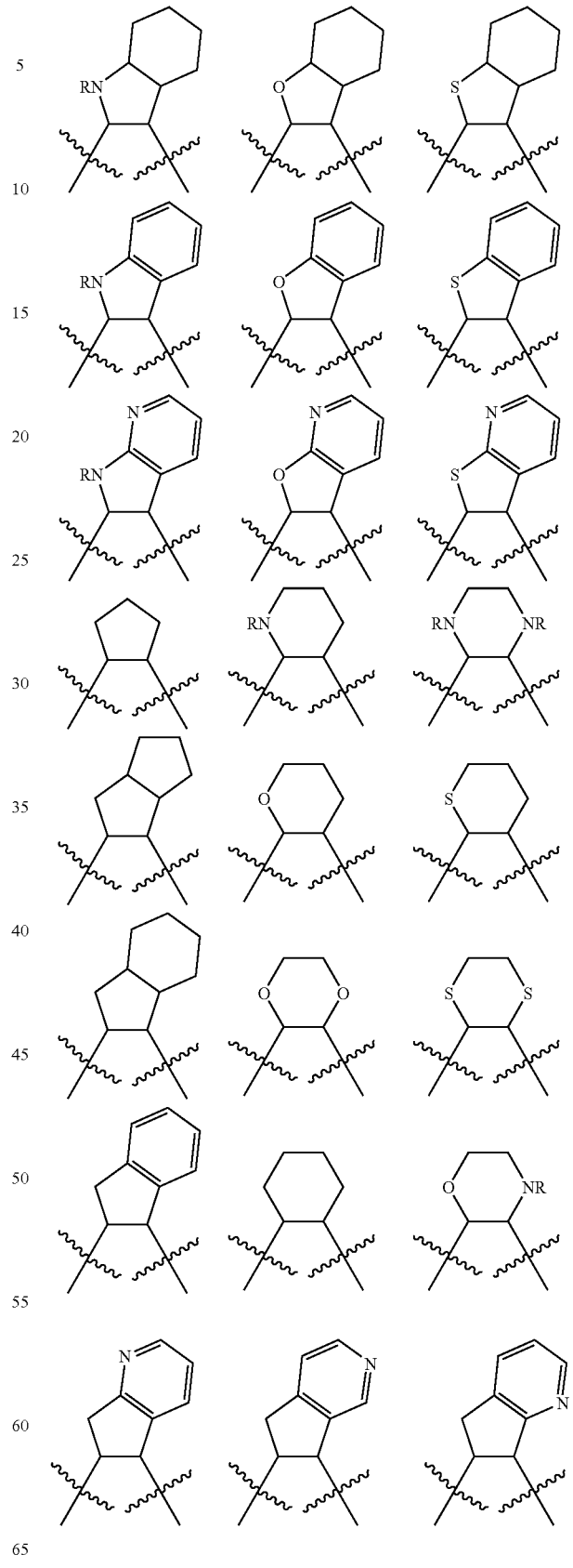
wherein R is aliphatic, aryl, aralkyl or cycloalkyl.

More preferably, ring C is selected from:
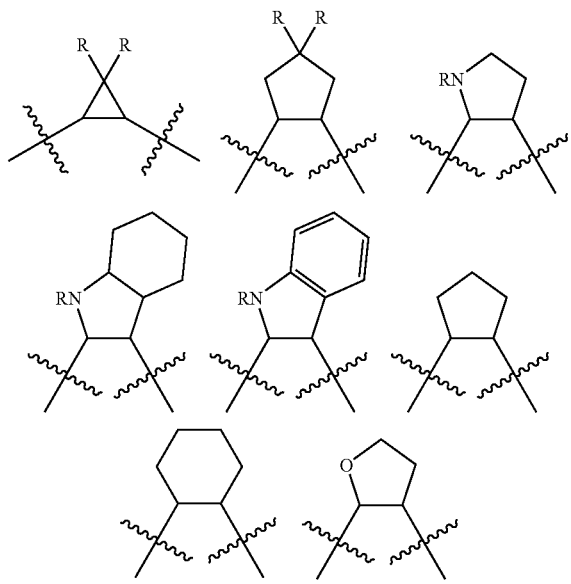
Ring D is preferably selected from:
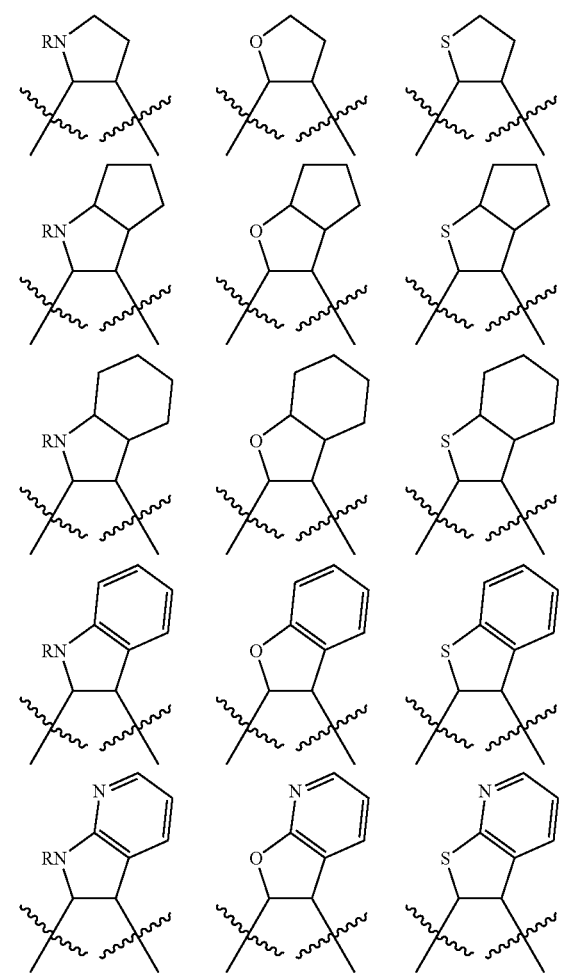
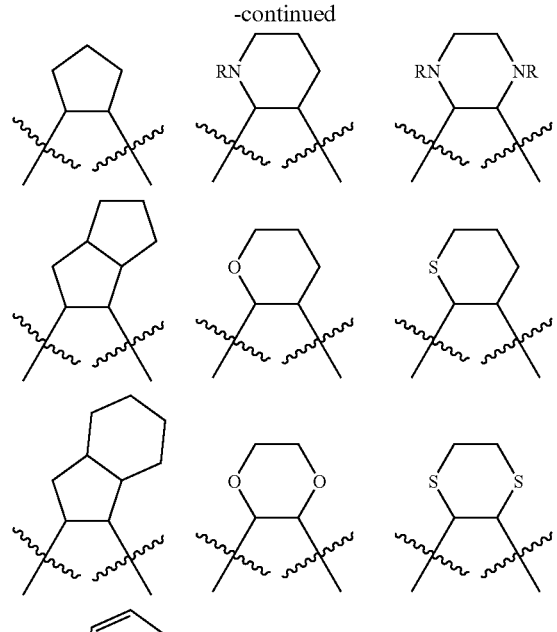

-continued
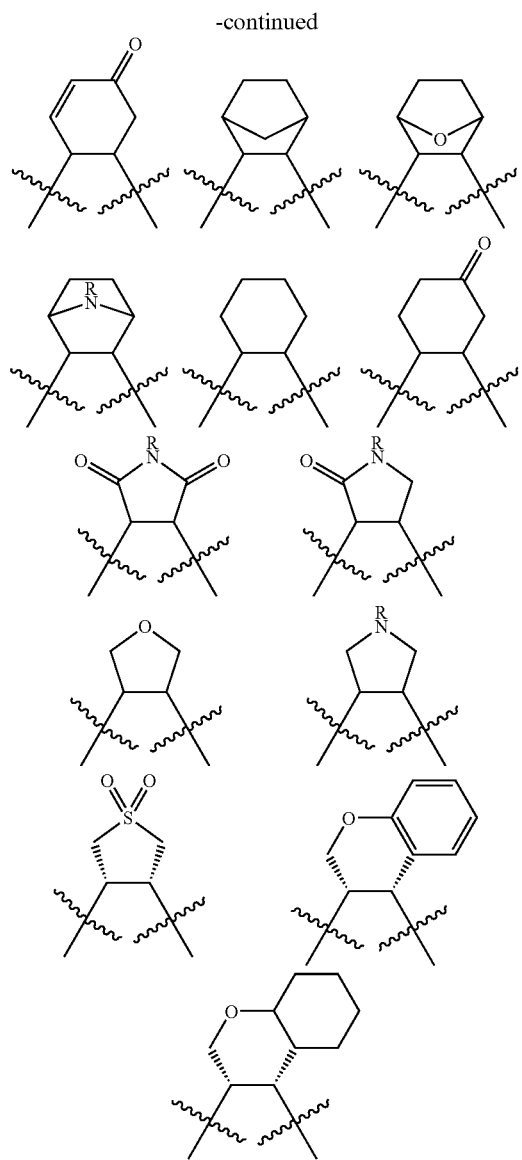
wherein R is aliphatic, aryl, aralkyl or cycloalkyl.
More preferably, ring D is selected from:
-continued
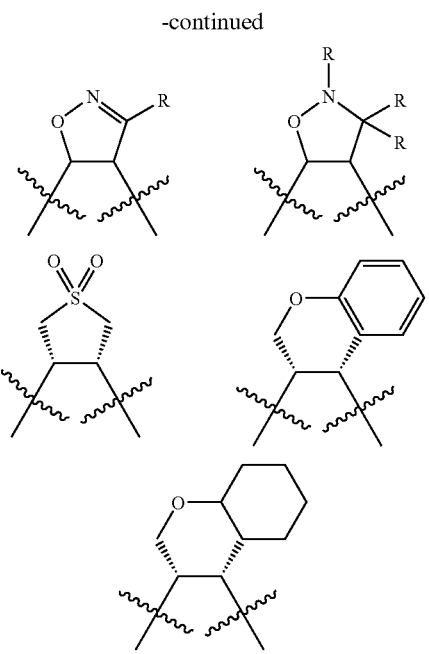
According to another preferred embodiment, ring system 1 is selected from the group:
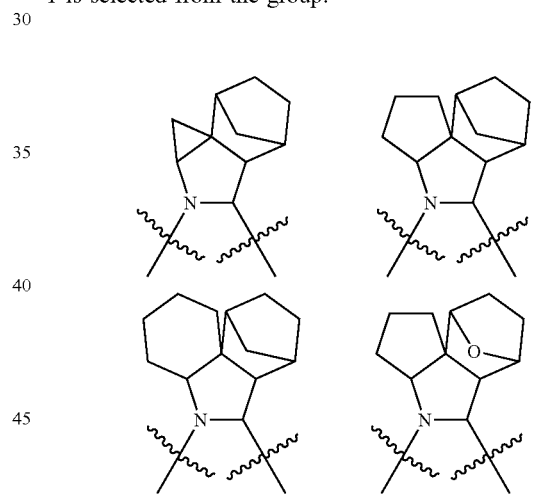
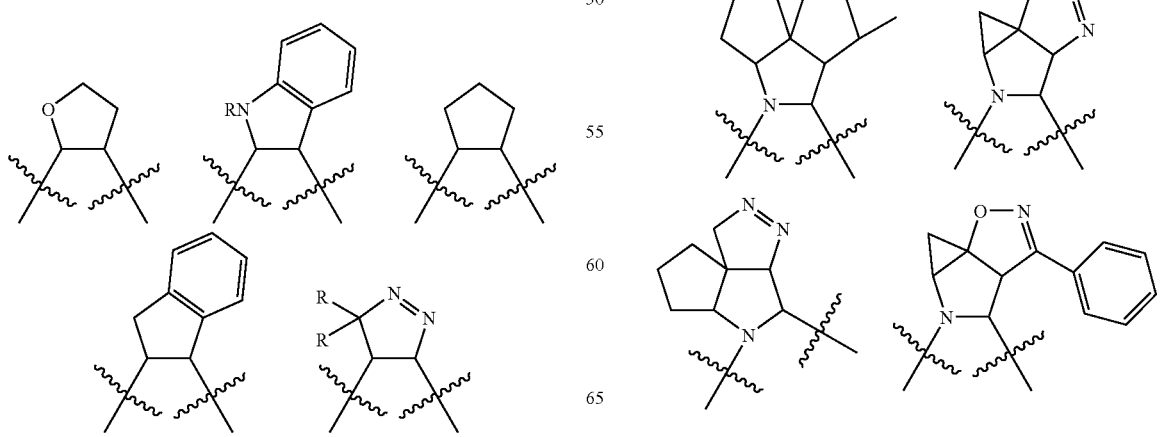

-continued

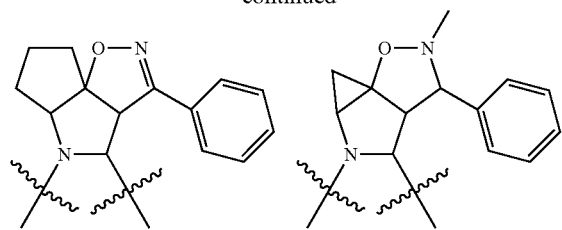

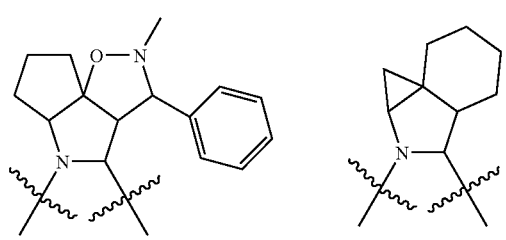

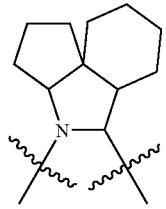

Ring System 2

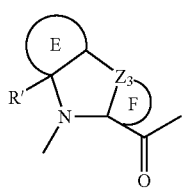

In ring system 2, ring F is preferably selected from:

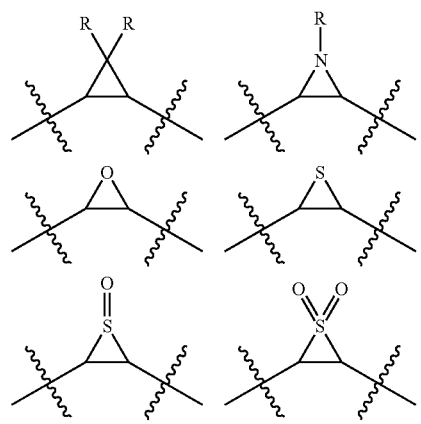

Ring system 2 is preferably selected from:

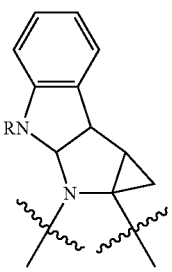
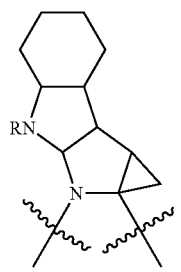

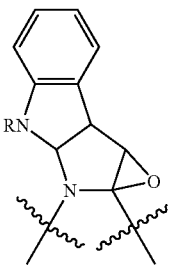
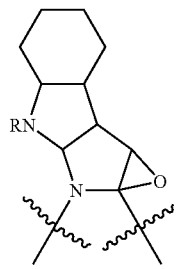

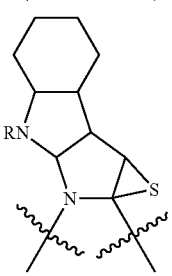
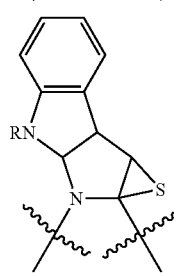

Ring System 3

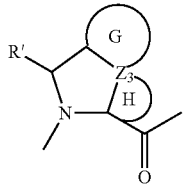

In ring system 3, preferred embodiments of ring G are as defined above for preferred embodiments of ring D. Preferred embodiments of ring H are as defined above for preferred embodiments of ring F.

Ring System 4

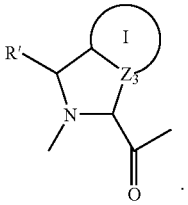

According to a preferred embodiment of ring system 3, ring I is a bridged bicyclic ring system containing 6–12 carbon atoms, wherein ring I is saturated or partially unsaturated, and ring I has up to 3 substituents selected independently from J.

Preferred embodiments of ring I are selected from:
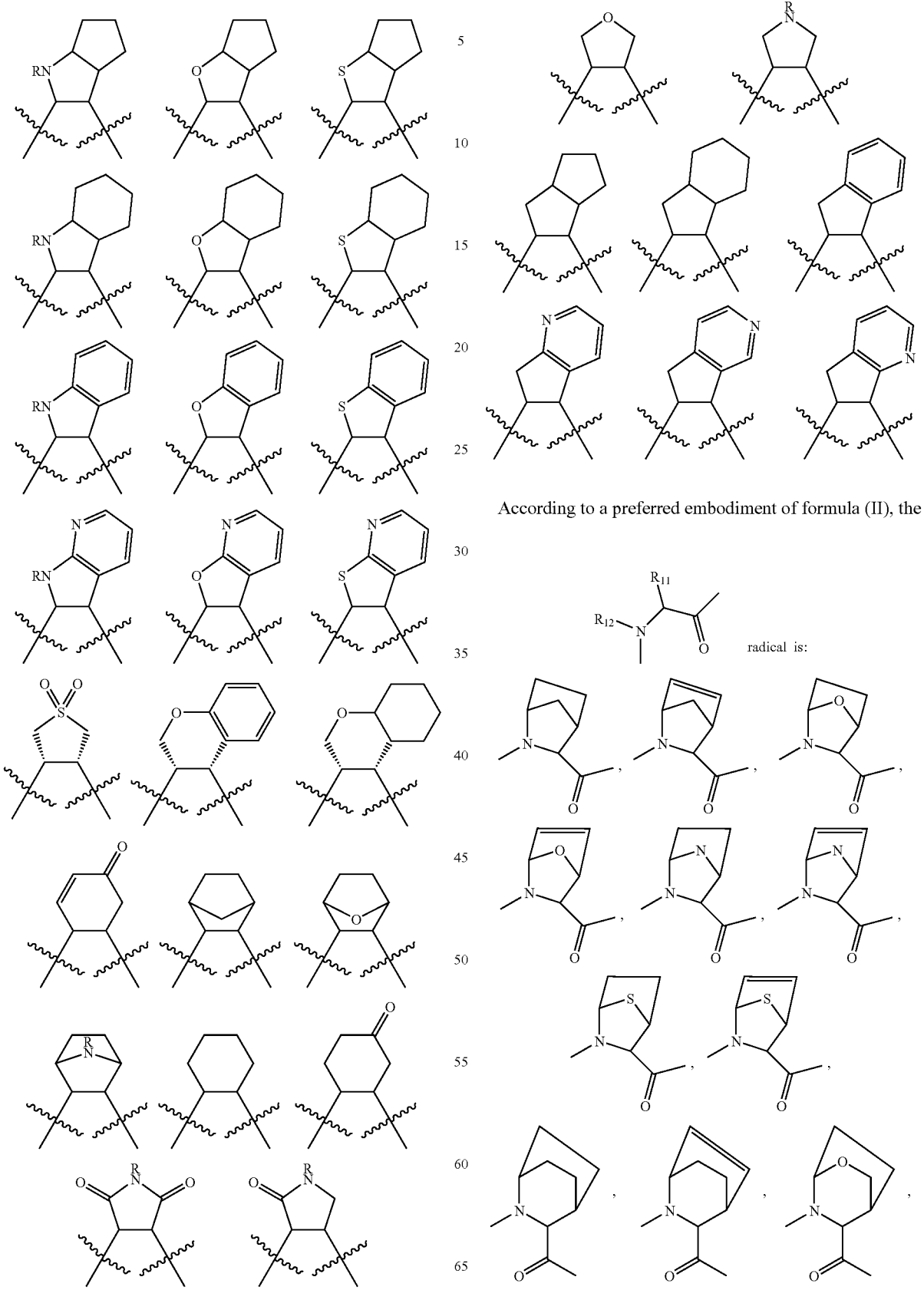
According to a preferred embodiment of formula (II), the
$R_{12}\diagdown N \diagup \overset{R_{11}}{\underset{\phantom{O}}{C}} \diagdown \overset{}{\underset{O}{C}} \diagdown$ radical is:

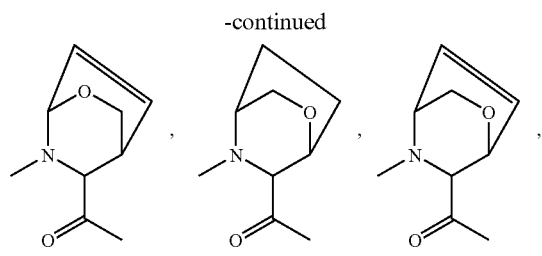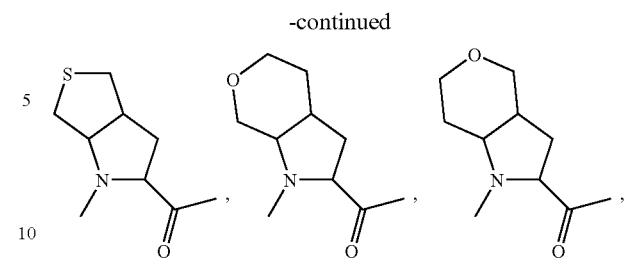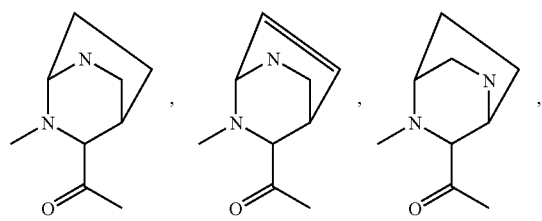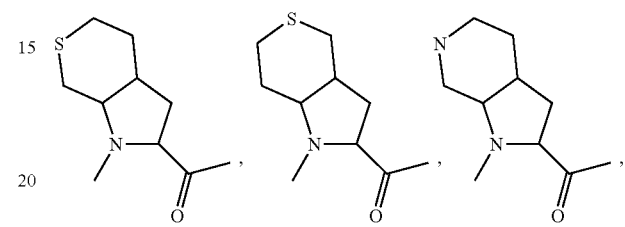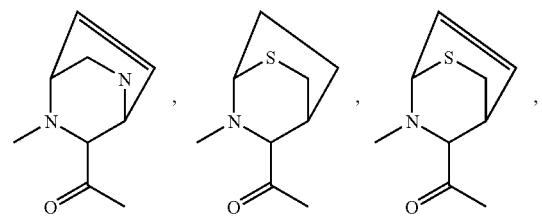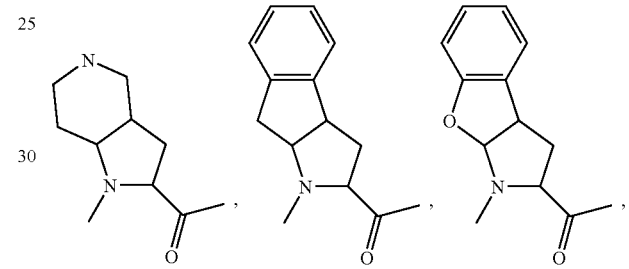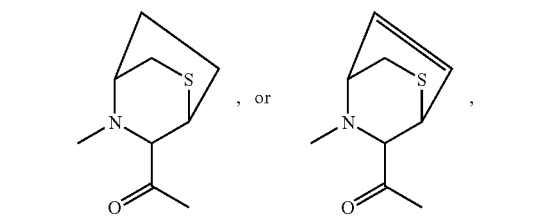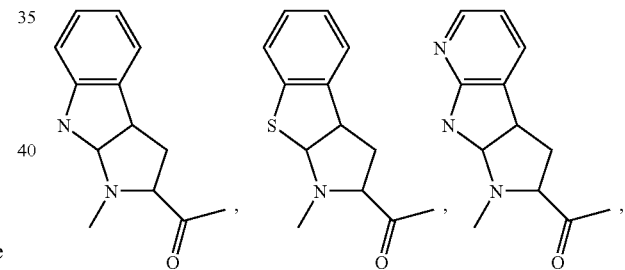
According to a preferred embodiment of formula (II), the
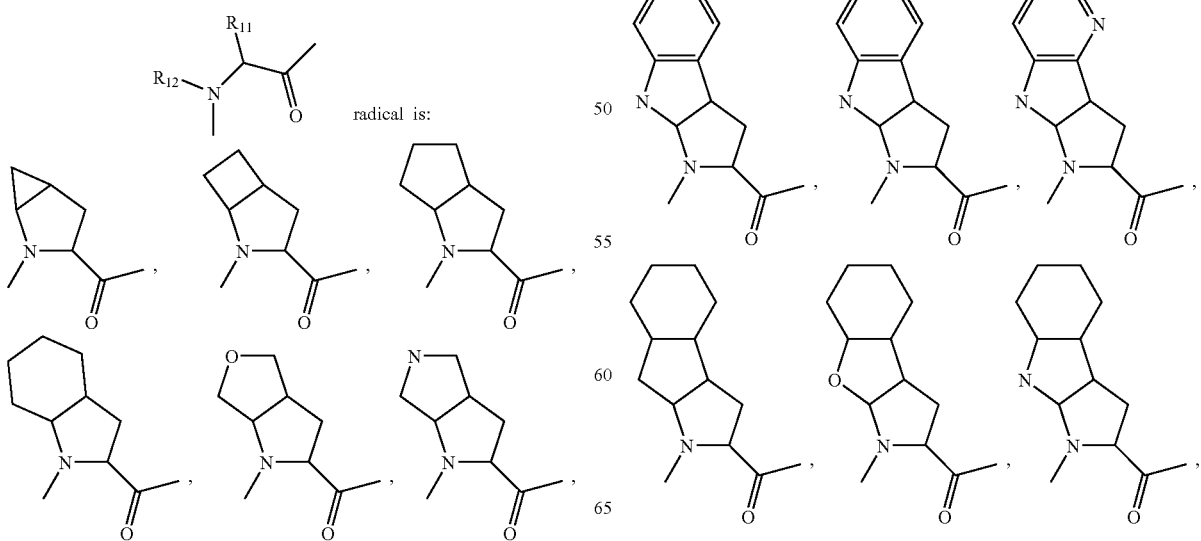
radical is:

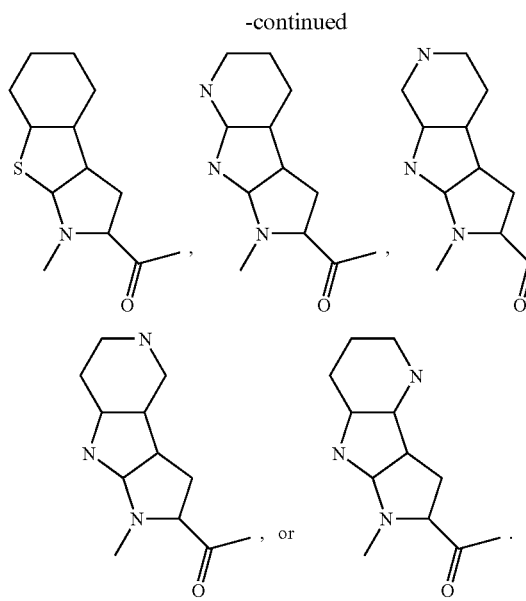
According to a preferred embodiment of formula (II), the radical is:
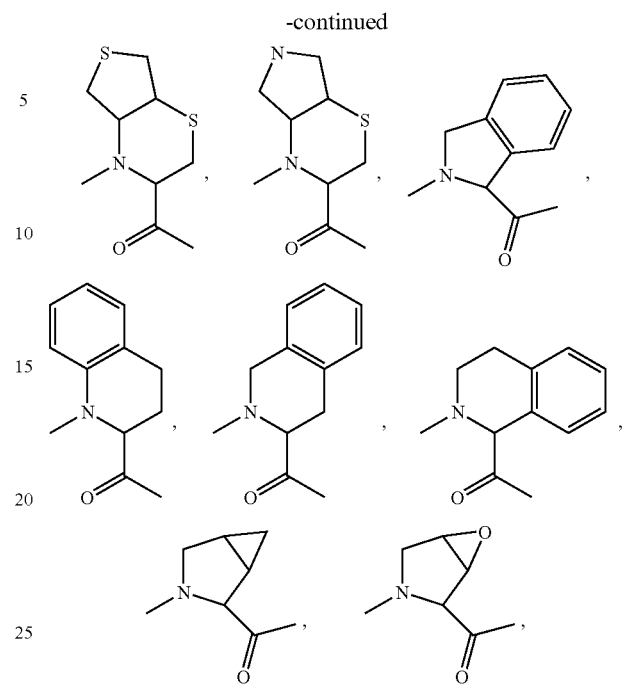
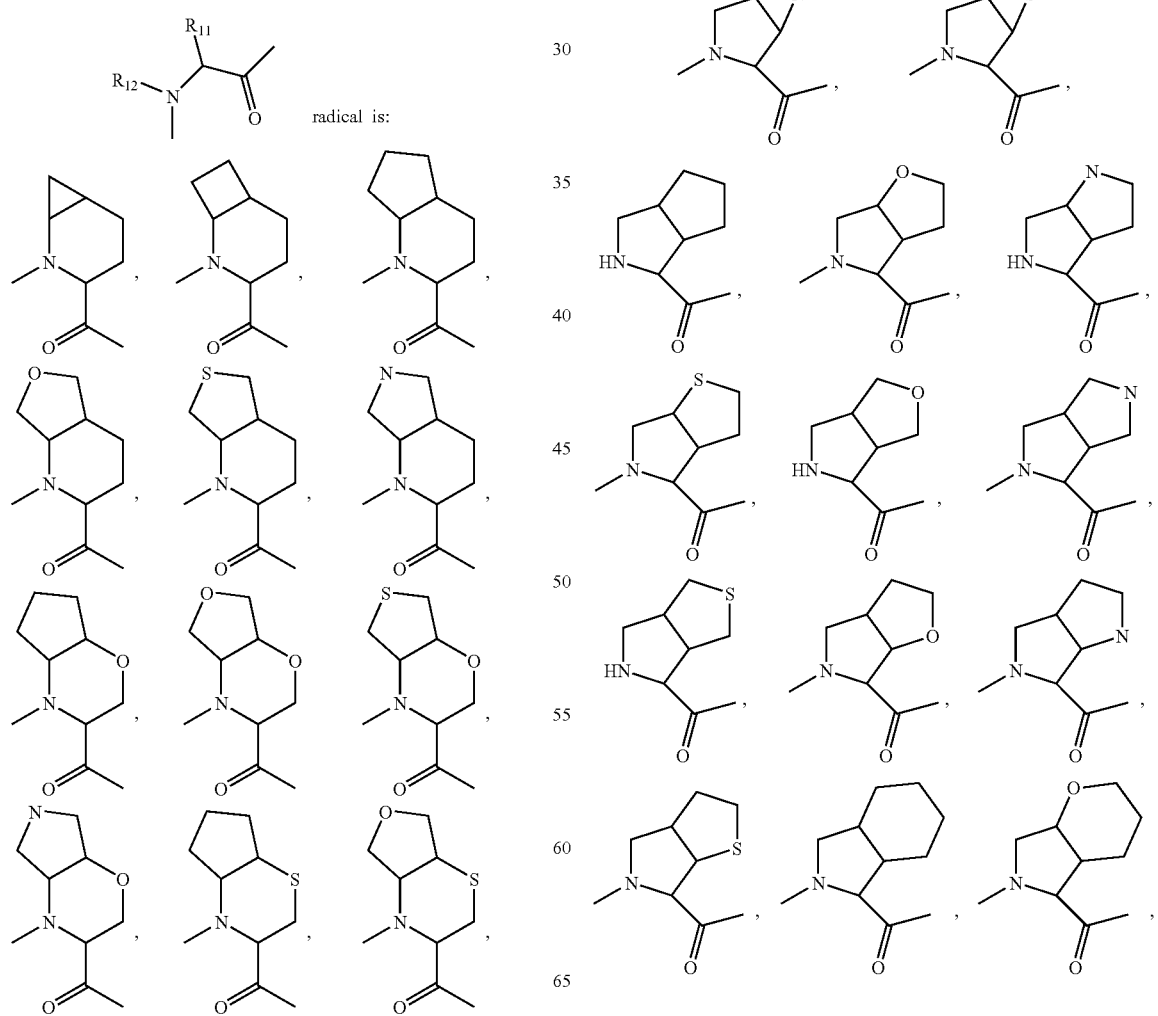

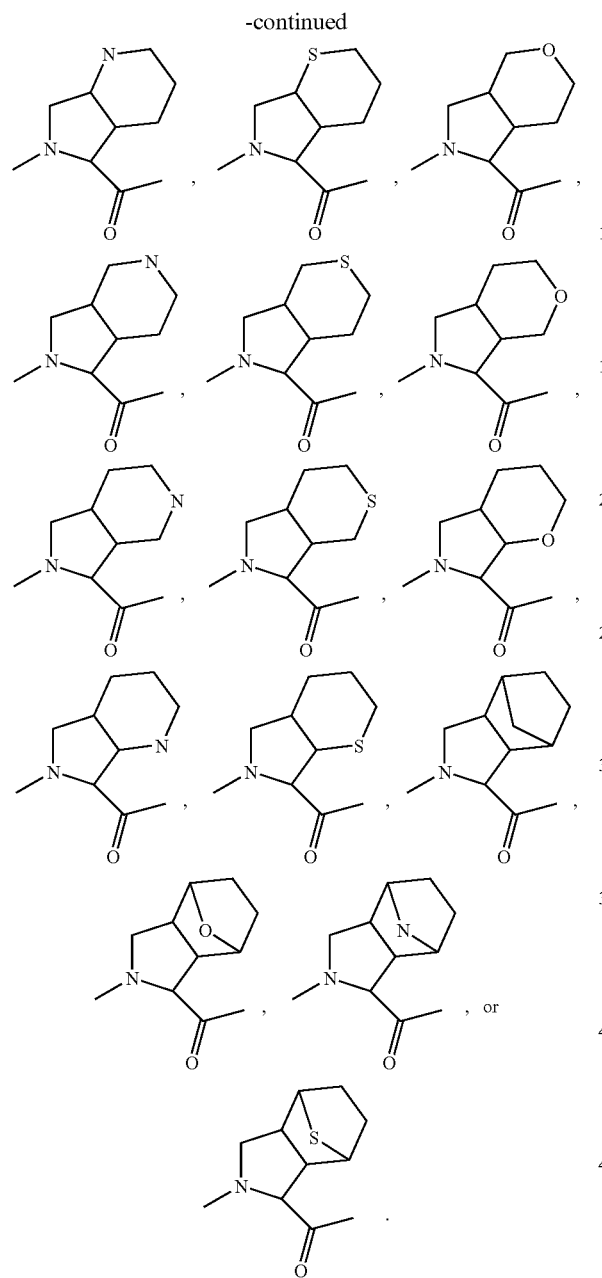
According to a preferred embodiment of formula (II), the
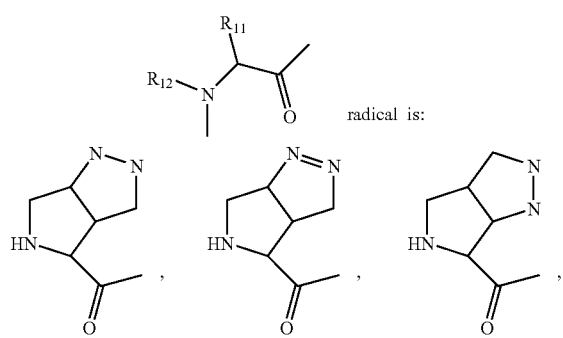
radical is:
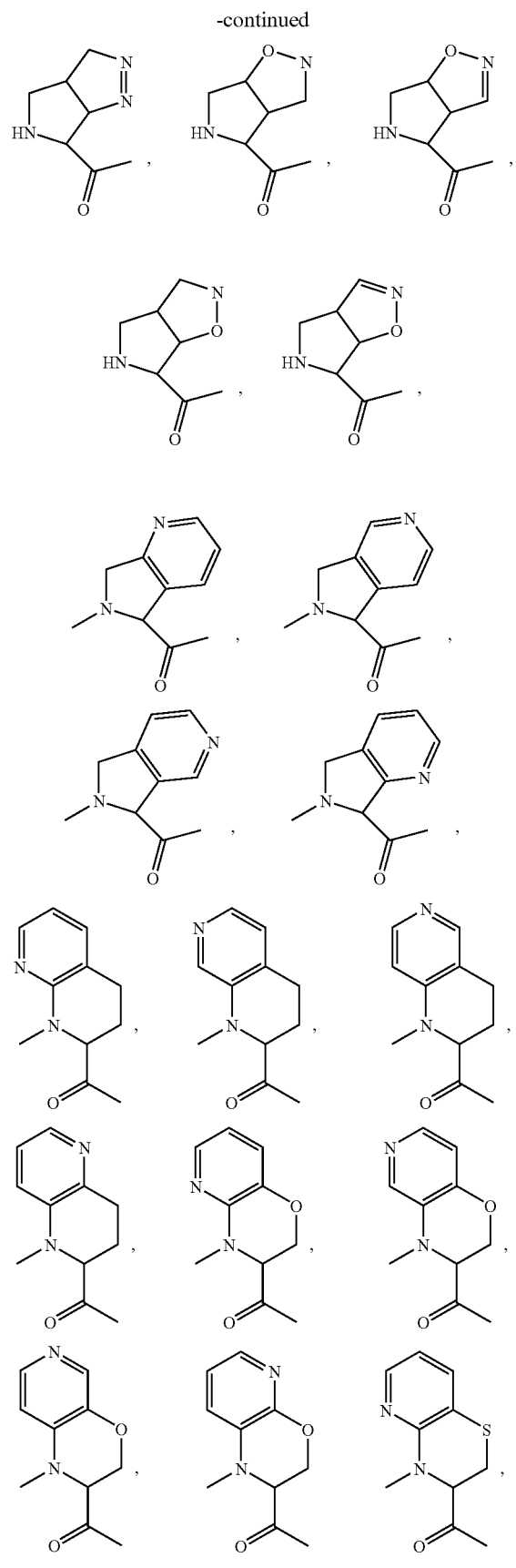

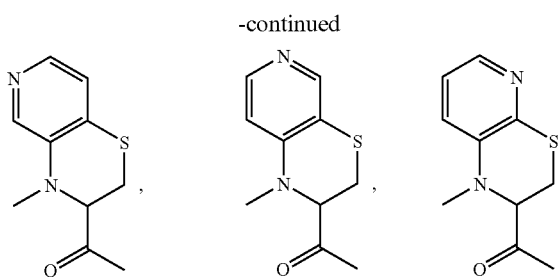
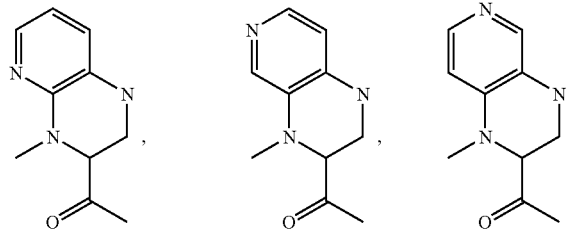
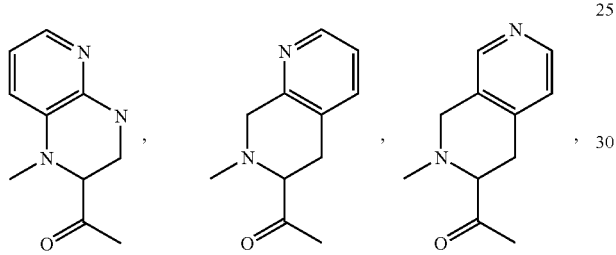
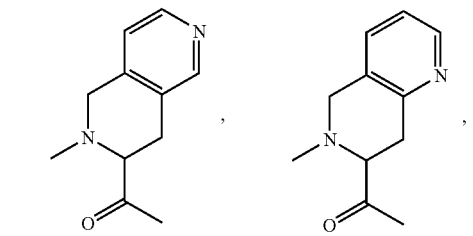
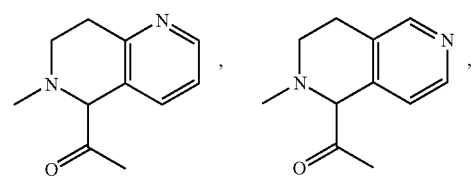
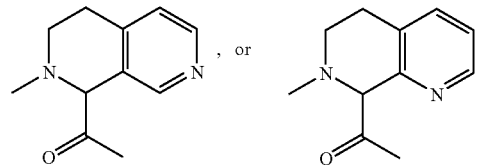
According to a preferred embodiment of formula (II), the
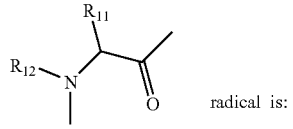 radical is:
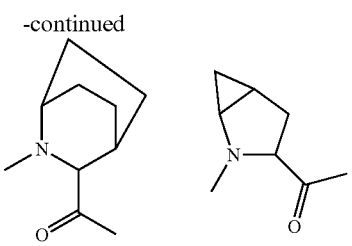
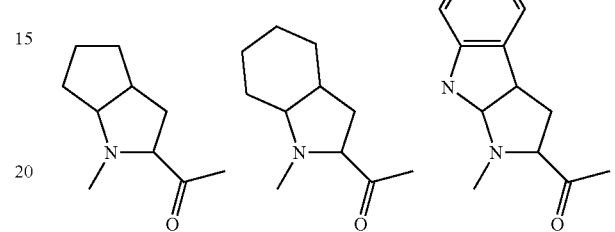
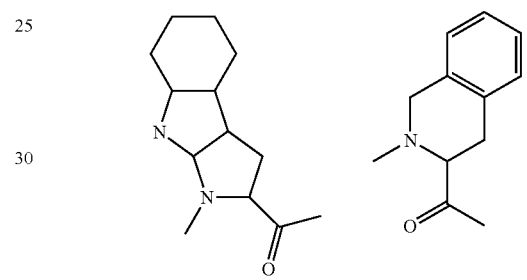
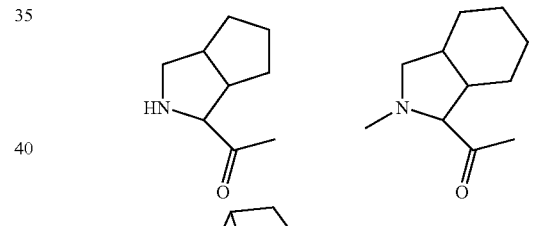
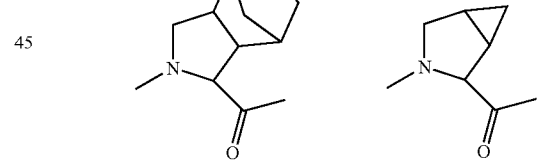
According to a preferred embodiment of formula (II), the
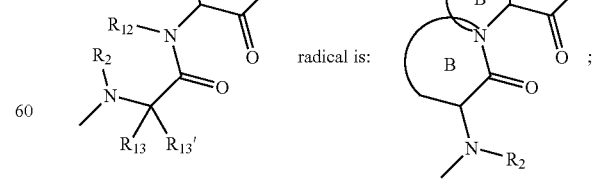 radical is: 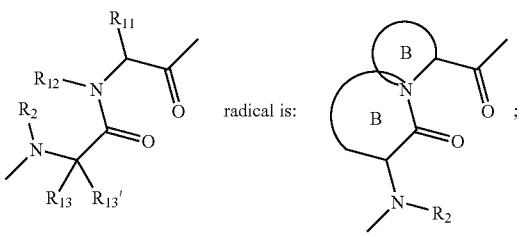 ;
wherein each B independently forms a 3- to a 20-membered carbocyclic or heterocyclic ring system;
wherein each ring B is either aromatic or nonaromatic;

wherein each heteroatom in the heterocyclic ring system is N, NH, O, S, SO, or SO$_2$;
wherein each ring is optionally fused to a (C6–C10)aryl, (C5–C10)heteroaryl, (C3–C10)cycloalkyl, or (C3–C10)heterocyclyl; and
wherein each ring has up to 3 substituents selected independently from J.
According to a preferred embodiment of formula (II), the radical is:
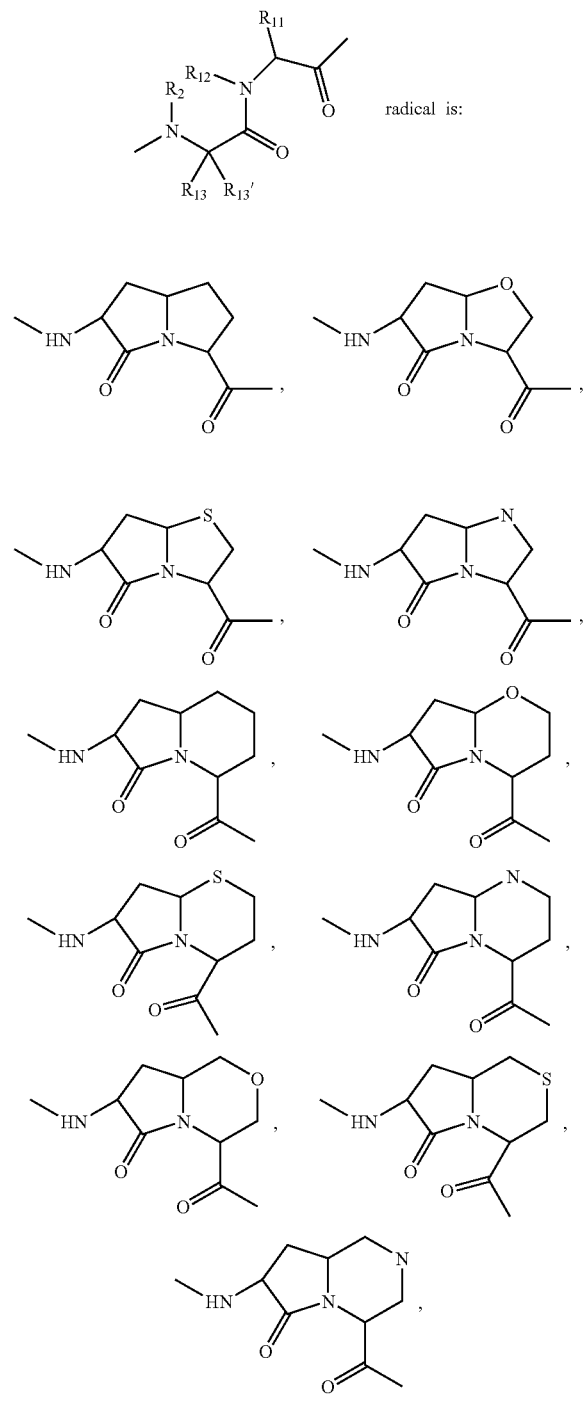
-continued
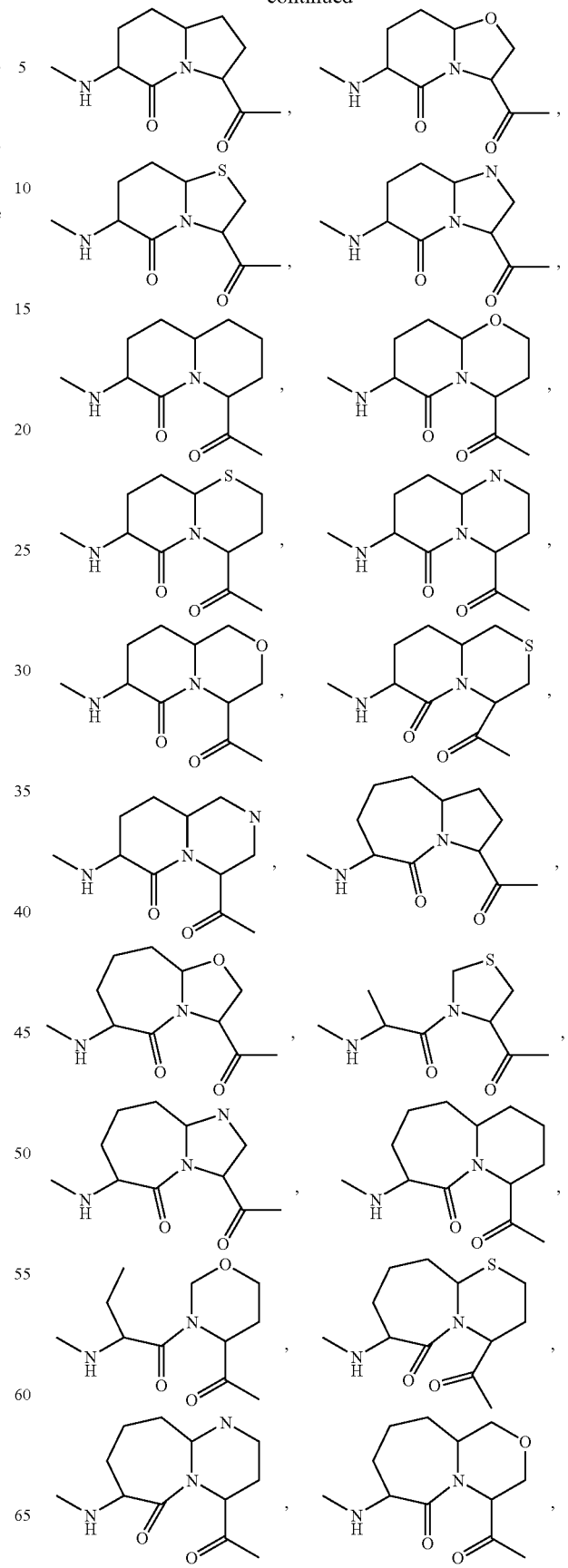

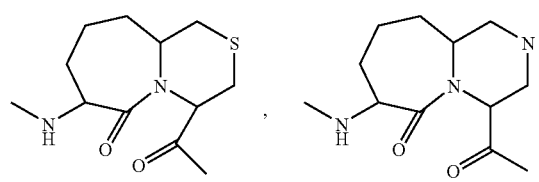
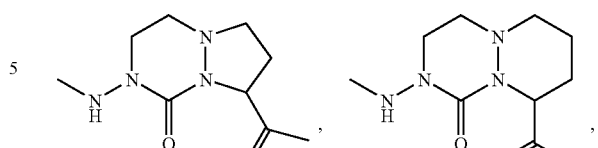
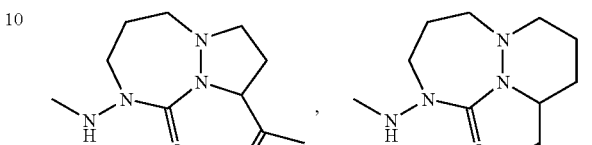
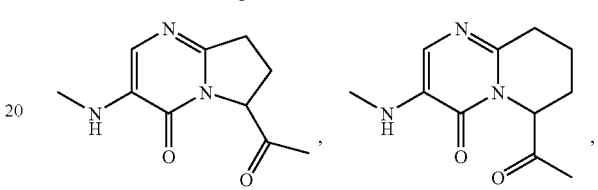
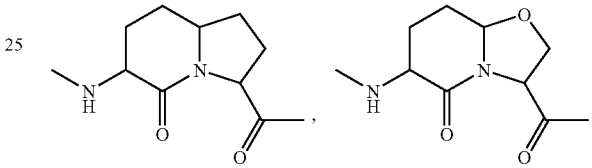
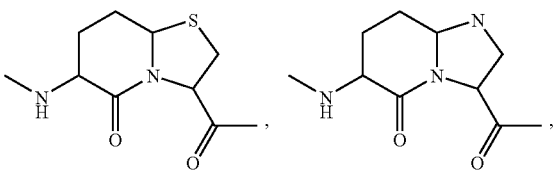
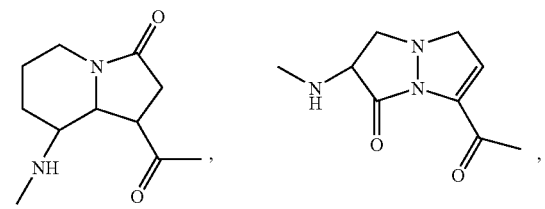
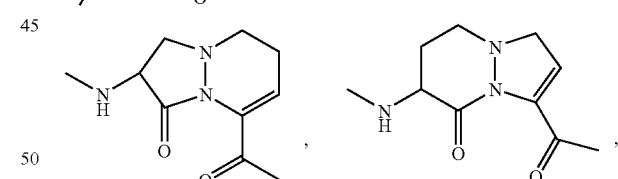
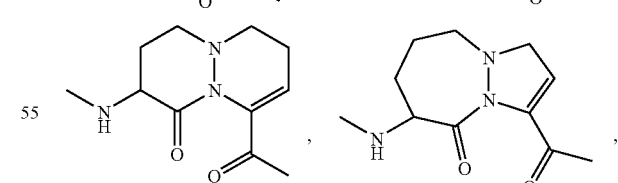
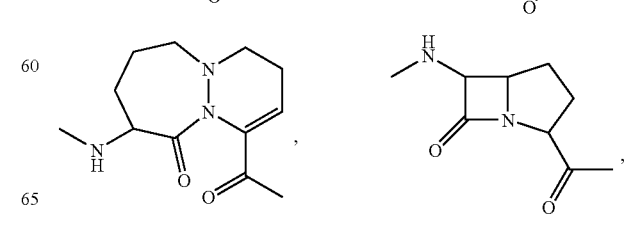
According to a preferred embodiment of formula (II), the
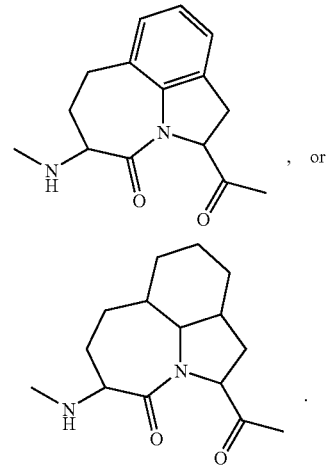 radical is:
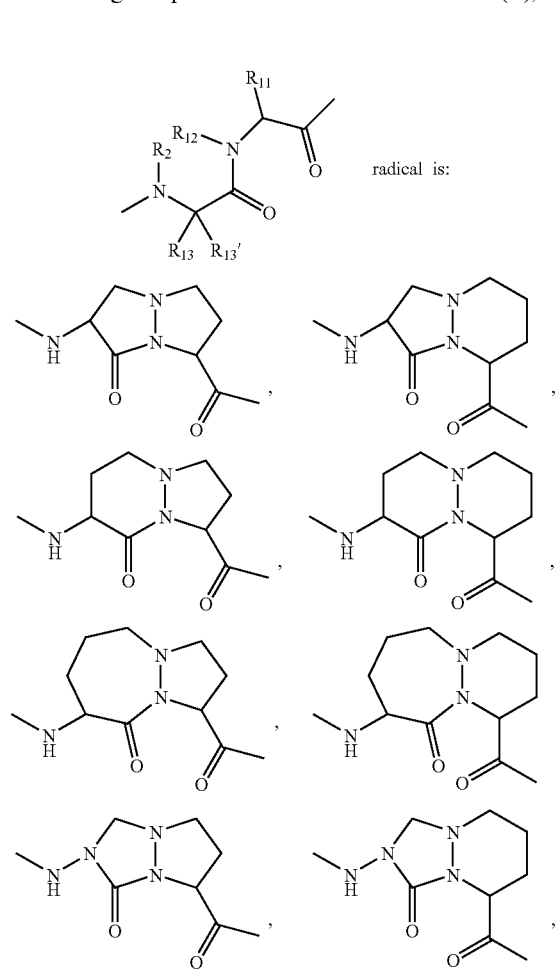

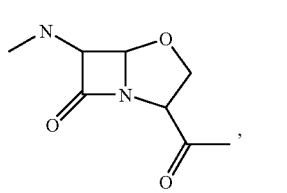
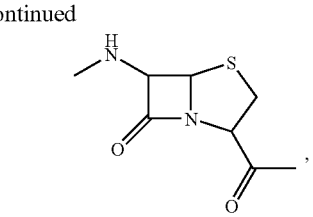
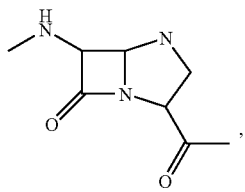
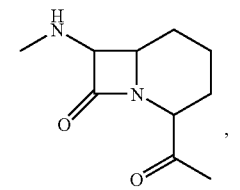
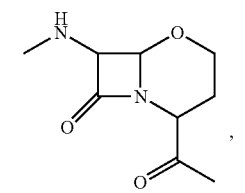
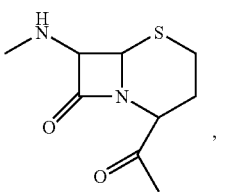
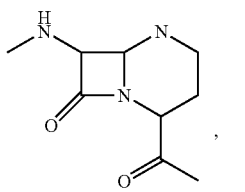
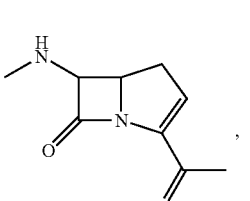
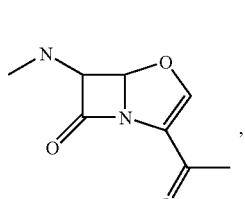
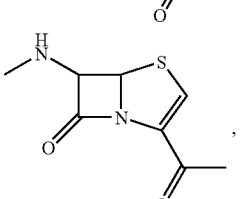
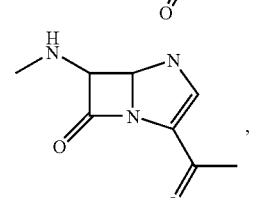
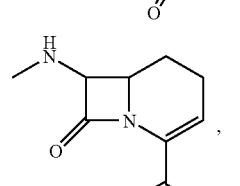
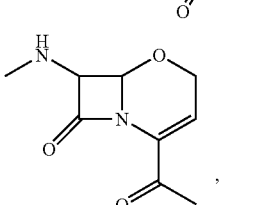, or 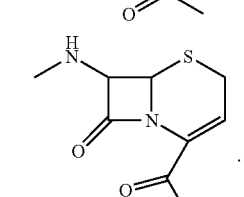.
In the embodiment immediately above, the ring is also selected from:
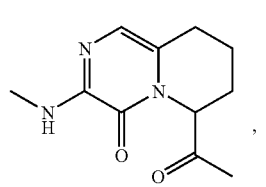
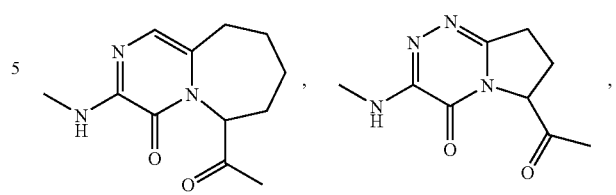
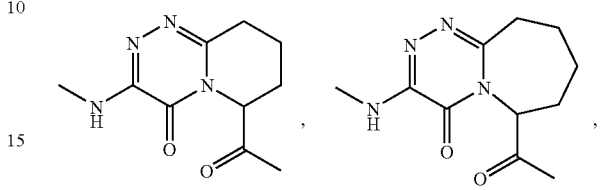
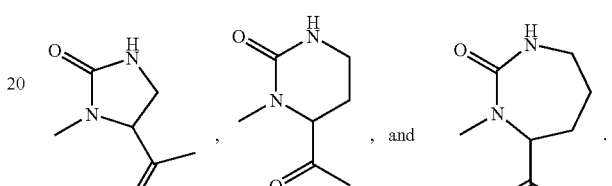
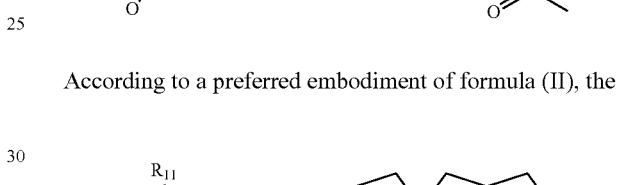
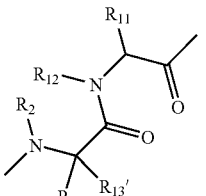
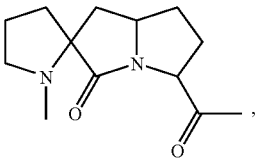, and 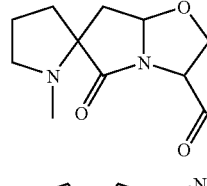.
According to a preferred embodiment of formula (II), the
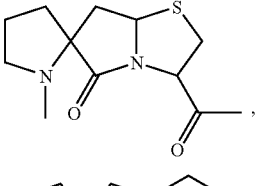 radical is: 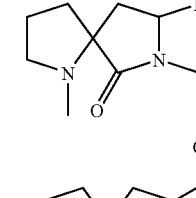
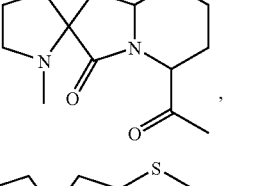
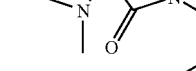
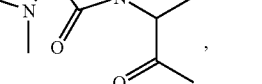
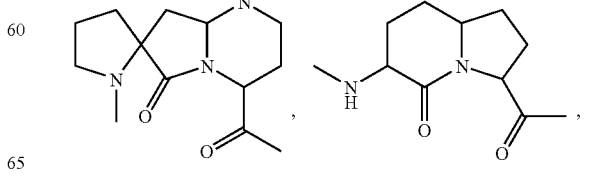

-continued

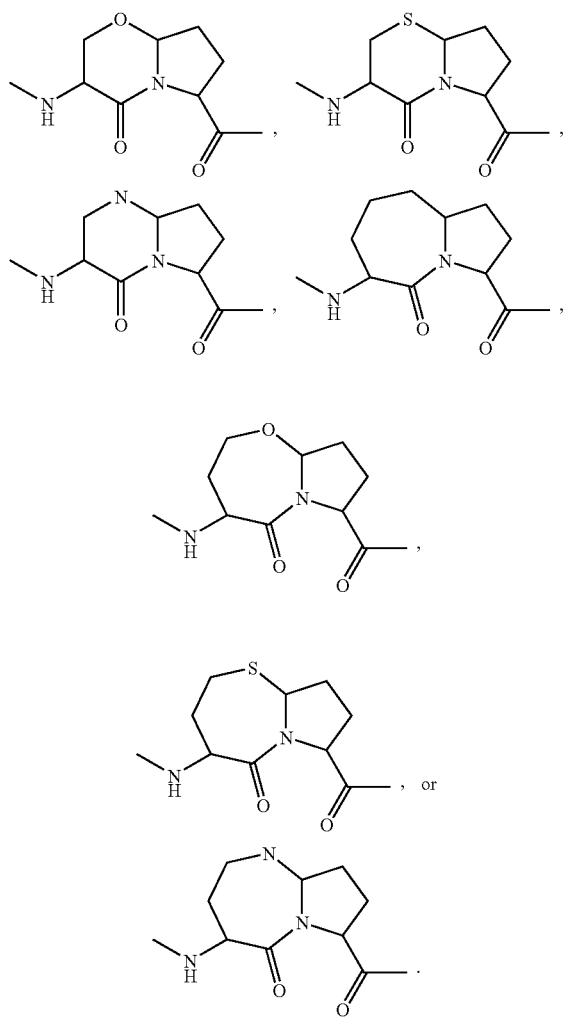

According to a preferred embodiment of formula (II), the

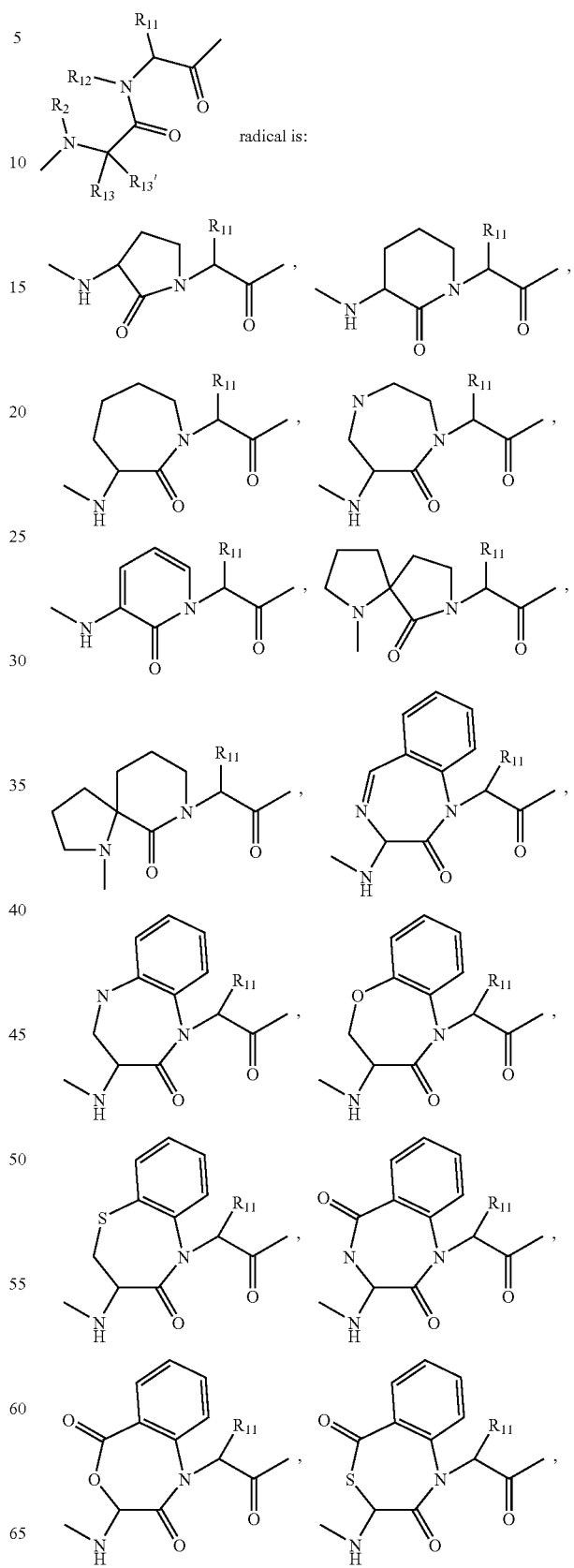

radical is:

wherein B forms a 3- to a 20-membered carbocyclic or heterocyclic ring system;

wherein each ring B is either aromatic or nonaromatic;

wherein each heteroatom in the heterocyclic ring system is N, NH, O, S, SO, or $SO_2$;

wherein each ring is optionally fused to a (C6–C10)aryl, (C5–C10)heteroaryl, (C3–C10)cycloalkyl, or (C3–C10)heterocyclyl; and wherein each ring has up to 3 substituents selected independently from J.

According to a preferred embodiment of formula (II), the

-continued

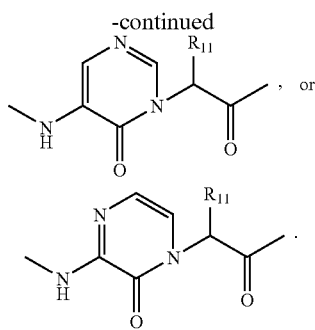

In the above radicals, it is understood that that $R_{11'}$ variable is hydrogen.

According to a preferred embodiment of formula (II), $R_{11}$ and $R_{12}$ together with the atoms to which they are bound form a 6- to 10-membered mono- or bicyclic carbocyclic or heterocyclic ring system; wherein each heteroatom in the heterocyclic ring system is selected from the group consisting of N, NH, O, S, SO, and $SO_2$; and wherein said ring has up to 3 substituents selected independently from J.

According to a preferred embodiment, the ring formed from $R_5$ and $R_{13}$, if present, is preferably an 18-membered ring.

According to a preferred embodiment, the ring formed from $R_1$ and $R_{12}$, if present, is preferably an 18-membered ring.

Any of the ring systems may be substituted as set forth herein. Preferably, the ring substituents are selected from oxo, fluoro, difluoro (particularly vicinal difluoro), and hydroxy. These substituents are the most preferred on the following ring systems:

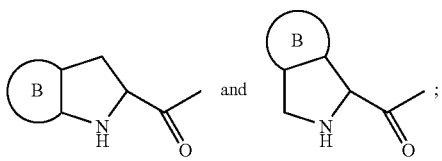

wherein B is a 5-membered carbocyclic ring, optionally having one unsaturated bond.

In preferred embodiments, heteroatoms are selected from the group consisting of N, NH, O, SO, and $SO_2$.

Preferred embodiments for any formula are also preferred embodiments for any other formula (I). For example, the preferred embodiments of $R_3$ in formula (I) are also the preferred embodiments of $R_{13}$ in formula (II); the preferred embodiments of $R_2$ in formula (I) are also the preferred embodiments of $R_{20}$ in formula (II); and the preferred embodiments of $R_6$ in formula (I) are also the preferred embodiments of $R_{17}$ in formula (II).

Any of the preferred embodiments recited above for T, V, $R_1$, $R_2$, $R_3$, A, X, Y, $R_4$, $R_5$ and W may be combined to produce a preferred embodiment of a compound of formula (IA).

Any of the preferred embodiments recited above for T, V, $R_1$, $R_2$, $R_3$, A, X, Y, $R_4$, $R_5$, and $R_{5'}$, and W may be combined to produce a preferred embodiment of a compound of formula (IB).

Any of the preferred embodiments recited above for $R_1$, $R_2$, $R_4$, $R_5$, and $R_{5'}$, $R_{11}$, $R_{12}$, $R_{13}$, $R_{13'}$, $R_{14}$, $R_{15}$, $R_{16}$, $R_9$, $R_{20}$, $Z_2$, W may be combined to produce a preferred embodiment of a compound of formula (II).

According to another embodiment, the present invention provides compounds of formula (I'):

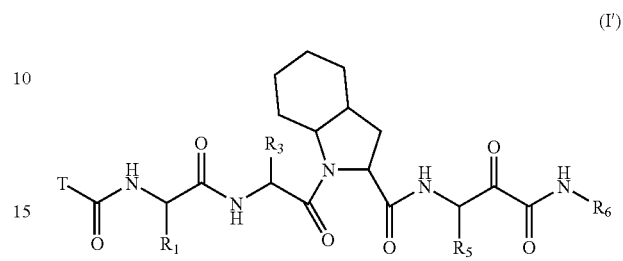

wherein:

$R_1$ and $R_3$ each is independently (C1–C6)aliphatic, cyclopentyl or cyclohexyl;

$R_5$ is ethyl, propyl or allyl;

$R_6$ is cyclopropyl, cyclobutyl, cyclopentyl, cyclohexyl, benzyl, (S)-methylbenzyl; and T is (C3–C10)heterocyclyl or (C5–C10)heteroaryl ring wherein said ring contains at least one hydrogen donor moiety selected from —$NH_2$, —NH—, —OH or —SH; or T is selected from:

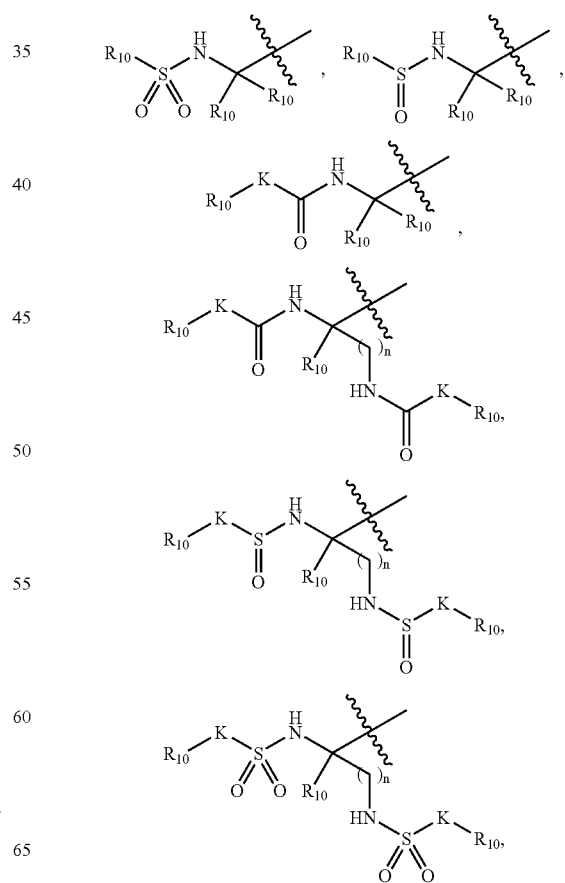

-continued

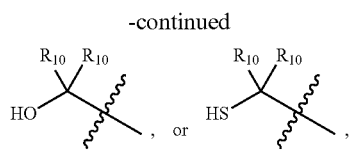

wherein R$_{10}$ and K are as defined above.

According to another embodiment, the present invention provides compounds of formulae (II' and II"):

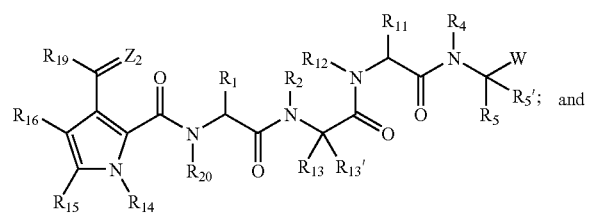
(II')

(II")

wherein thew variables are as defined herein.

According to a preferred embodiment, the stereochemistry of a compound of this invention corresponds to that depicted in compounds 1–62a and 63–68.

Another embodiment of this invention provides a process for preparing a compound of this invention. These process are described in the schemes and examples.

Examples of specific compounds of formula (I) are set forth below in Table 2.

TABLE 2

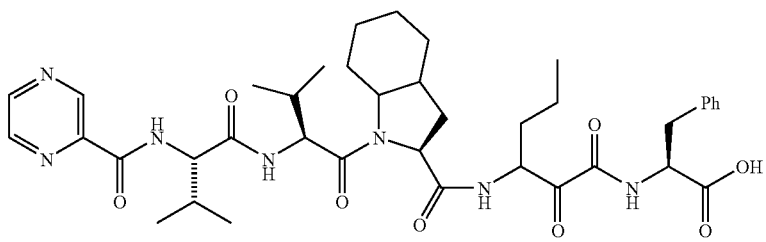

1

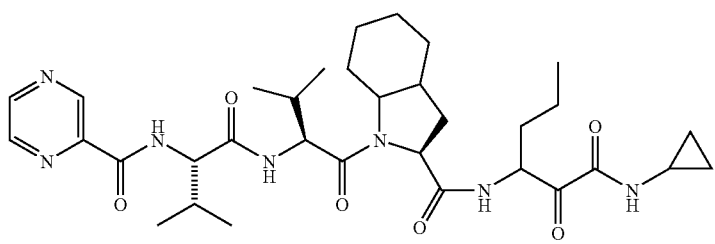

2

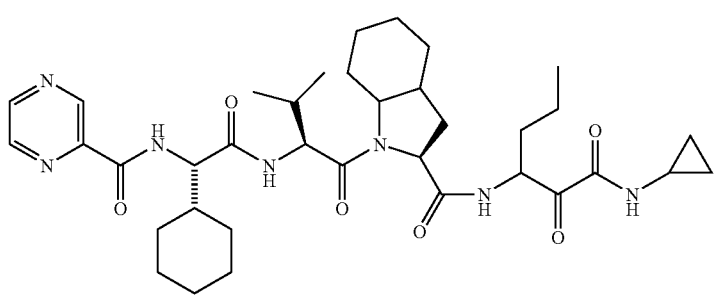

3

TABLE 2-continued
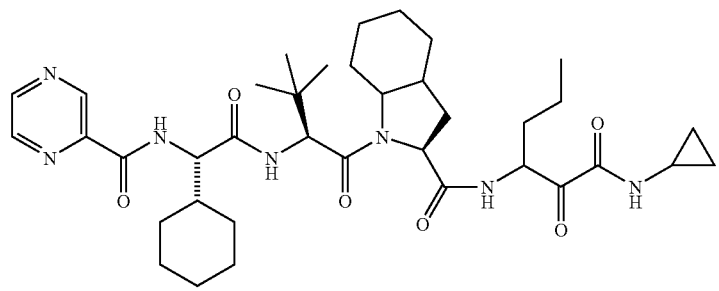
4
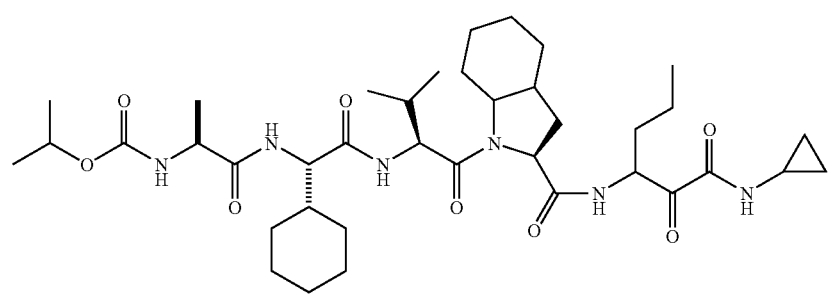
5
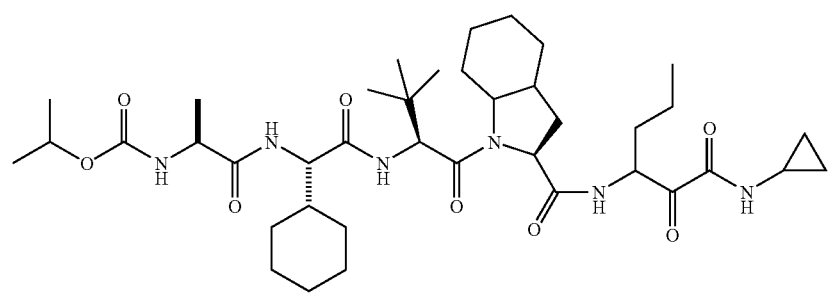
6
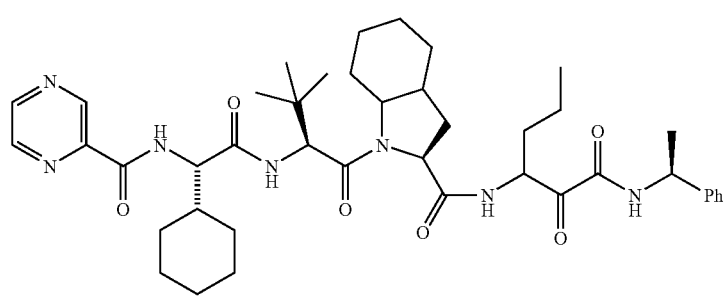
7

TABLE 2-continued
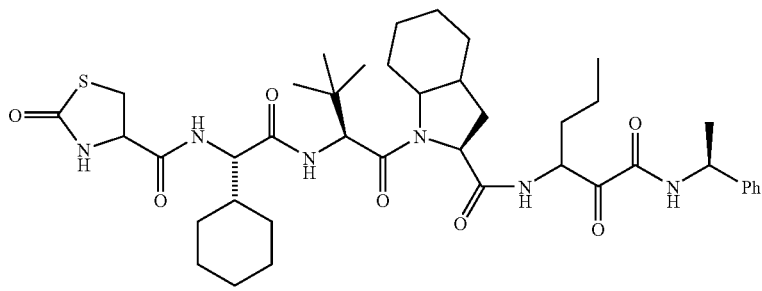
8
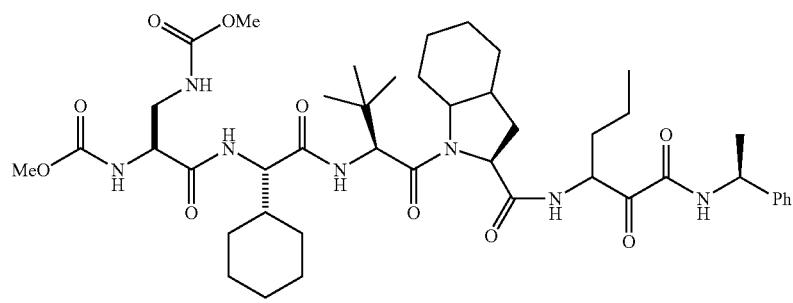
9
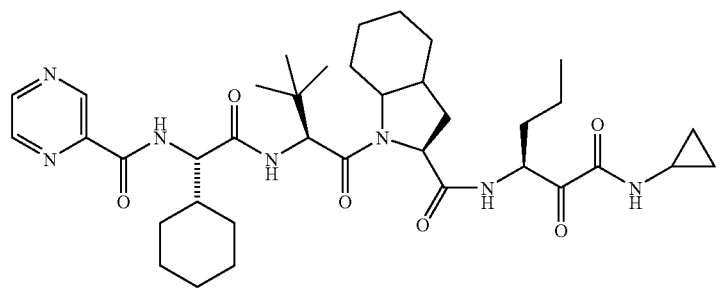
10
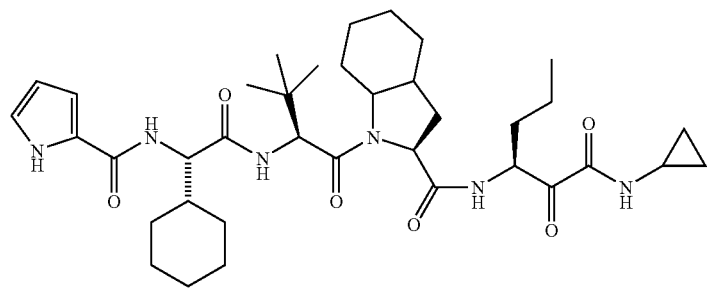
11

TABLE 2-continued
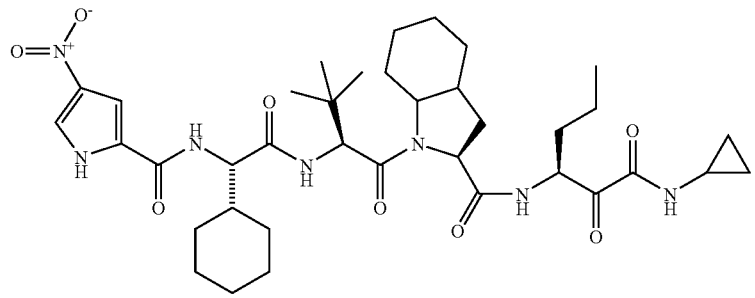
12
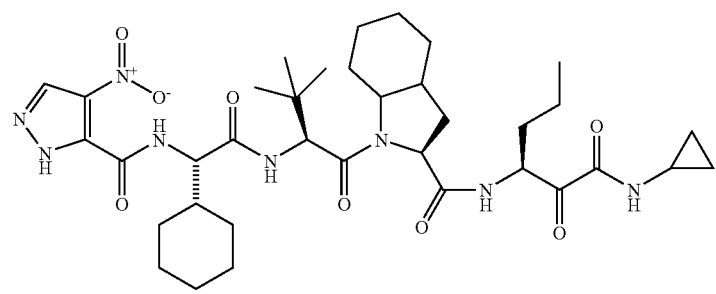
13
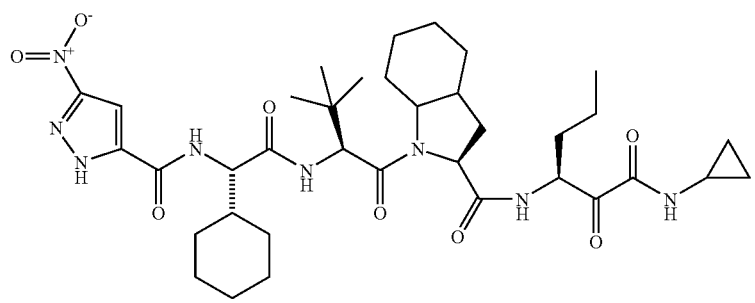
14
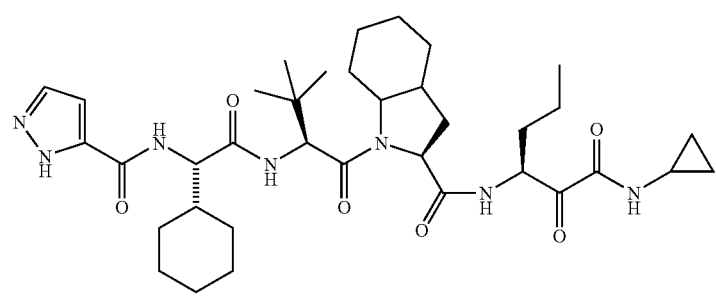
15

TABLE 2-continued
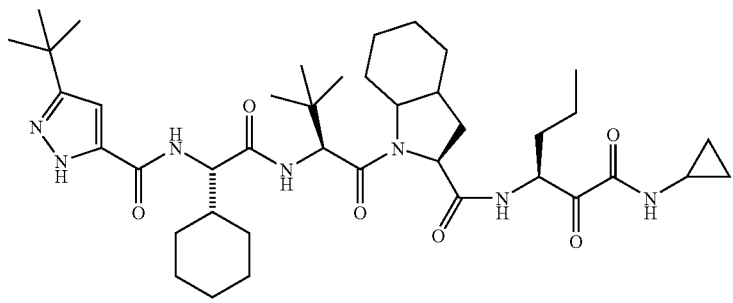
16
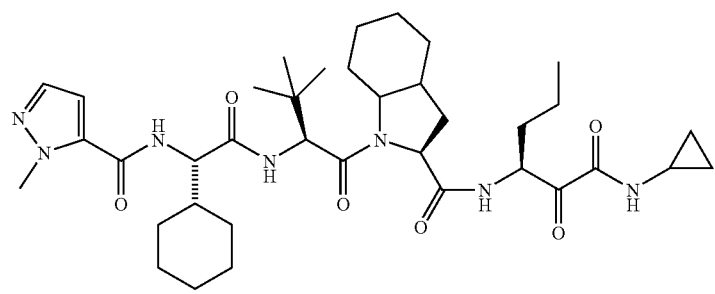
17
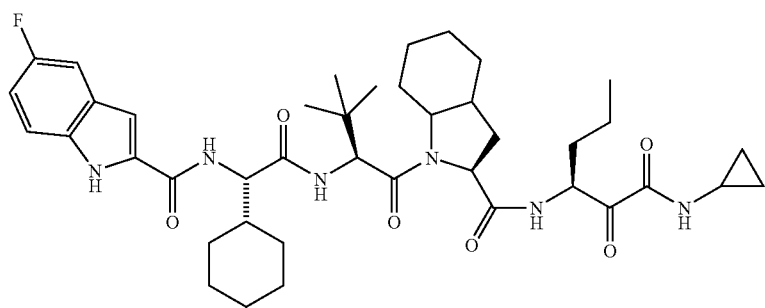
18
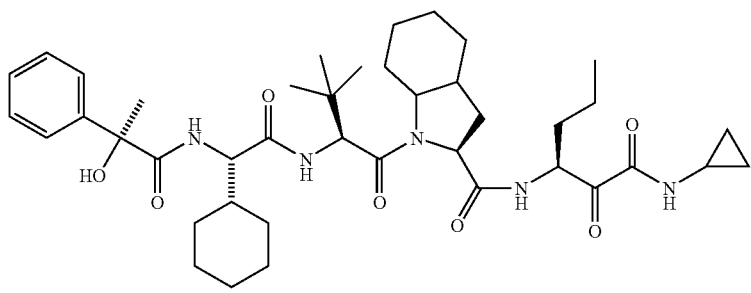
19

TABLE 2-continued
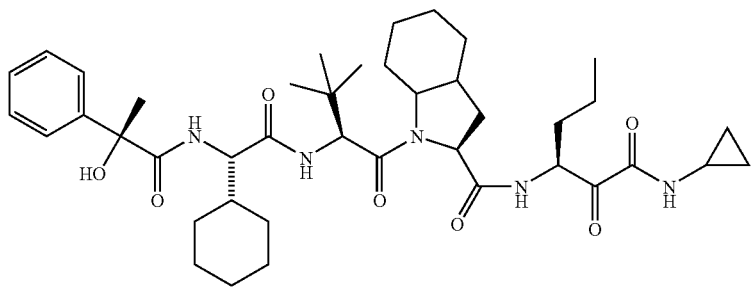
20
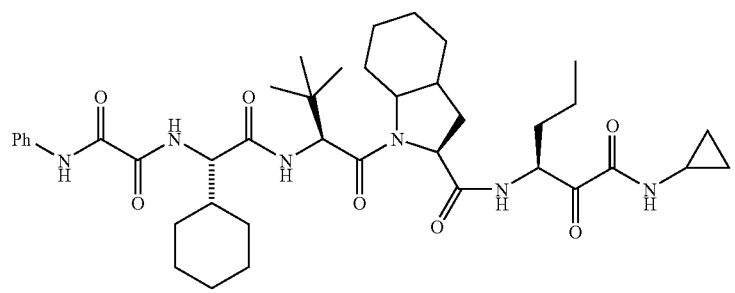
21
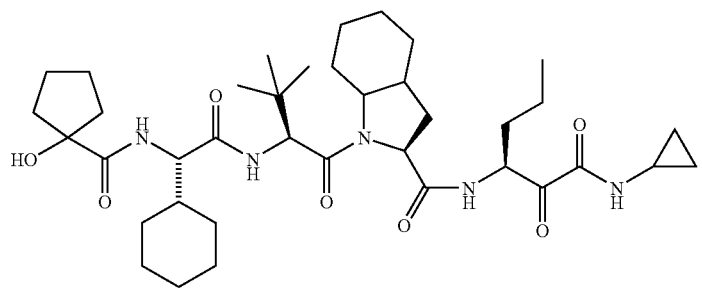
22
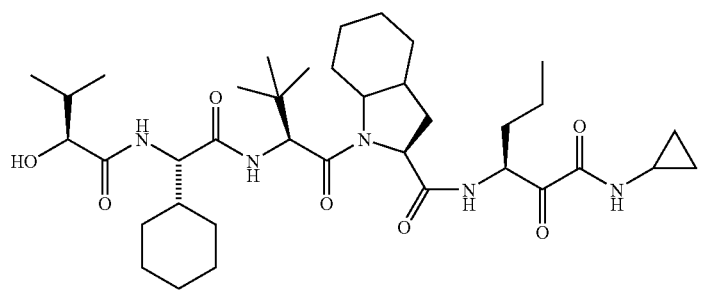
23

TABLE 2-continued
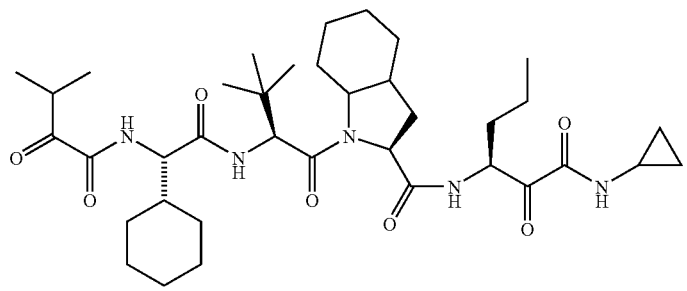
24
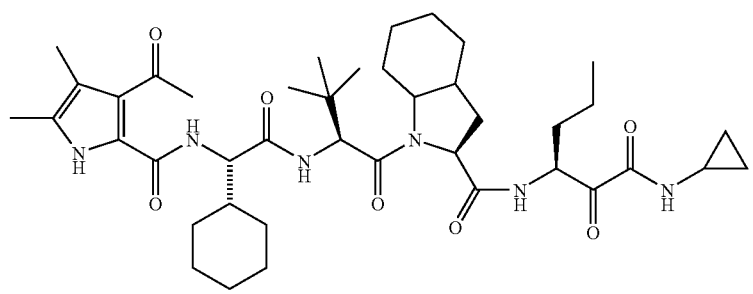
25
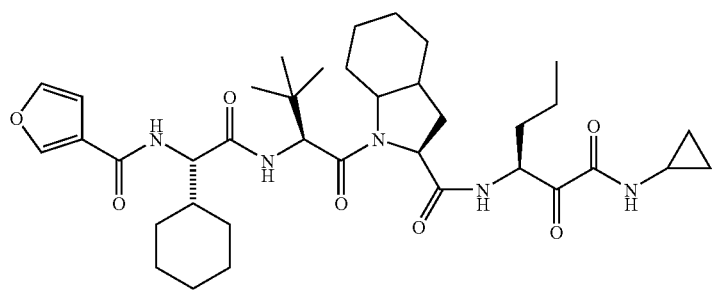
26
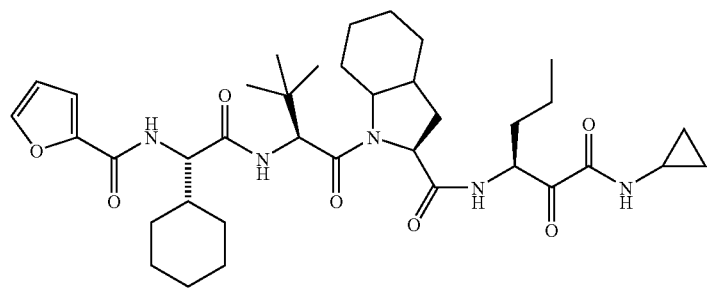
27

TABLE 2-continued
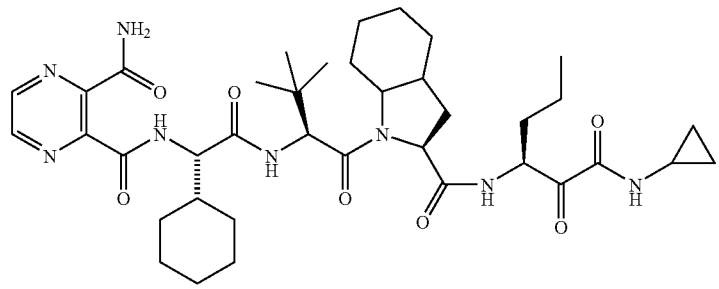
28
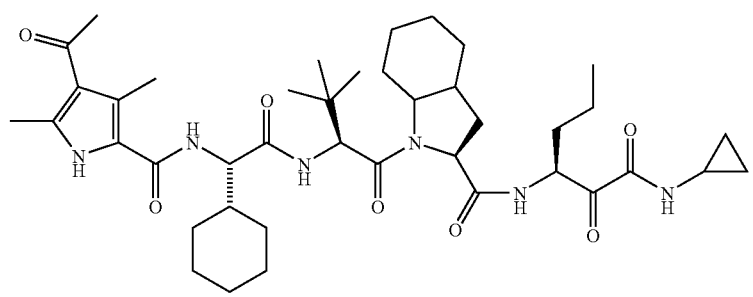
29
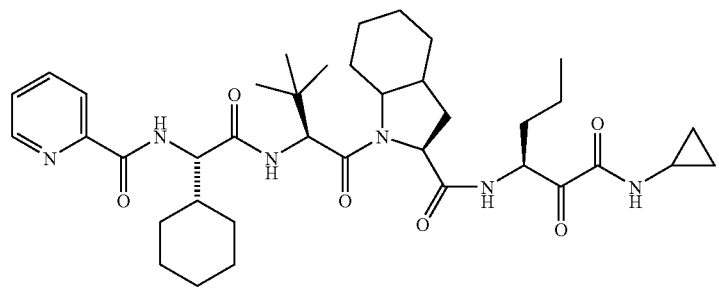
30
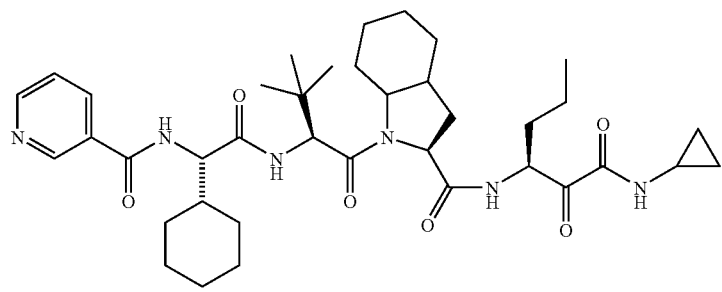
31

TABLE 2-continued
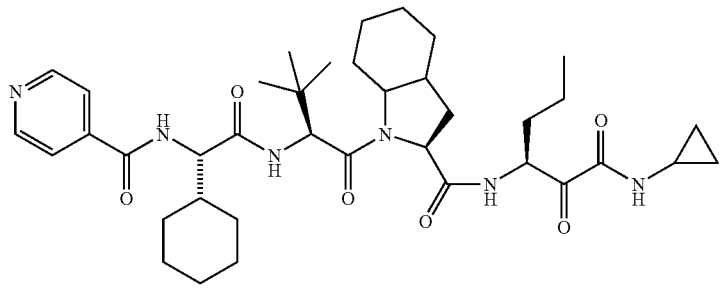
32
Examples of specific compounds of formula (I) are set forth below in Table 3.
TABLE 3
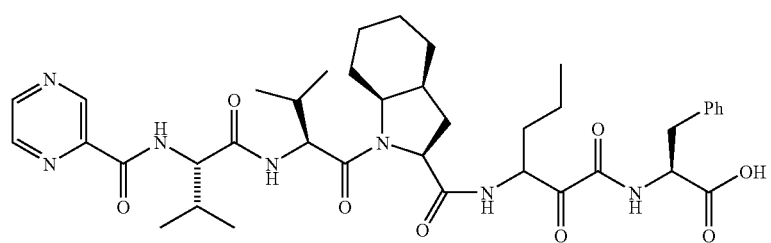
1a
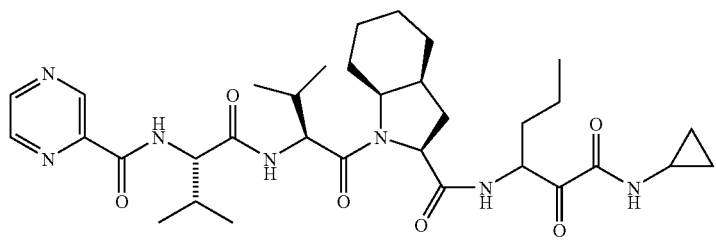
2a
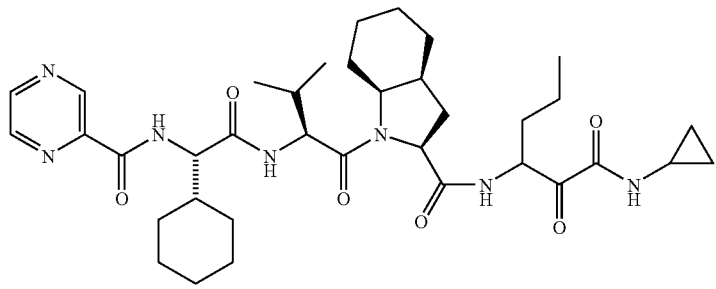
3a TABLE 3-continued
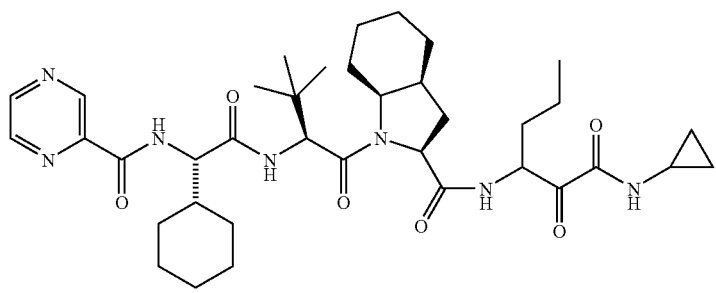
4a
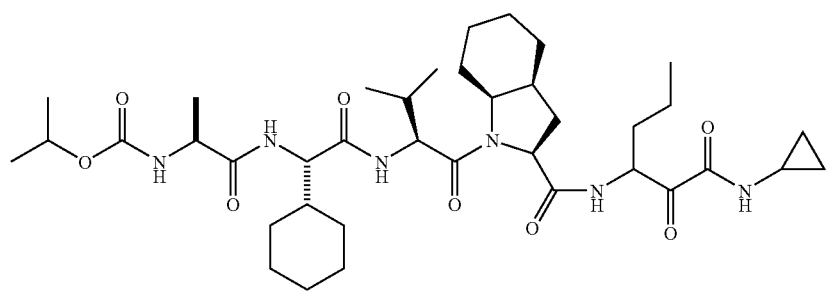
5a
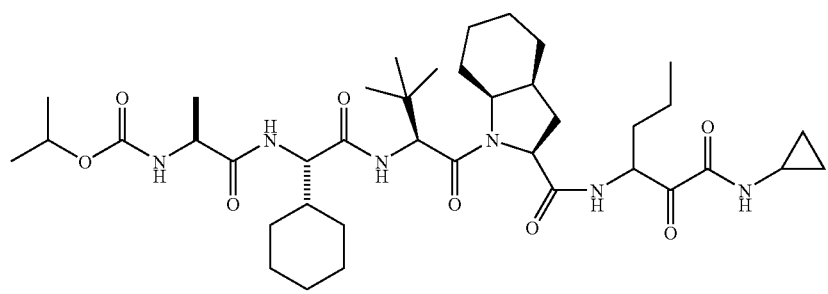
6a
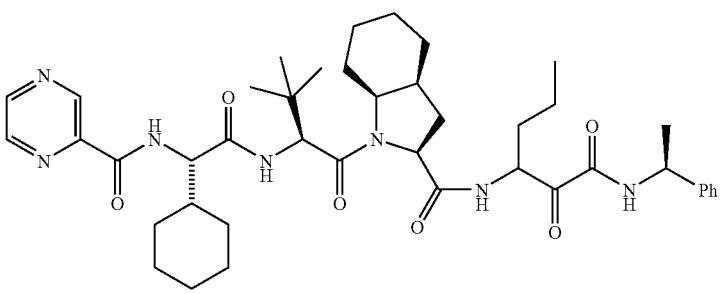
7a TABLE 3-continued
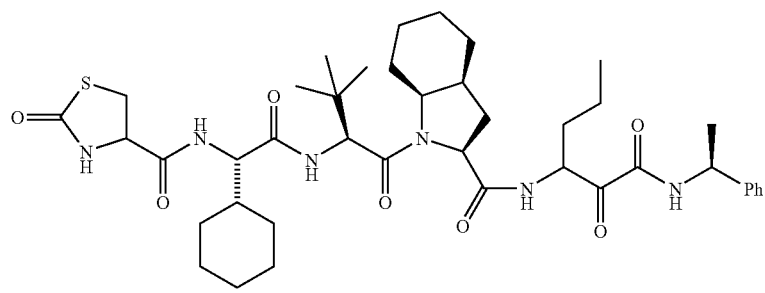
8a
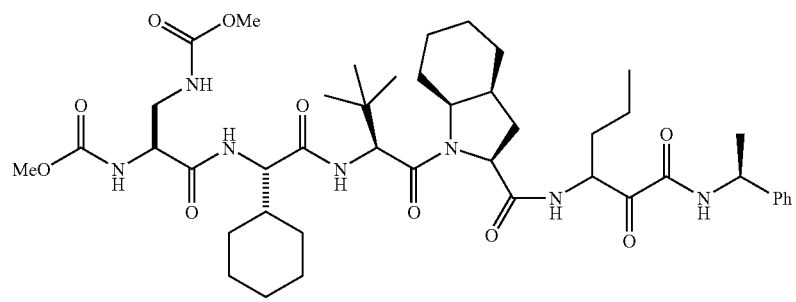
9a
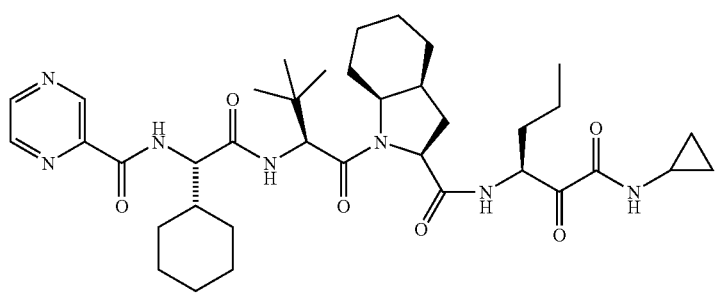
10a
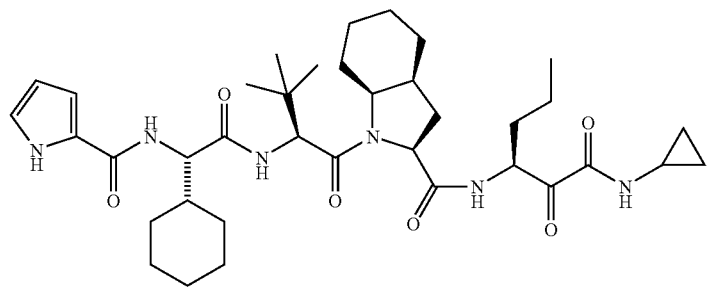
11a TABLE 3-continued
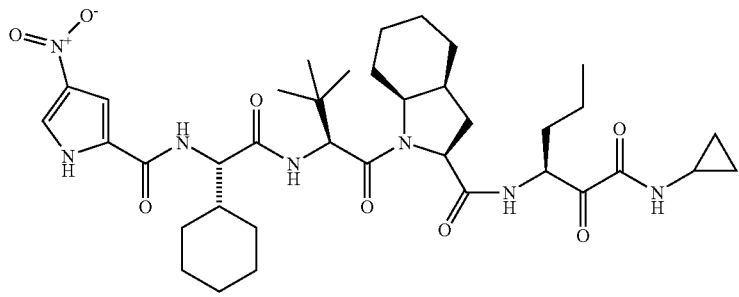
12a
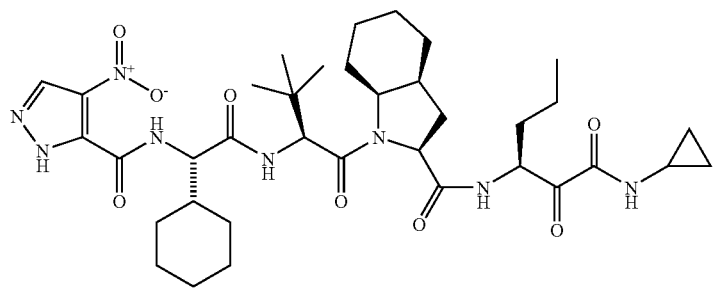
13a
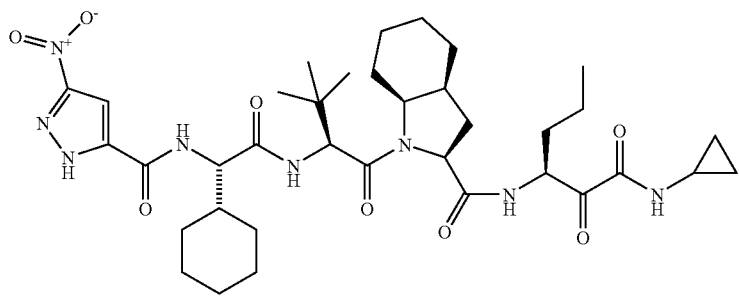
14a
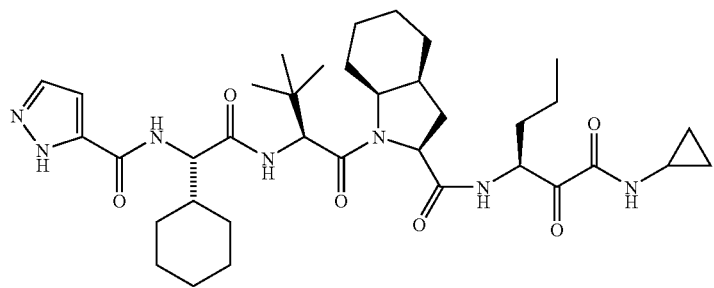
15a TABLE 3-continued
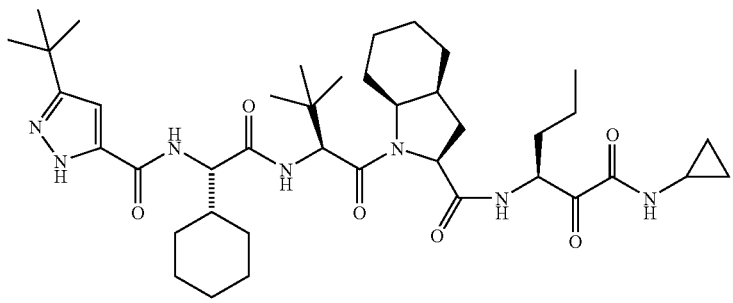
16a
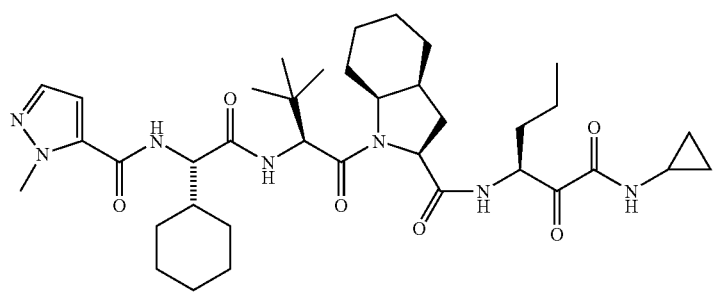
17a
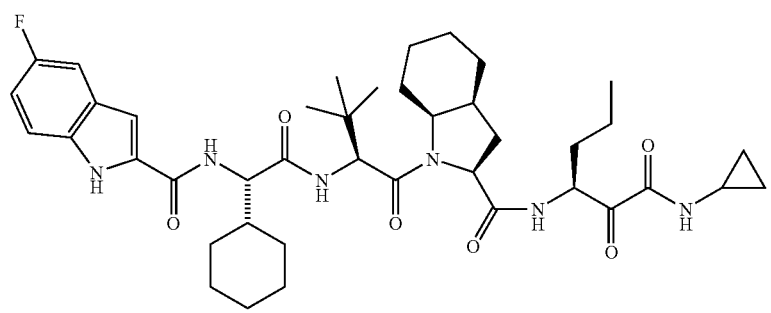
18a
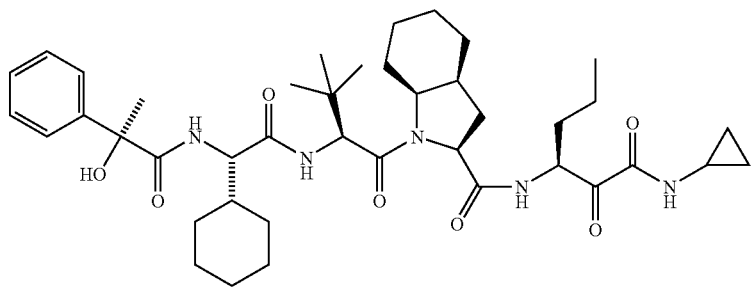
19a TABLE 3-continued
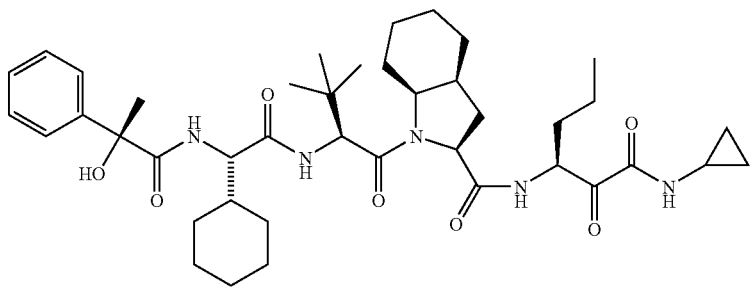
20a
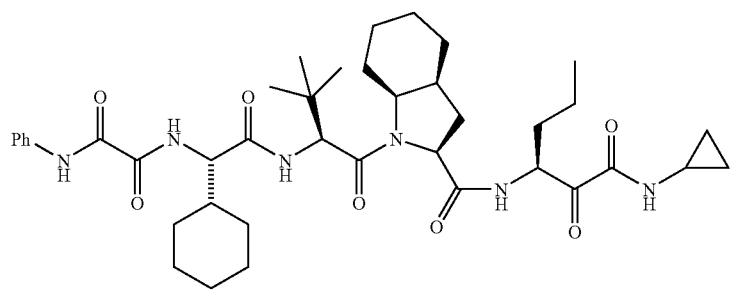
21a
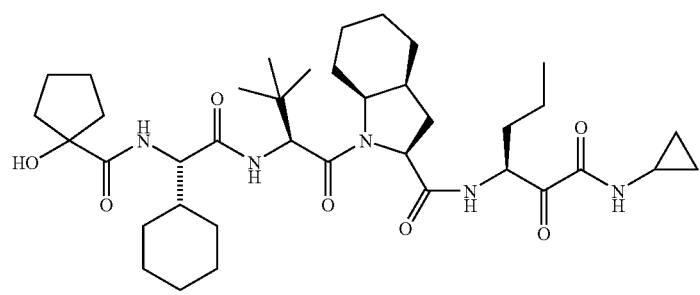
22a
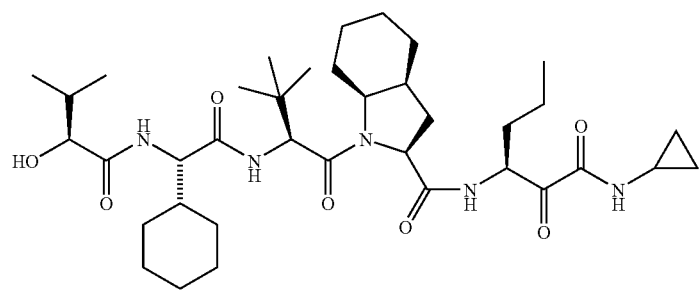
23a TABLE 3-continued
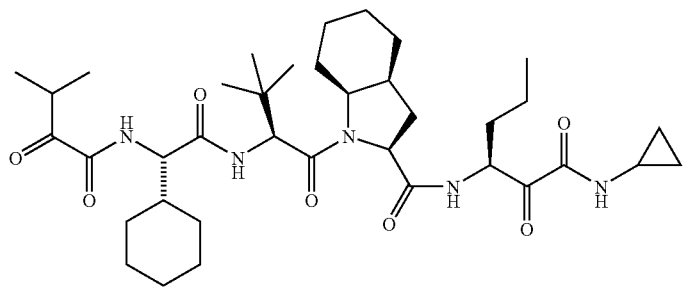
24a
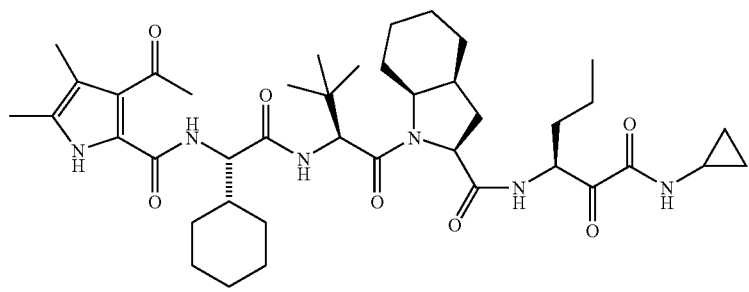
25a
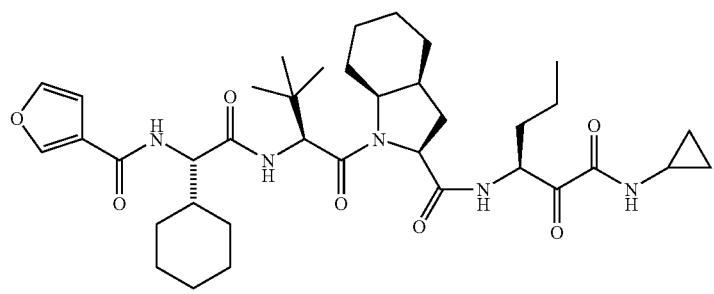
26a
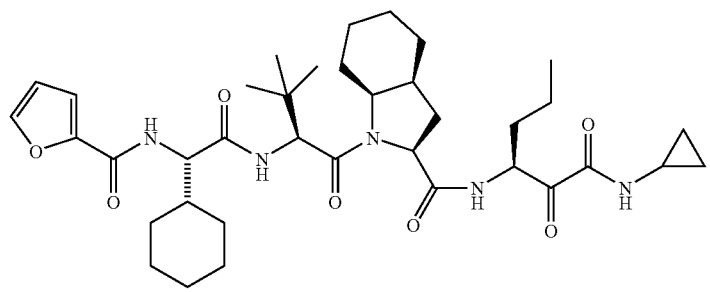
27a TABLE 3-continued
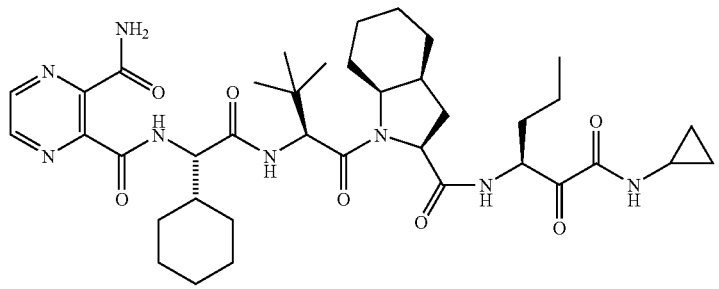
28a
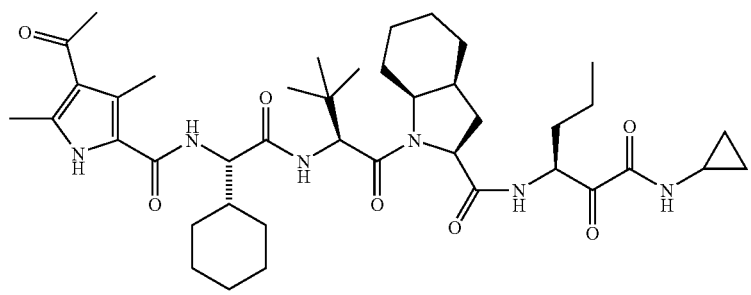
29a
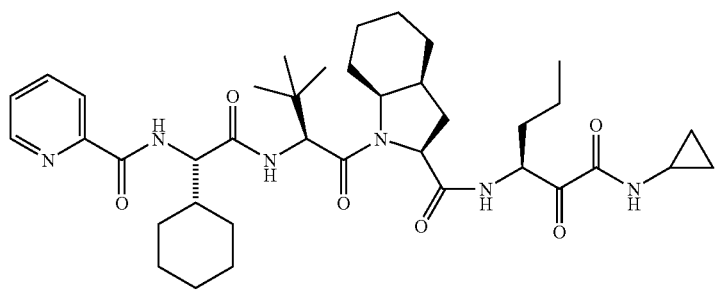
30a
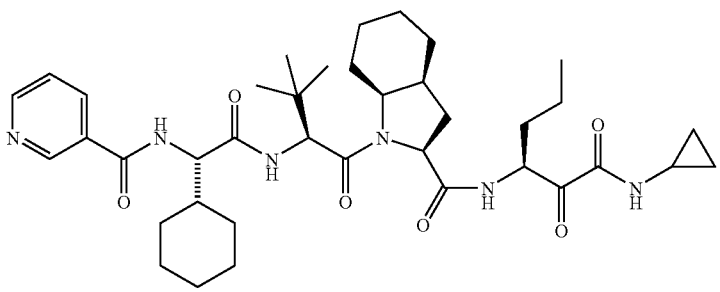
31a TABLE 3-continued
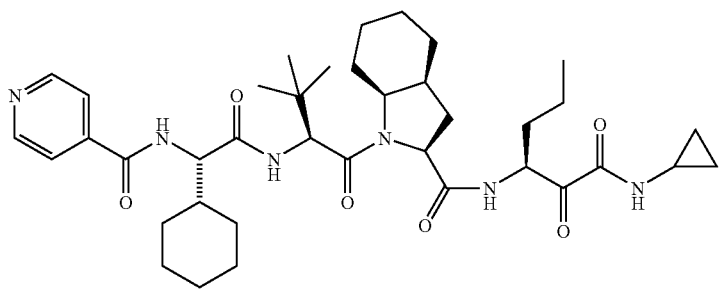
32a
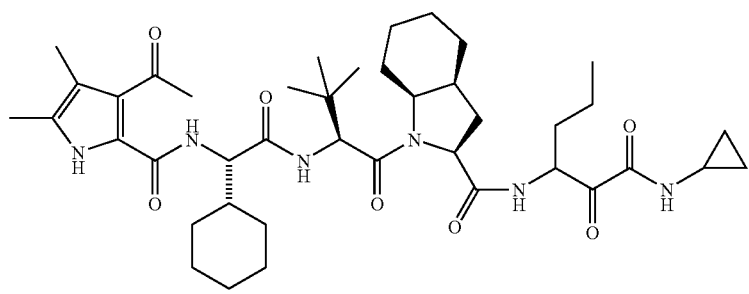
33a
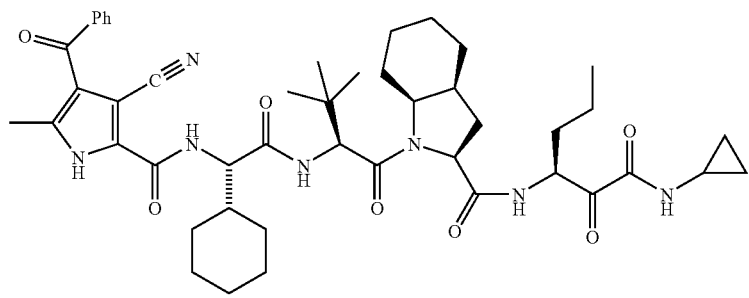
34a
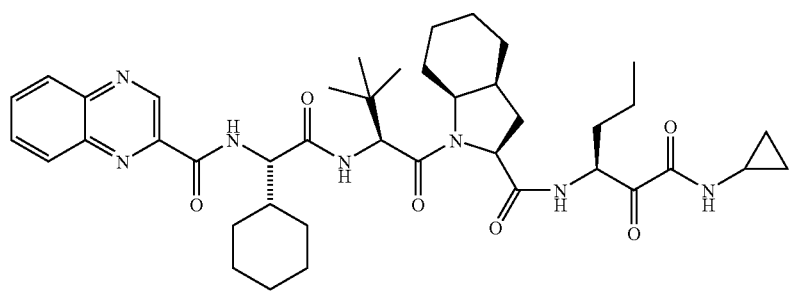
35a TABLE 3-continued
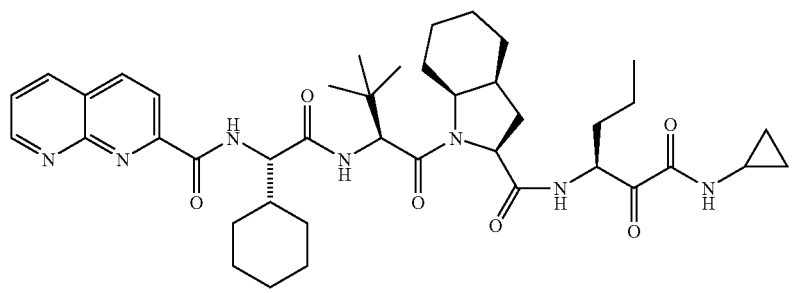
36a
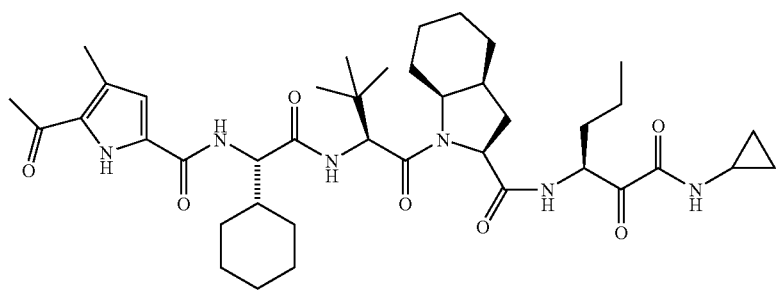
37a
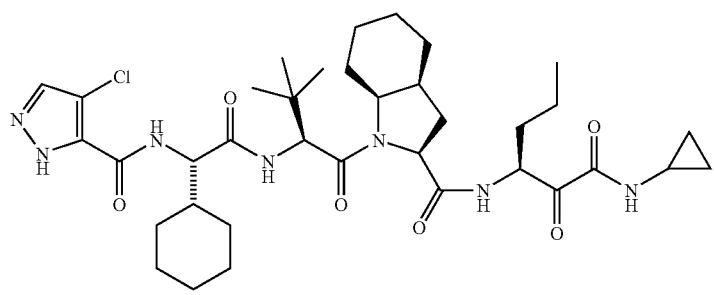
38a
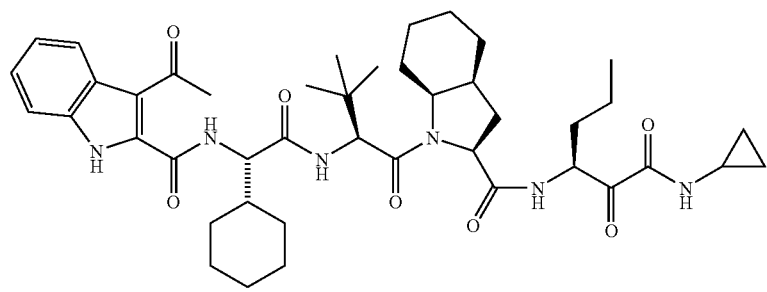
39a TABLE 3-continued
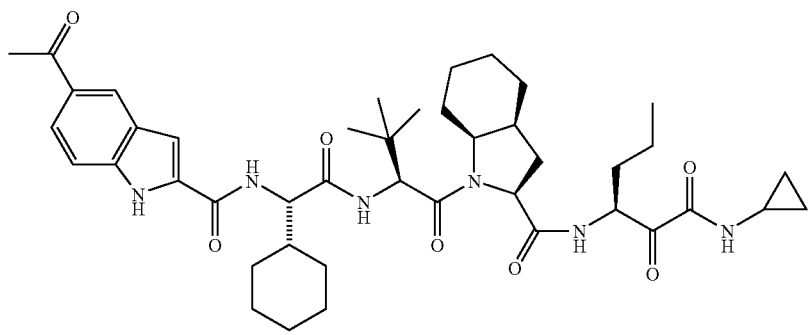
40a
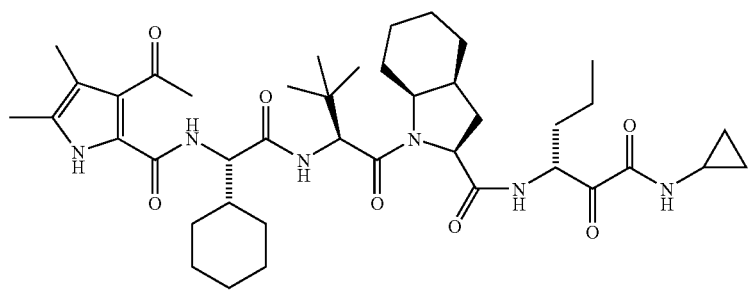
41a
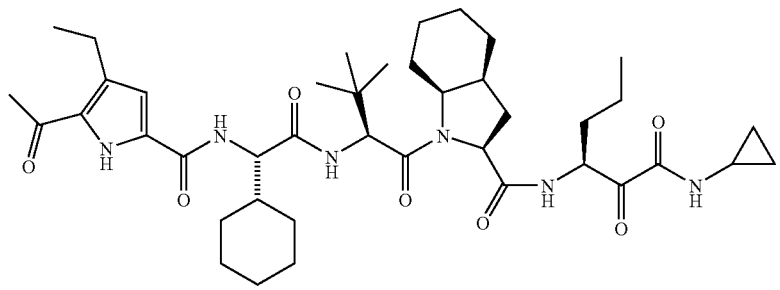
42a
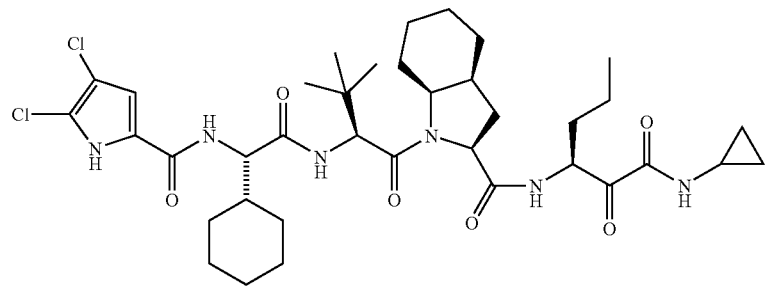
43a TABLE 3-continued
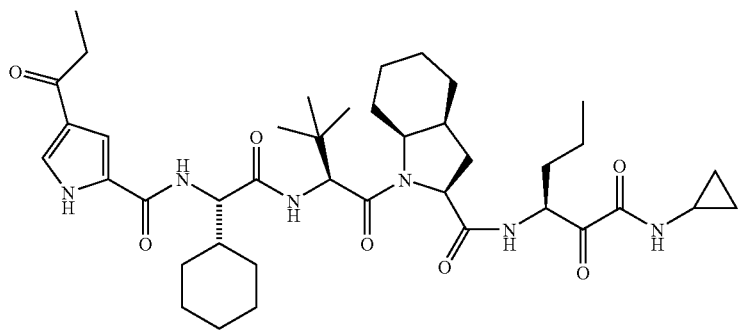
44a
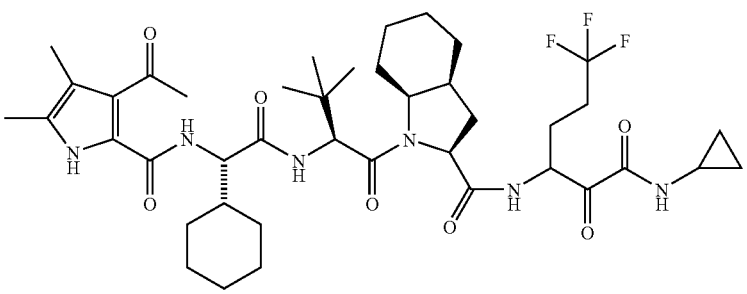
45a
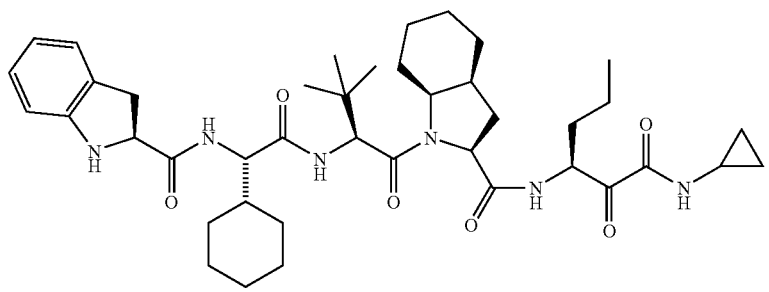
46a
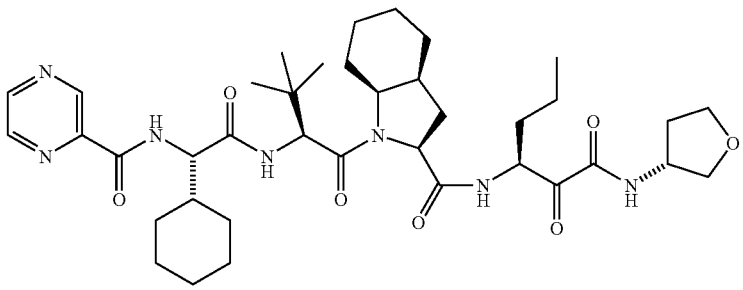
47a TABLE 3-continued
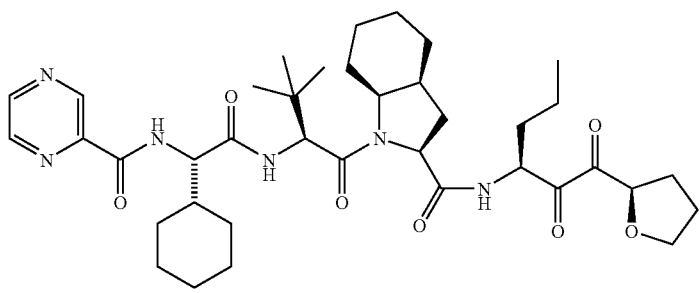
48a
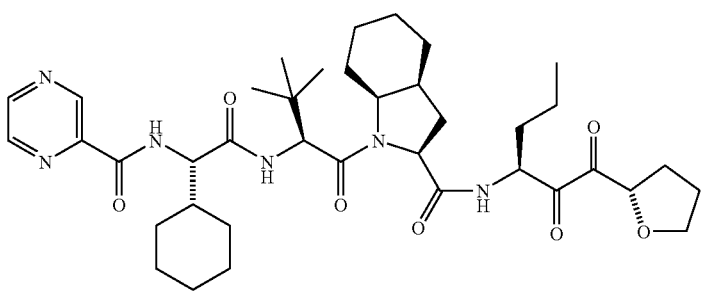
49a
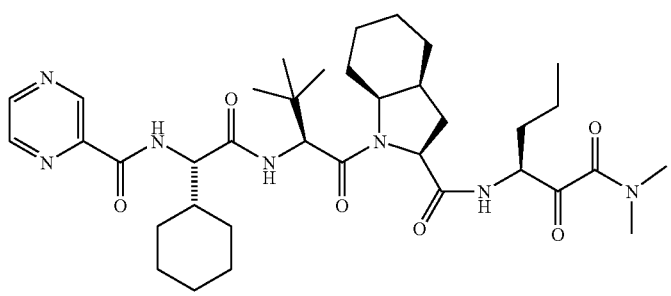
50a
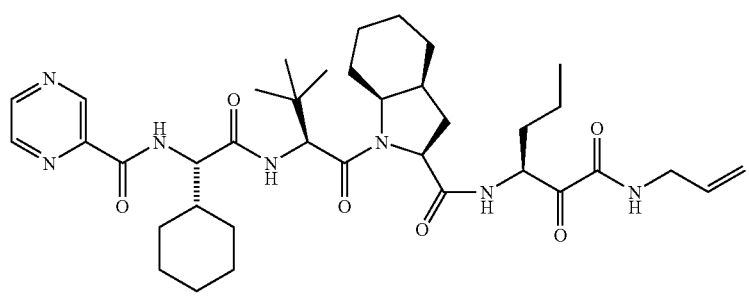
51a TABLE 3-continued
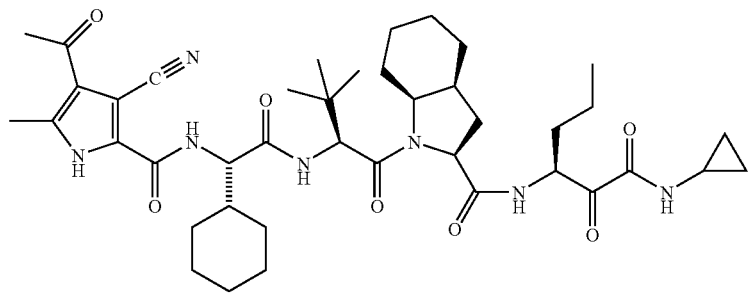
52a
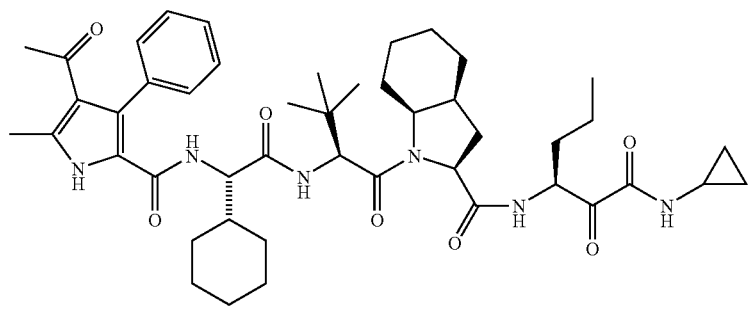
53a
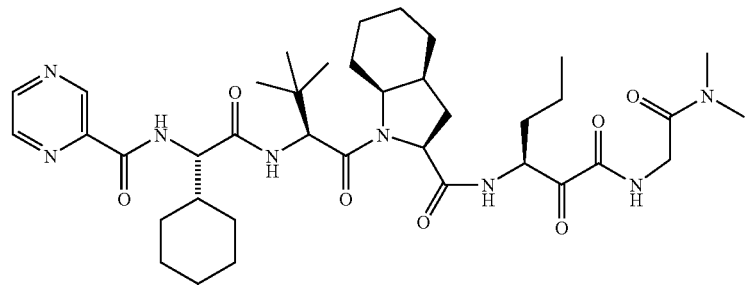
54a
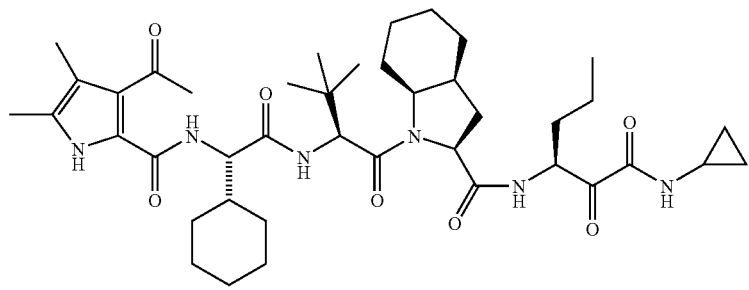
55a TABLE 3-continued
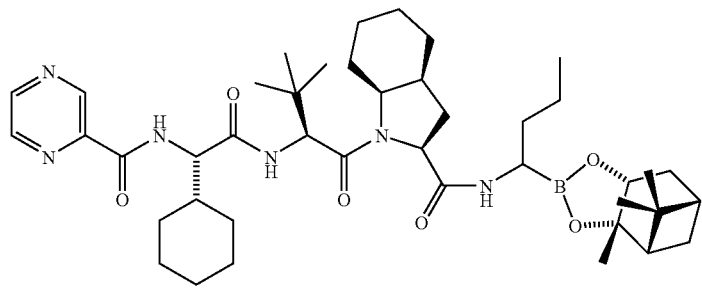
56a
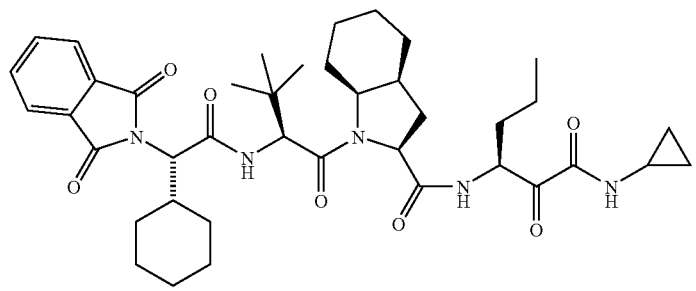
57a
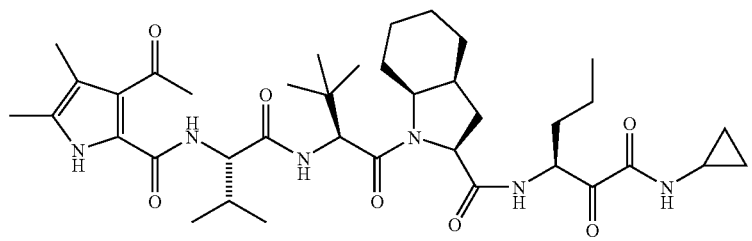
58a
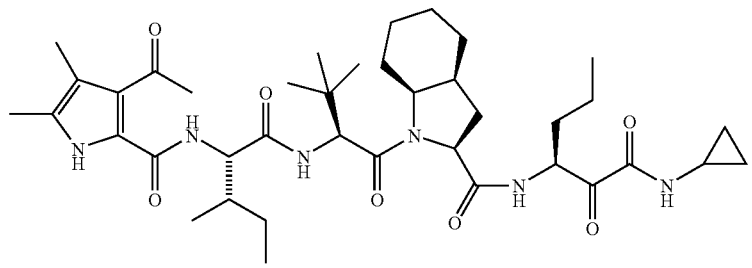
59a
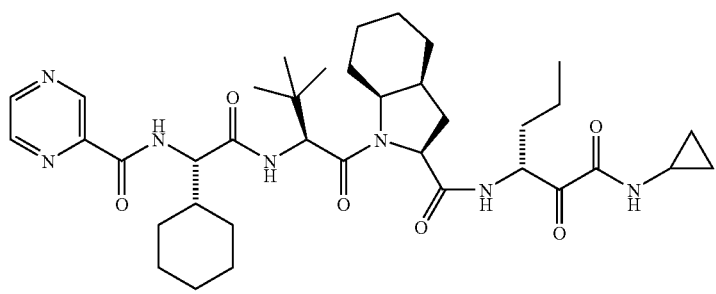
60a TABLE 3-continued
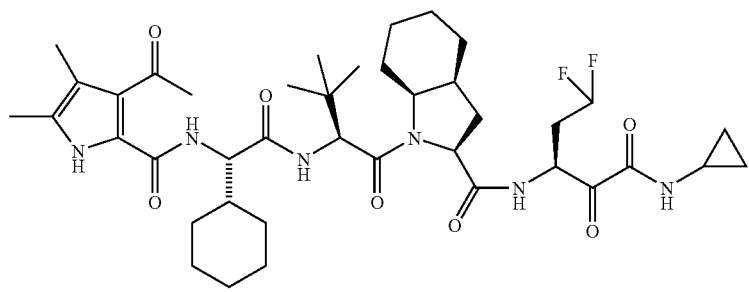
61a
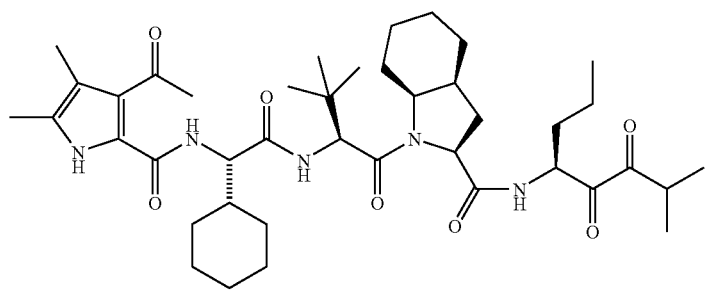
62a
Examples of other specific compounds of formula (II) of the present invention are set forth below in Table 4.
TABLE 4
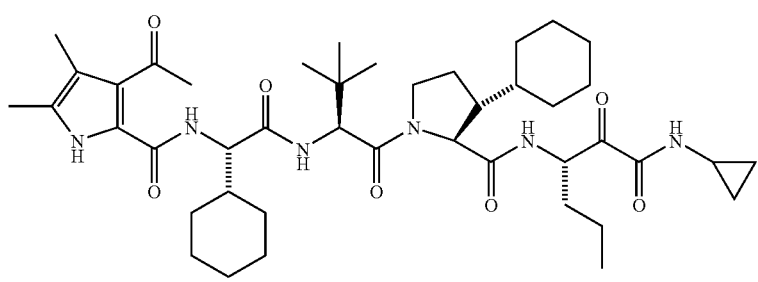
63
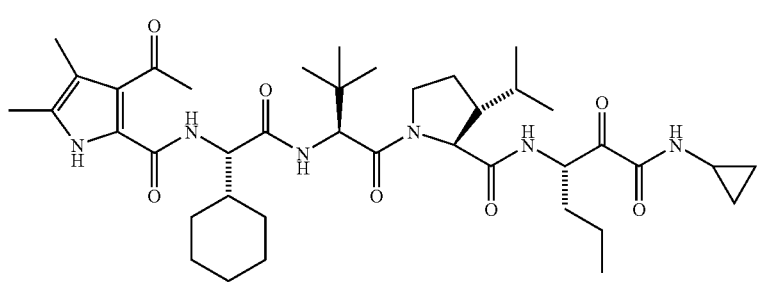
64

TABLE 4-continued

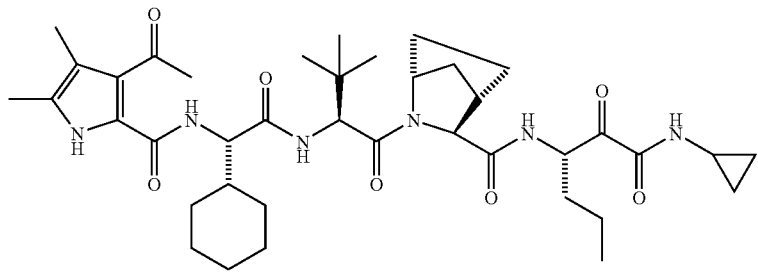

65

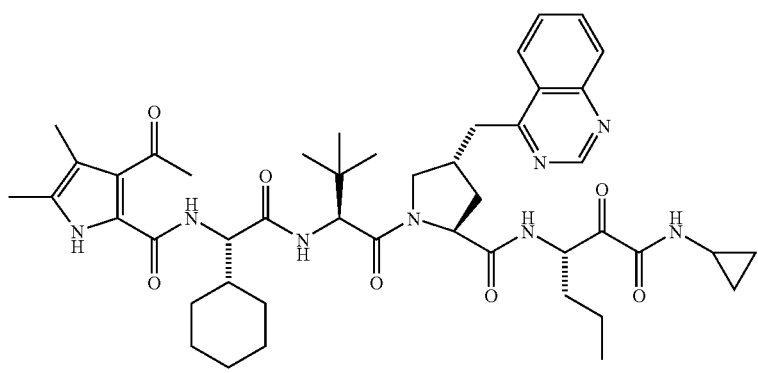

66

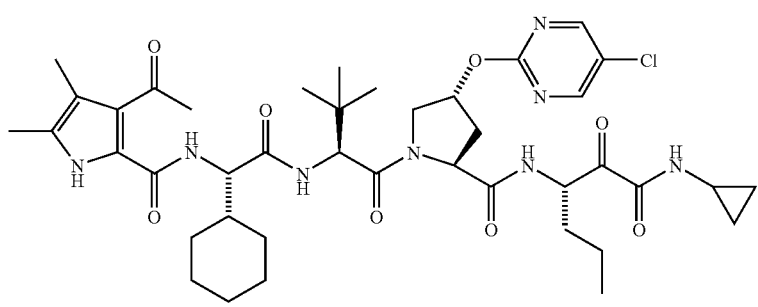

67

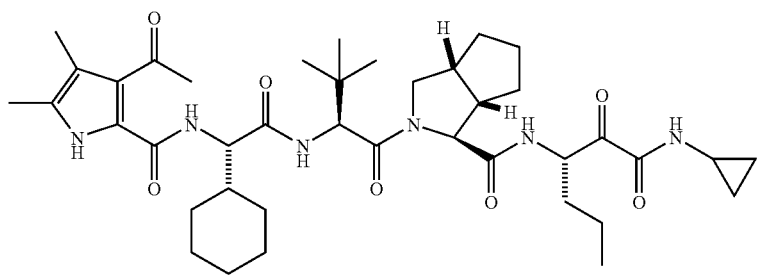

68

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

Preferably, the compounds of this invention have the structure and stereochemistry depicted in compounds 1a–62a and 63–68.

Any of the preferred embodiments recited above, including those embodiments in the above species, may be combined to produce a preferred embodiment of this invention.

Abbreviations which are used in the schemes, preparations and the examples that follow are:
THF: tetrahydrofuran
DMF: N,N,-dimethylformamide
EtOAc: ethyl acetate
ACOH: acetic acid
HOBt: 1-hydroxybenzotriazole hydrate
EDC: 1-(3-dimethylaminopropyl)-3-ethylcarbodiimide hydrochloride
NMM: N-methylmorpholine
NMP: N-methylpyyrolidinone
EtOH: ethanol
t-BuOH: tert-butanol
$Et_2O$: diethyl ether
BOC: tert-butyloxycarbonyl
$BOC_2O$: di-tert-butyldicarbonate
Cbz: benzyloxycarbonyl
Chg: cyclohexylglycine
tBG: tert-butylglycine
Fmoc: 9-fluorenyl methyloxycarbonyl
DMSO: diemthyl sulfoxide
TFA: trifluoroacetic acid
DCM: dichloromethane
DCE: dichloroethane
DIEA: diisopropylethylamine
MeCN: acetonitrile
PyBrOP: tris(pyrrolidino)bromophosphonium hexafluorophosphate
TBTU or HATU: 2-(1H-benzotriazole-1-yl)-1,1,3,3-tetramethyluronium tetrafluoroborate
DMAP: 4-dimethylaminopyridine
PPTS: pyridinium p-toluenesulfonate
IBX: periodobenzoic acid
AIBN: 2,2'-azobisisobutyronitrile
rt: room temperature
ON: overnight
ND: not determined
MS: mass spectrometry
LC: liquid chromatography General Synthetic Methodology:

The compounds of this invention may be prepared in general by methods known to those skilled in the art. Schemes 1–17 below illustrate synthetic routes to the compounds of the present invention. Other equivalent schemes, which will be readily apparent to the ordinary skilled organic chemist, may alternatively be used to synthesize various portions of the molecule as illustrated by the general scheme below, and the preparative examples that follow.

Scheme 1:

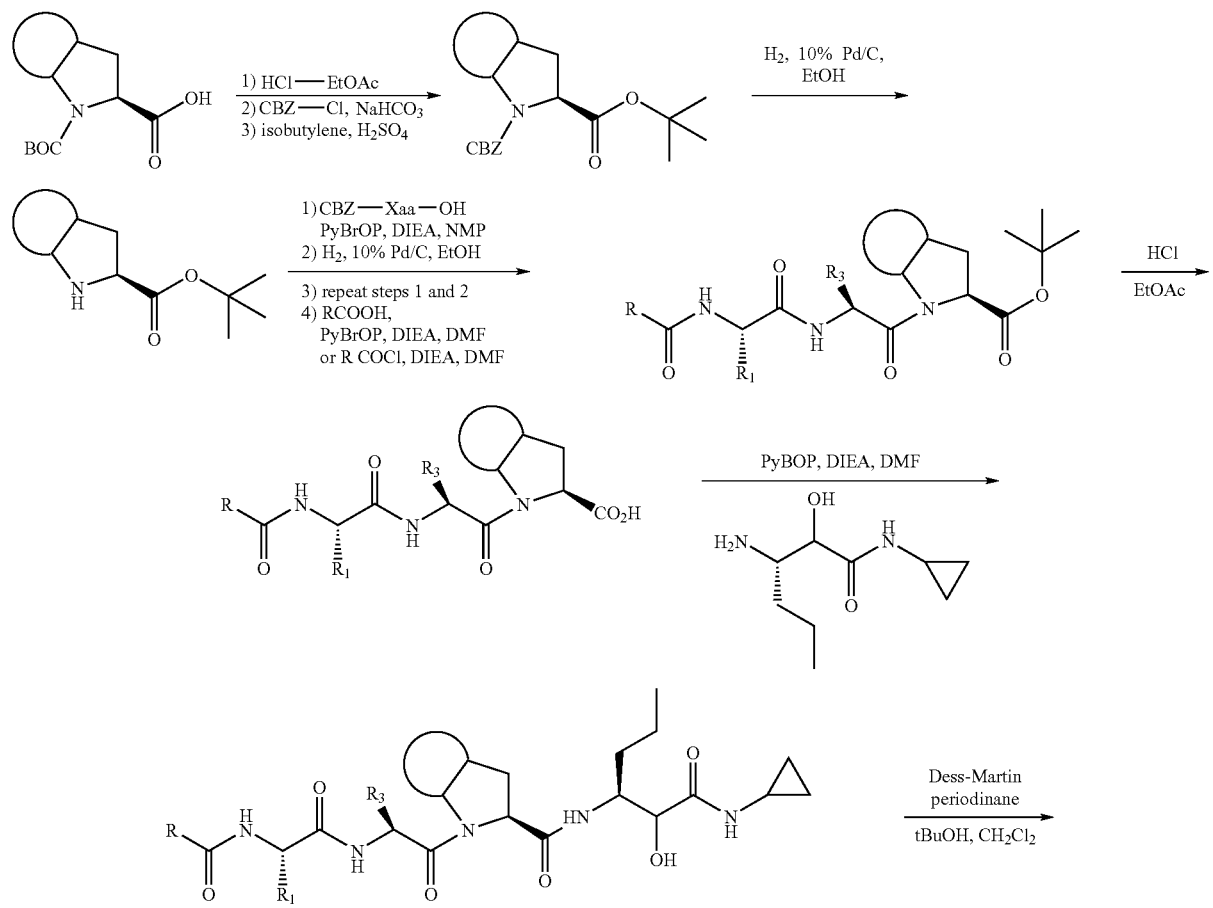

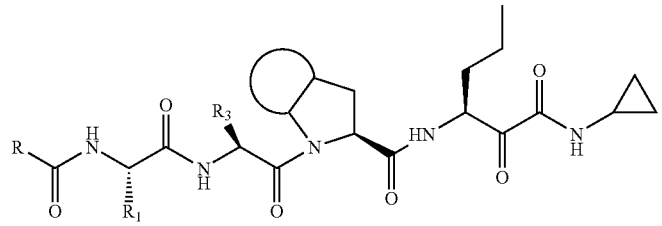
Scheme 1 above provides a general route for the preparation of compounds of formula I.
Schemes 2 above provides another general route for the preparation of compounds of formula I.
Scheme 2:
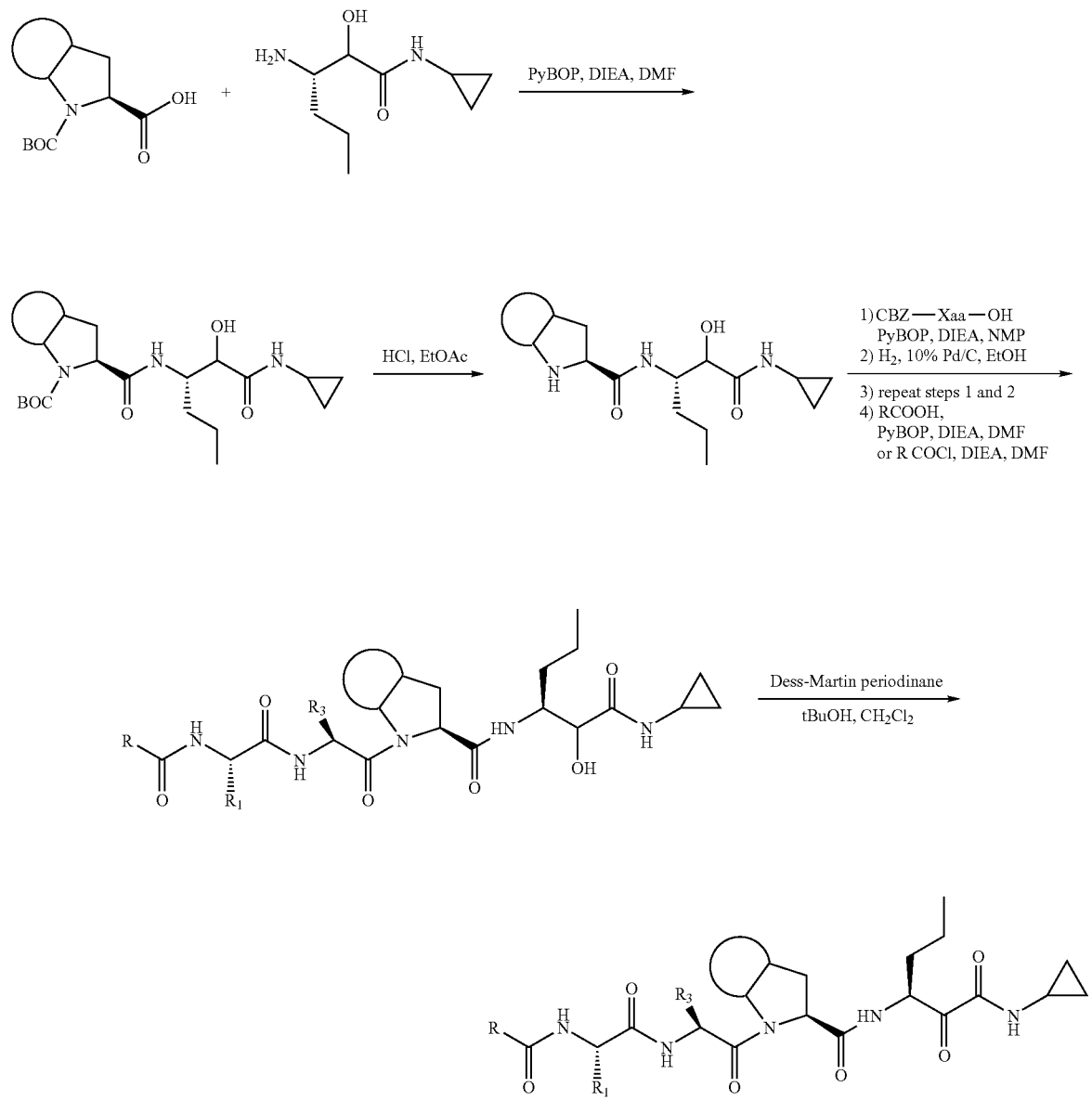

Scheme 3:
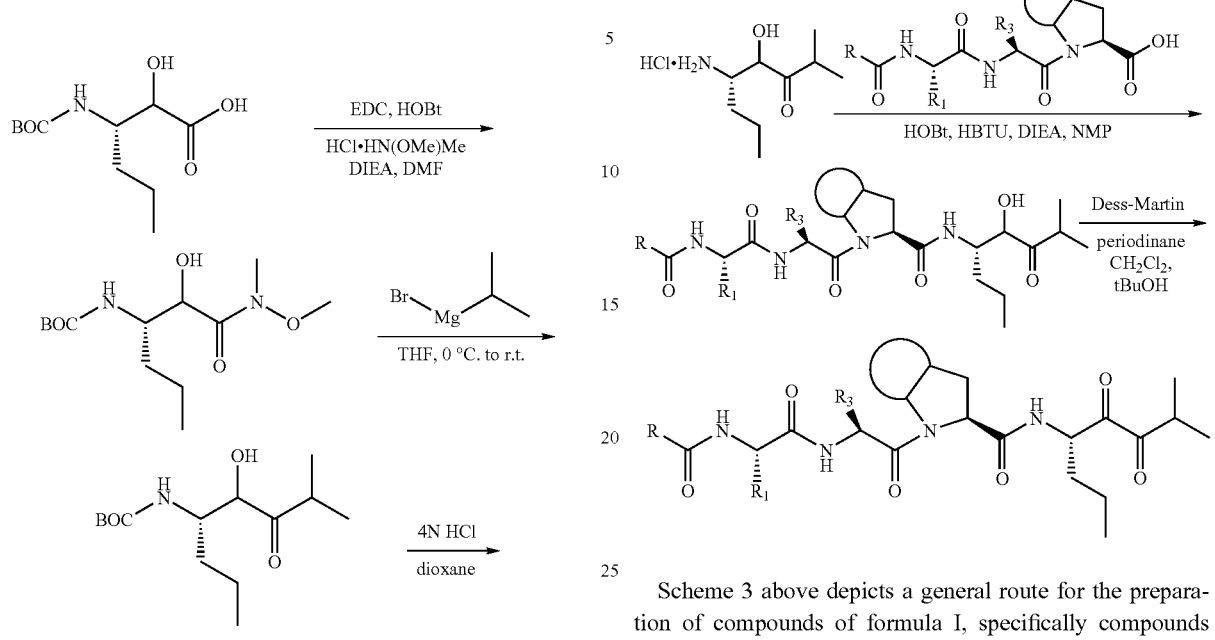
Scheme 3 above depicts a general route for the preparation of compounds of formula I, specifically compounds represented by structure 62a.
Scheme 4:
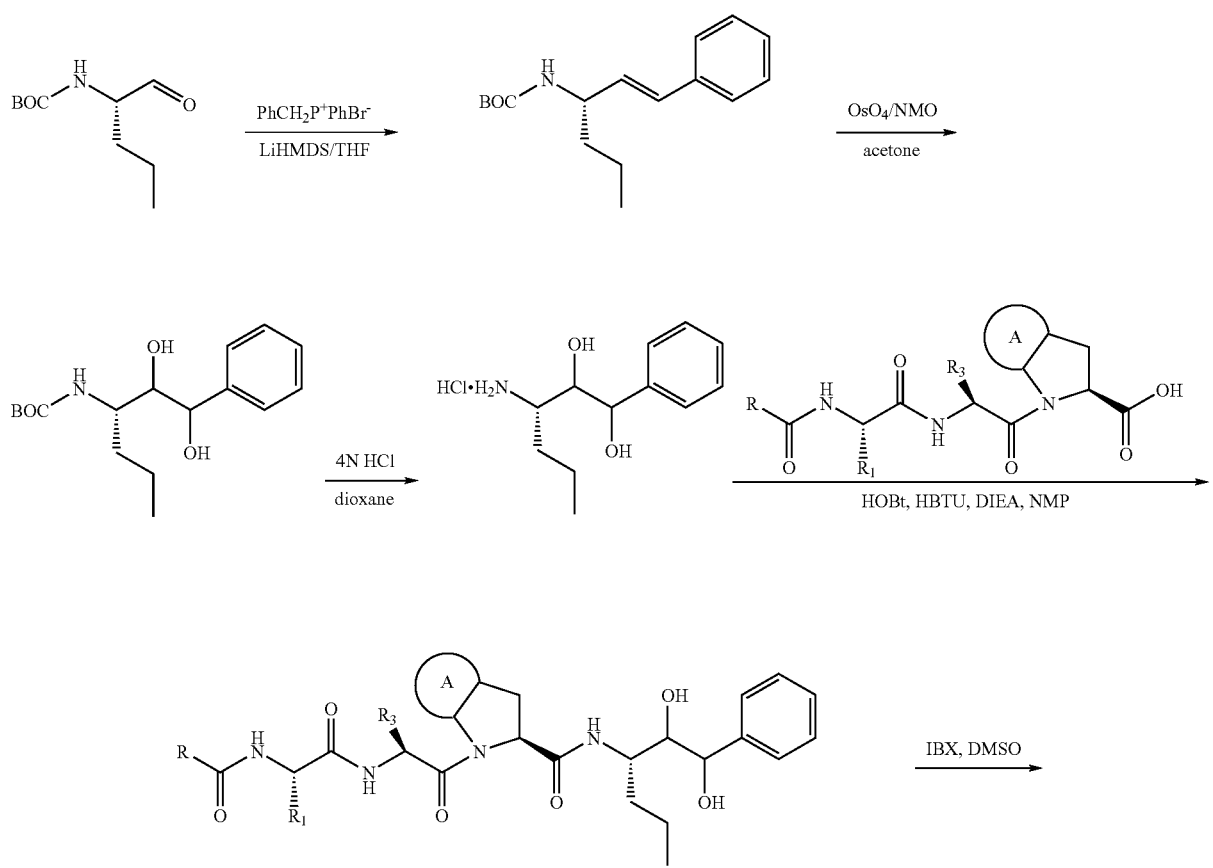

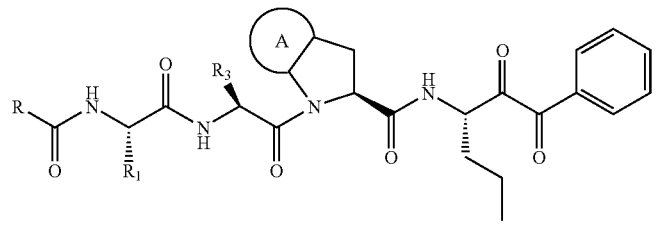
Scheme 4 above provides another method for the preparation of compounds of formula I.
Scheme 5:
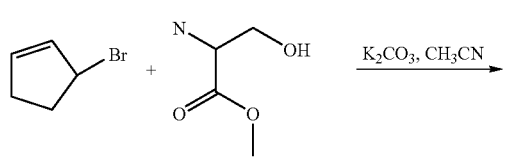
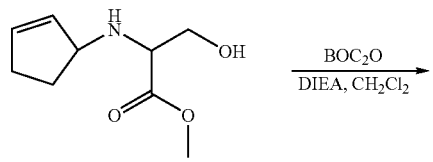
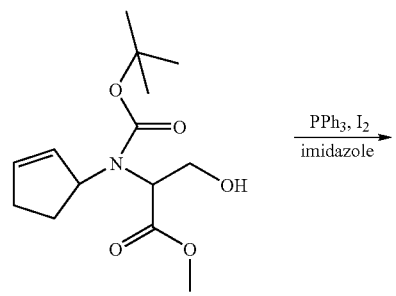
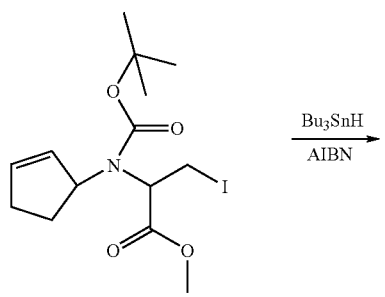
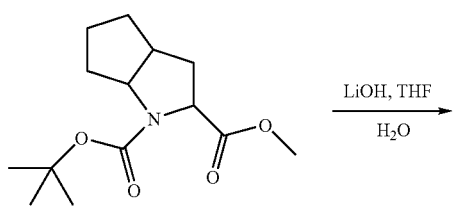
Scheme 1 or 2 in combination with scheme 5 above provide another general method for the preparation of compounds of formula I.
Scheme 6:
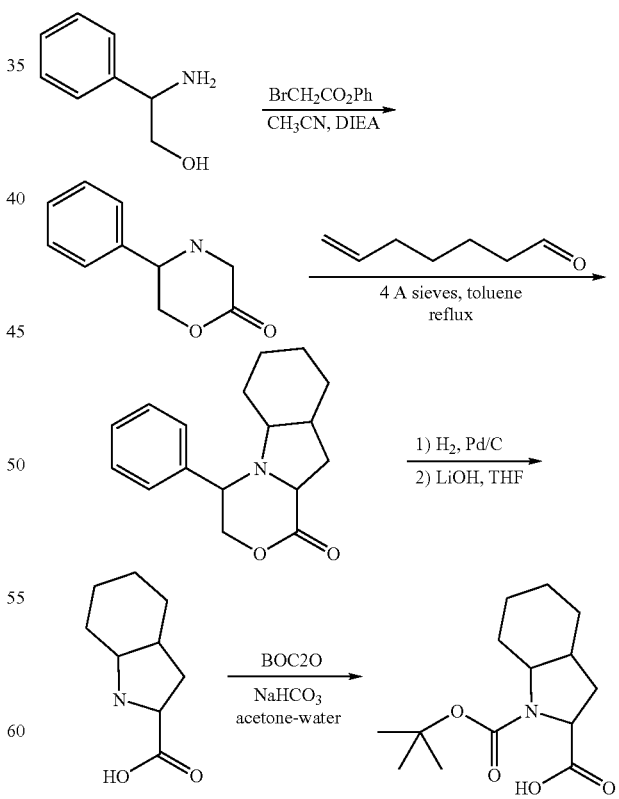
Scheme 1 or 2 in combination with scheme 6 above provide another general method for the preparation of compounds of formula I.

Scheme 7:

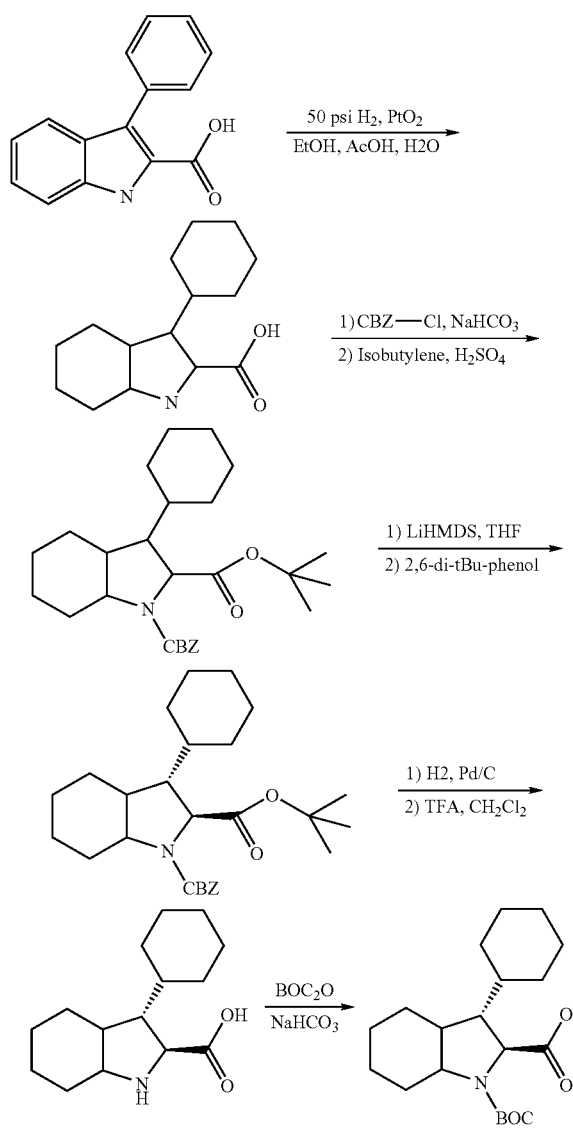

Scheme 1 or 2 in combination with scheme 7 above provide another general method for the preparation of certain compounds of formula I.

Scheme 8:

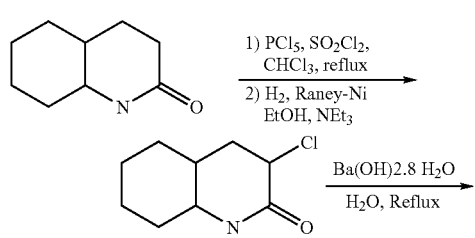

-continued

Scheme 1 or 2 in combination with scheme 8 above provide another general route for the preparation of compounds of formula I.

Scheme 9:

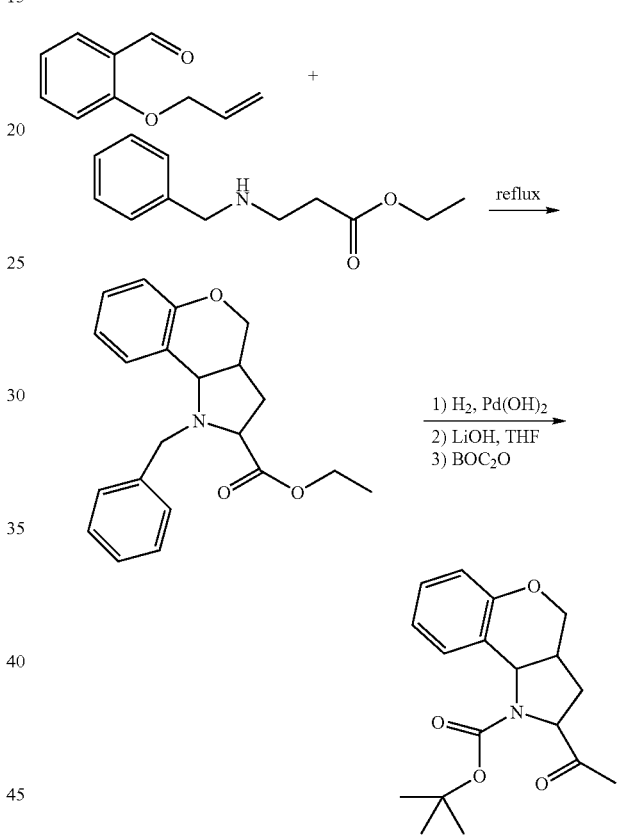

Scheme 1 or 2 in combination with scheme 9 above provide another general method for the preparation of certain compounds of formula I.

Scheme 10:

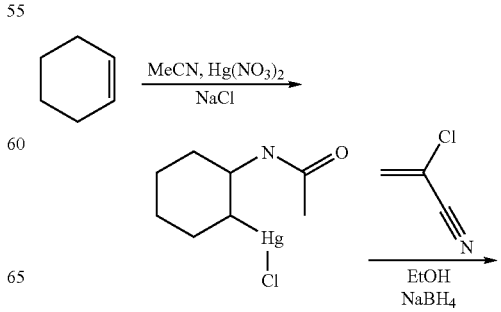

-continued

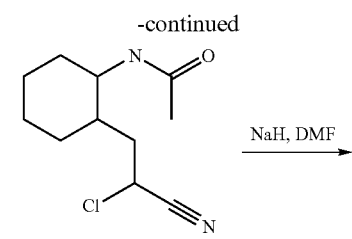

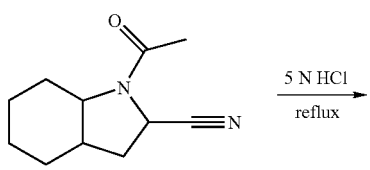

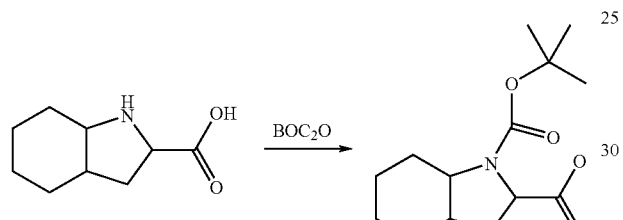

Scheme 1 or 2 in combination with scheme 10 above provide yet another general method for the preparation of compounds of formula I.

Scheme 11:

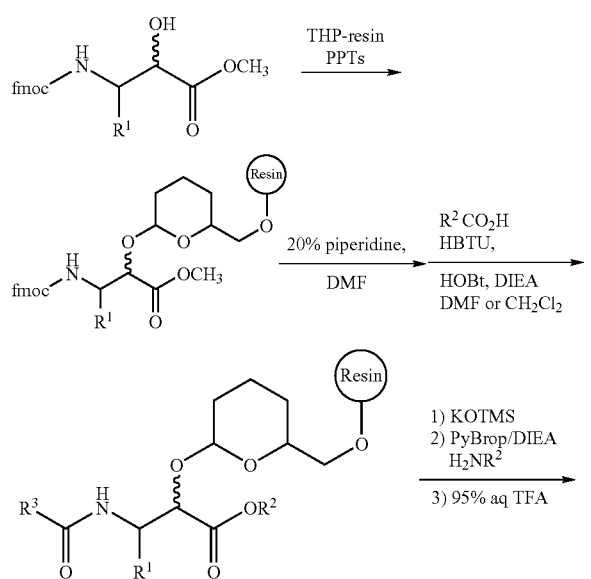

R3 = fully grown petidomimetic with cap installed

-continued

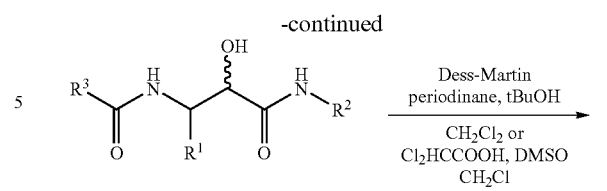

Scheme 11 above shows a general route for the preparation of compounds of formula I using a solid phase synthetic route based on the procedure of Ellman, J. et al., *J. Med. Chem.* 1995, 38, 1427.

Scheme 12:

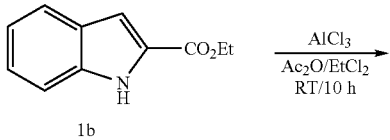

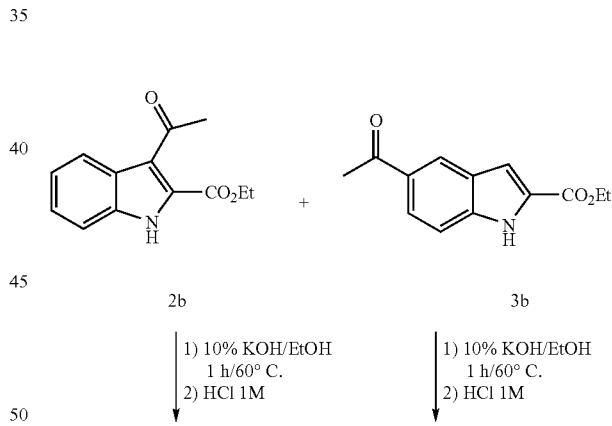

Scheme 1 or 2 in combination with scheme 11 above provide a general method for the preparation of compounds of formula I, specifically compounds 39, 40, 39a, and 40a.

Scheme 13:
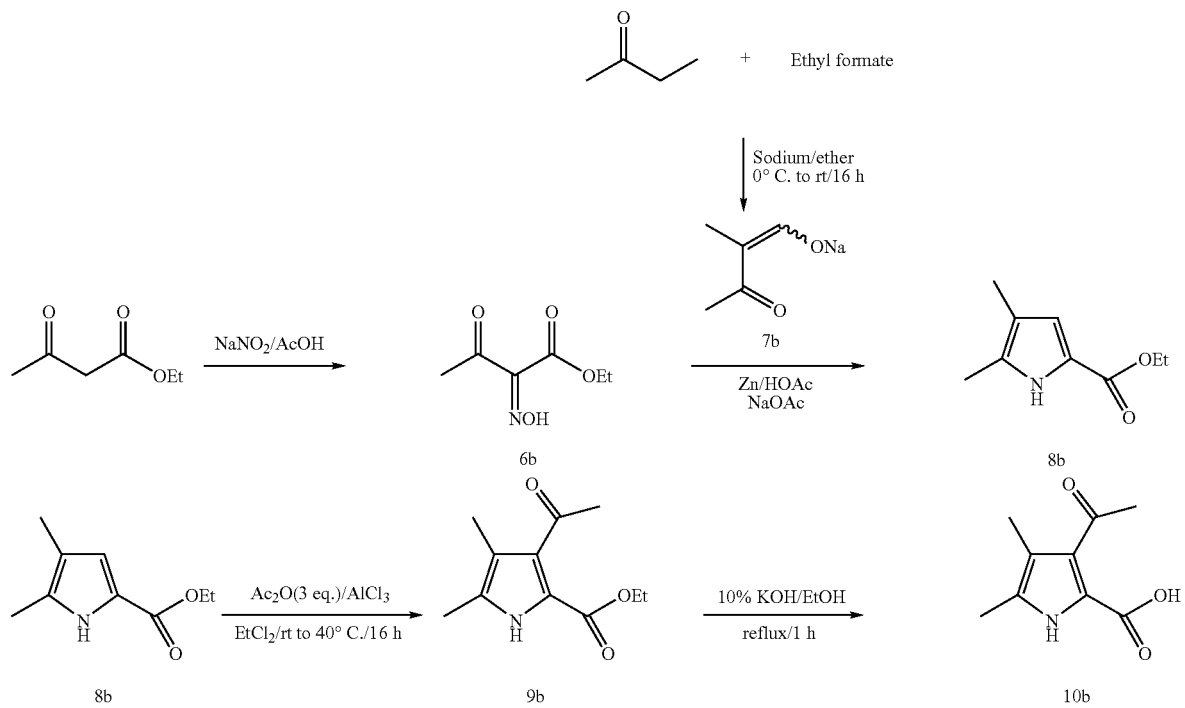
Scheme 1 or 2 in combination with scheme 13 above provide a general method for the preparation of compounds of formula I, specifically compounds 25, 25a, 41a, 45a, 55a, 58a, 59a, and 61a.
Scheme 14:
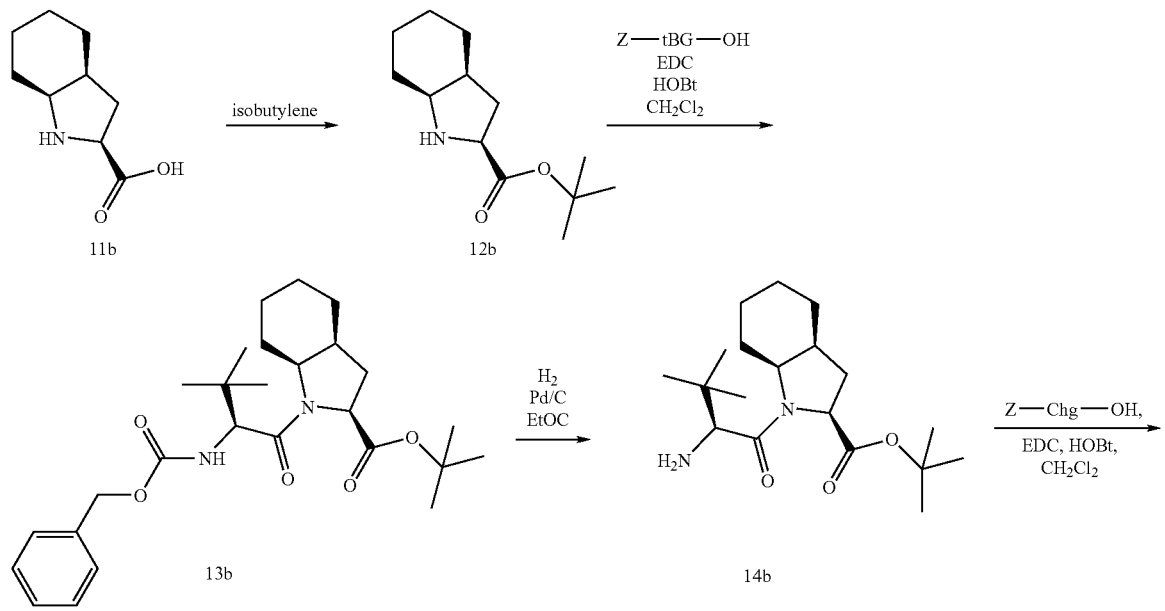

-continued
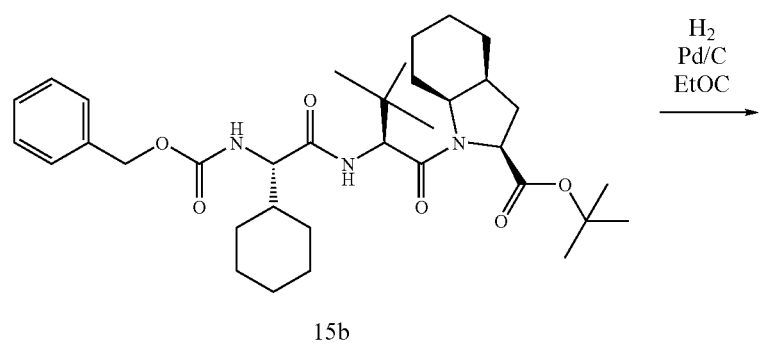
15b
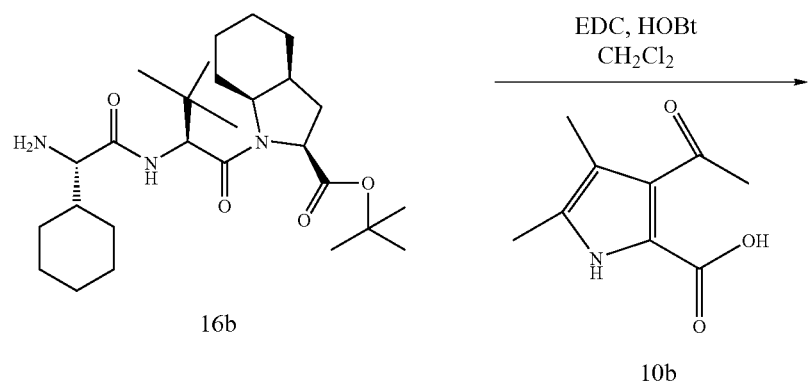
16b 10b
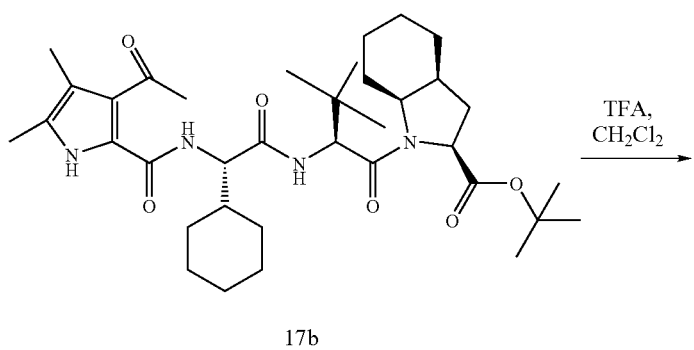
17b
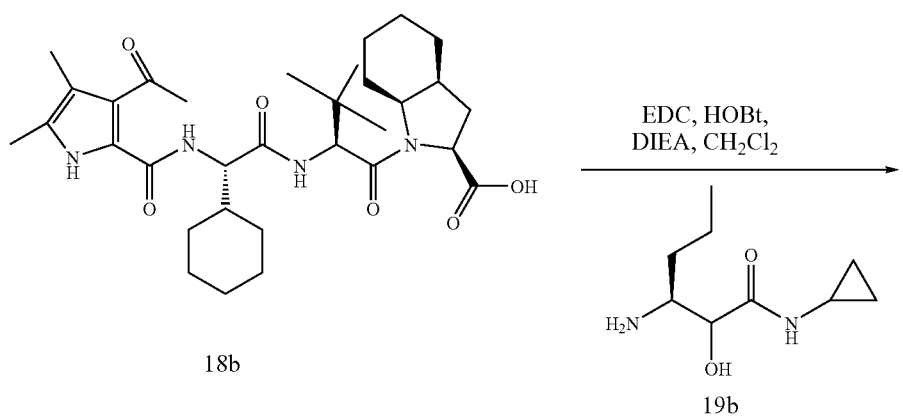
18b 19b

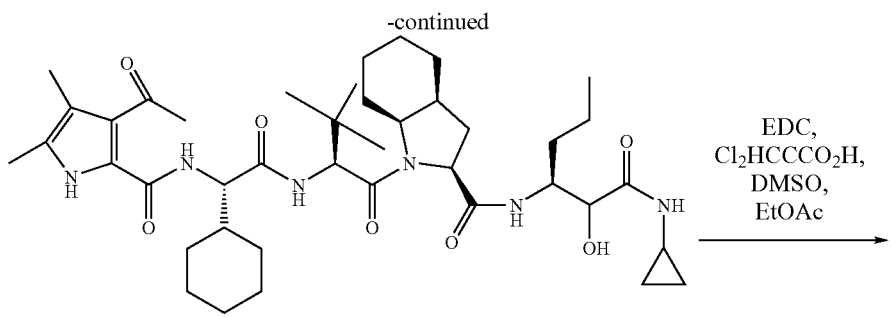
20b
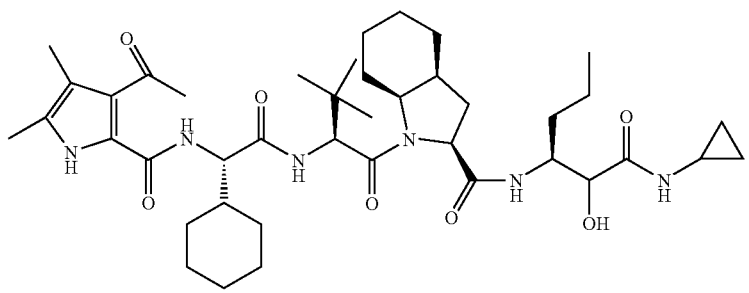
25a
Scheme 14 above provides a synthetic scheme for the preparation of compound 25a.
Scheme 15:
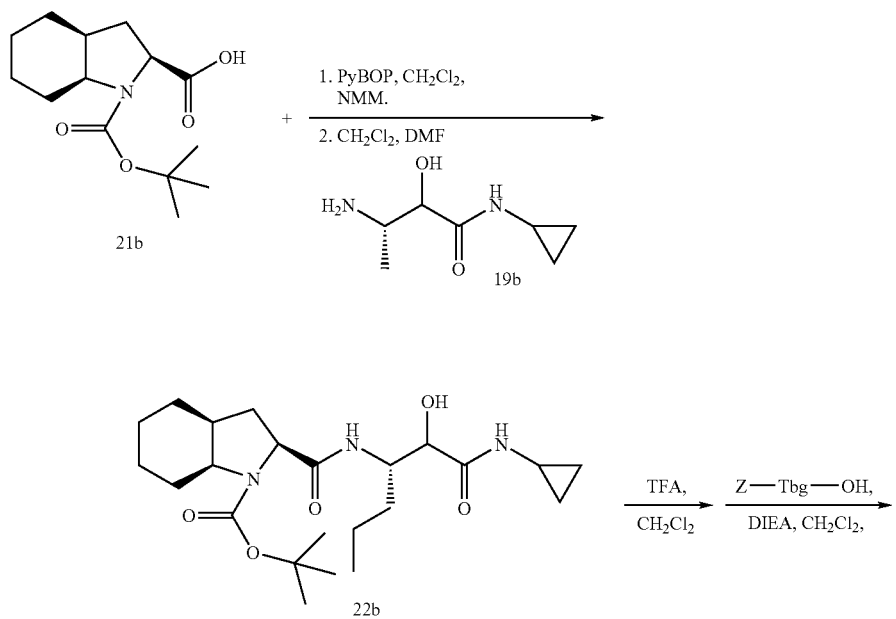

-continued
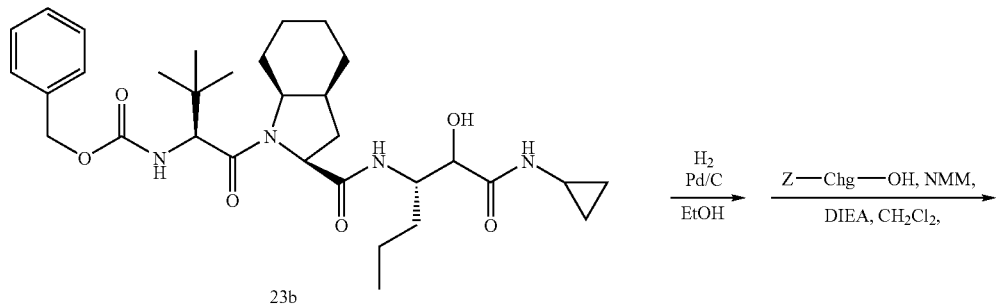
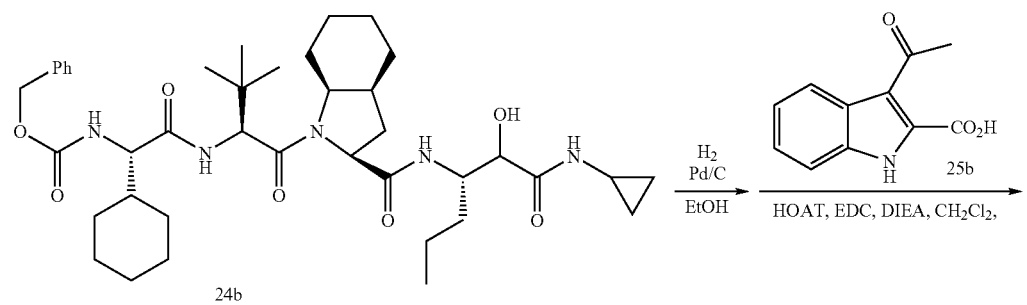
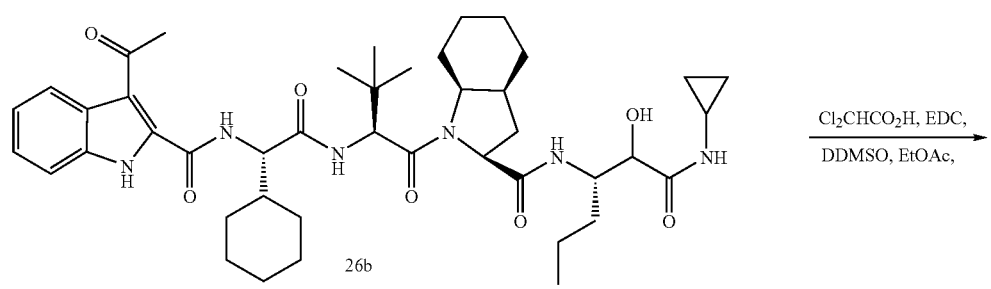
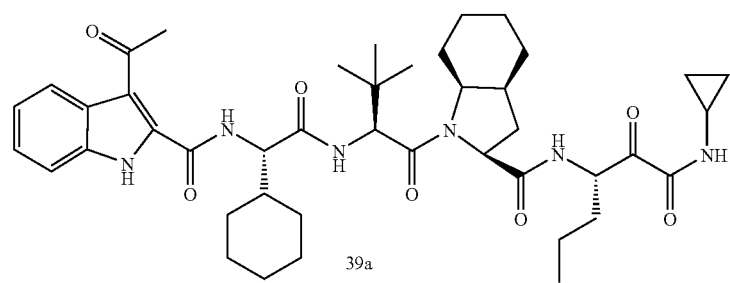

Scheme 15 above provides a synthetic scheme for the preparation of compound 39a.
Scheme 16:
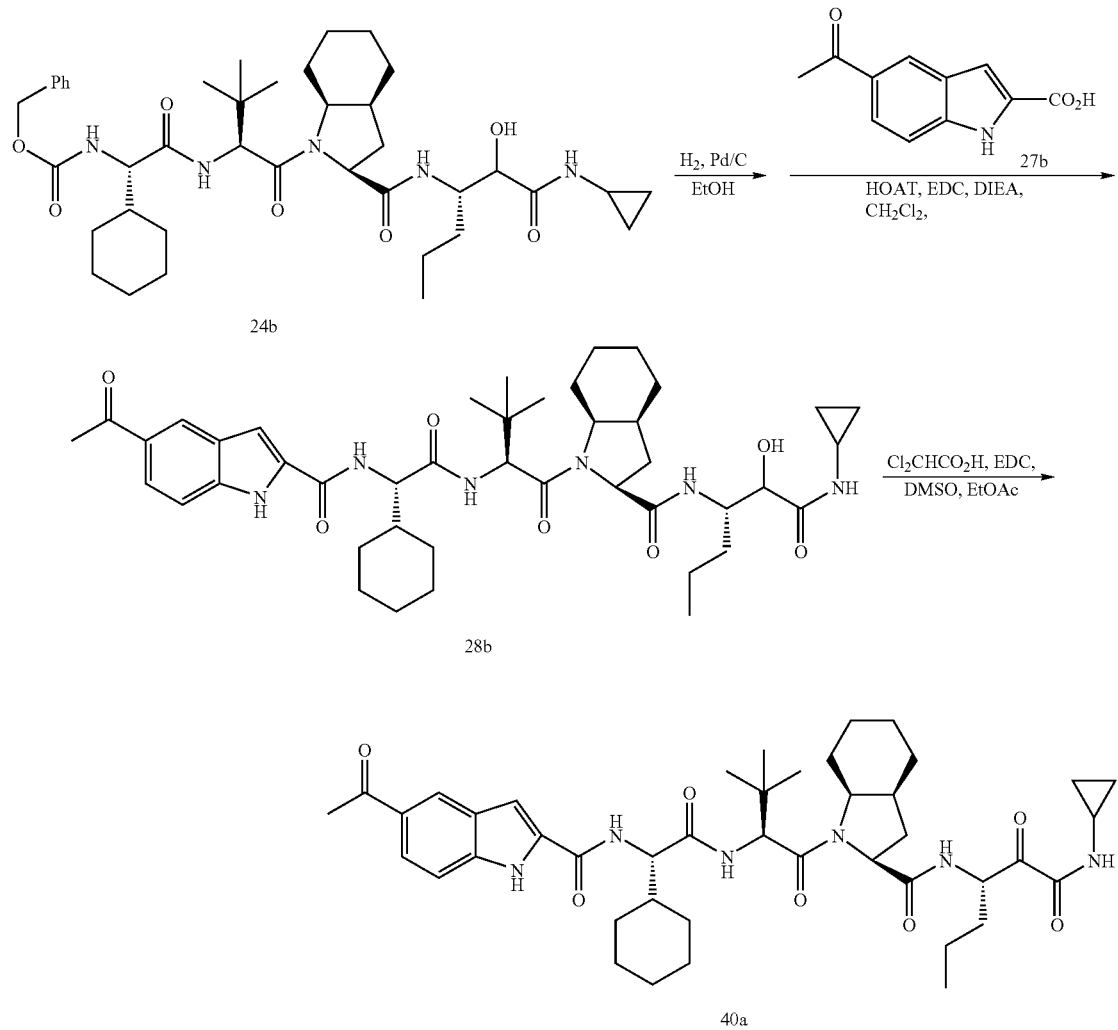
Scheme 16 above provides a synthetic scheme for the preparation of compound 40a.
Scheme 17:
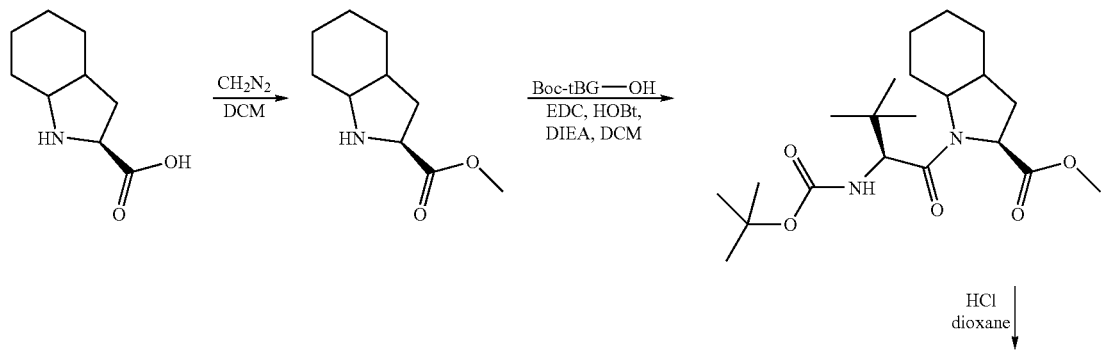

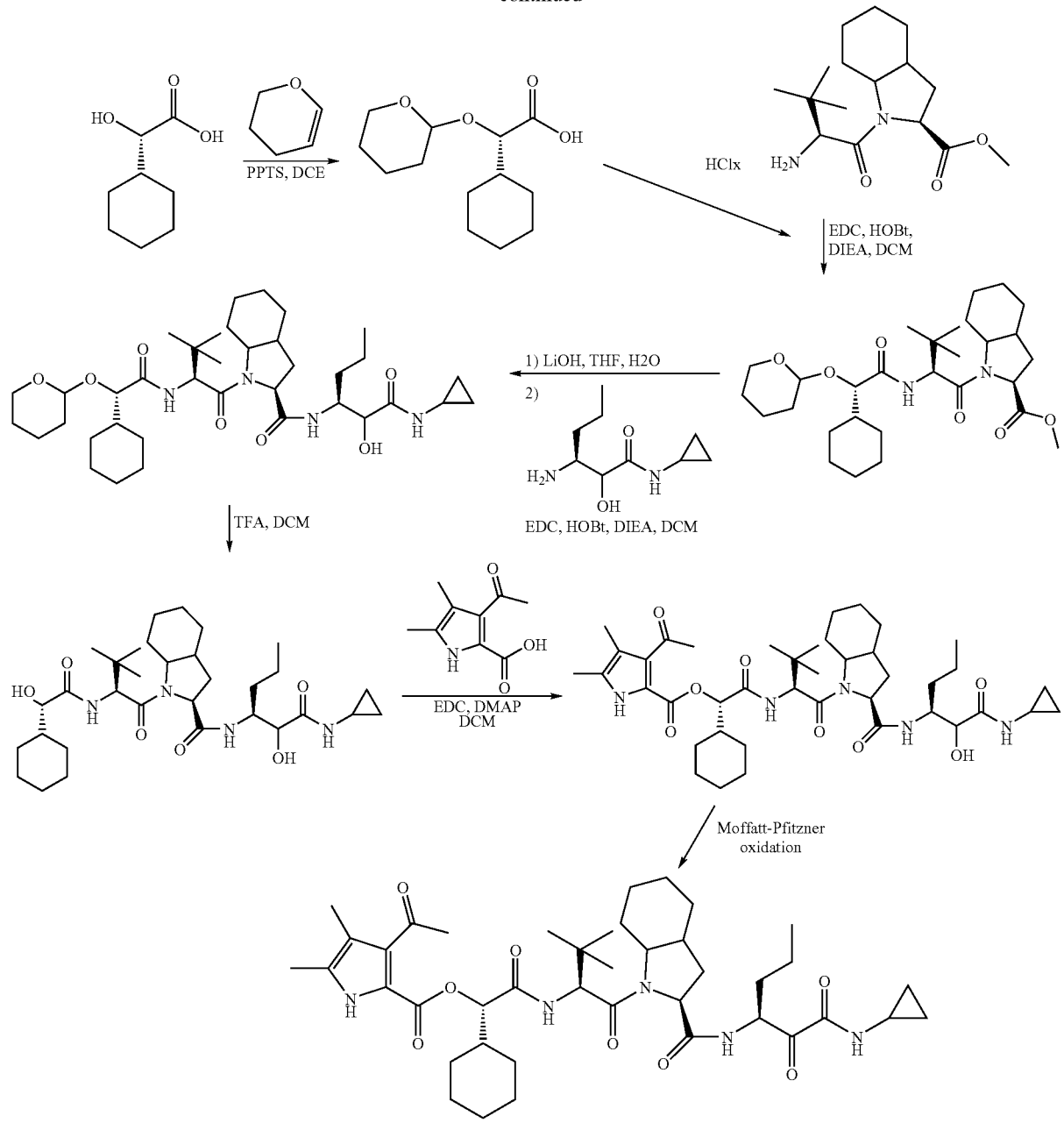

Scheme 17 above provides a general method for the preparation of compounds of formula II.

Although certain exemplary embodiments are depicted and described below, it will be appreciated that compounds of this invention can be prepared according to the methods described generally above using appropriate starting materials generally available to one of ordinary skill in the art.

Another embodiment of this invention provides a composition comprising a compound of formula I or a pharmaceutically acceptable salt thereof. According to a preferred embodiment, the compound of formula I is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I, II, III or IV, and one or more additional therapeutic or prophylactic agents, both the compound and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are pharmaceutical compositions formulated for oral administration.

In another embodiment, the compositions of this invention additionally comprise another anti-viral agent, preferably an anti-HCV agent. Such anti-viral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such anti-viral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments; laboratory instruments and garments; blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In order that this invention be more fully understood, the following examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_t$(min)" refers to the HPLC retention time, in minutes, associated with the compound. The HPLC retention times listed were either obtained from the mass spec. data or using the following method:
Instrument: Hewlett Packard HP-1050;
Column: YMC $C_{18}$ (Cat. No. 326289C46);
Gradient/Gradient Time: 10–90% $CH_3CN/H_2O$ over 9 minutes, then 100% $CH_3CN$ for 2 minutes;
Flow Rate: 0.8 ml/min;
Detector Wavelength: 215 nM and 245 nM;
Chemical naming for selected compounds herein was accomplished using the naming program provided by CambridgeSoft Corporations ChemDraw Ultra®, version 7.0.1.

Example 1

3-Acetyl-1H-indole-2-carboxylic acid (4b) and 5-Acetyl-1H-indole-2-carboxylic acid (5b).

Aluminum chloride (7.75 g, 0.058 mol) was suspended in 200 ml of anhydrous dichloroethane at room temp. followed by a slow addition of acetic anhydride (2.74 mL, 0.03 mol). The mixture was stirred at room temp for 10 minutes after which, 1H-indole-2-carboxylic acid ethyl ester (1b, 5.0 g, 0.0264 mol) was added as a solution in 15 mL of dichloroethane. The reaction mixture was stirred under nitrogen at 40° C. for 10 h. The reaction was quenched with an ice-water mixture and the organic layer was washed with water (3×). The organic phase was dried over anh. $Na_2SO_4$, filtered and concentrated in vacuo. Chromatography on $SiO_2$ (4% Ethyl acetate/96% $CH_2Cl_2$) provided 3.2 g of 3-acetyl-1H-indole-2-carboxylic acid ethyl ester 2b (52%) and 770 mg of 5-acetyl-1H-indole-2-carboxylic acid ethyl ester 3b (13%).

2b: $^1$H NMR (CDCl$_3$) d 9.1 (bs,1H), 8.1 (d,1H), 7.5 (m,2H), 7.3 (s,1H), 4.4 (q,2H), 2.7 (s,3H), 1.5 (t,3H) ppm.
3b: $^1$H NMR (CDCl$_3$) d 9.3 (bs,1H), 8.25 (s,1H), 8.1 (d,1H), 7.6 (d,1H), 7.2 (s,1H), 4.3 (q,2H), 2.7 (s,3H), 1.7 (t, 3H) ppm.

Saponification of 2b and 3b with 10% KOH in ethanol at 60° C. for 1 h followed by acidification with 1M HCl provided 3-acetyl-1H-indole-2-carboxylic acid 4b and 5-acetyl-1H-indole-2-carboxylic acid 5b in 95% and 93% yield respectively. The crude acids were used directly without purification in the next step.

Example 2

3-Acetyl-4,5-dimethyl-2-pyrrole carboxylic acid (10b).

A solution of sodium nitrite (36.9 g, 0.534 mol) in 70 mL of water was added dropwise to a stirred solution of ethylacetoacetate (70 g, 0.538 mol) in 1401 mL of glacial acetic acid at 0° C. After the addition was complete, the light yellow reaction mixture was allowed to warm to room temperature. After 30 minutes, all the starting material had been consumed, the reaction was quenched with 350 mL of water and extracted with ethyl acetate (2×125 mL). The organic extracts were combined and washed with water (2×125 mL) and saturated sodium hydrogen carbonate aqueous solution (2×10$^5$ mL). The organic layer was dried with sodium sulfate and concentrated in vacuo to give 84.2 g (98%) of Ethyl-2-Hydroxyimino-3-oxobutanoate 6b as a pale yellow oil.

$^1$H NMR (CDCl$_3$) d 10.3 (s,1H), 4.2 (q,2H), 2.3 (s,3H), 1.3 (t, 3H) ppm.

Crushed sodium (12.4 g, 0.540 mol) was added to a solution of 2-butanone (48.2 mL, 0.538 mol) and ethyl formate (43.47 mL, 0.538 mol) in dry ether (540 mL) with vigorous mechanical stirring over a period of 1 h, during which time the mixture was chilled in an ice-salt bath. The mixture was then stirred at room temp. for 14 h. After cooling the reaction mixture to 4° C. for a few hours, the precipitated sodium salt was obtained by filtration and washed thoroughly with cold, dry ether to afford 49.3 g (75%) of the desired sodium salt of 2-Methy-3-oxobutyraldehyde 7b.

$^1$H NMR (DMSO-d$_6$) d 9.1 (s,1H), 1.9 (s,3H), 1.3 (s,3H) ppm.

Sodium salt 7b (49.3 g, 0.404 mol) and oxime 6b (64.23, 0.404 mol) were stirred in 300 mL of 70% acetic acid/30% water and warmed to 50° C. Zinc powder (42.21 g, 0.646 mol) was added portion-wise over 30 minutes maintaining the temperature below 100° C. When the addition was complete, the suspension was refluxed for 15 minutes, then poured into 4 L of ice-water. After a short time, the product precipitated out to give, after filtration, 30.1 g (45%) of the desired ethyl-4,5-dimethyl-2-pyrrole carboxylate 8b. $^1$H NMR (CDCl$_3$) d 9.0 (bs,1H), 6.7 (s,1H), 4.3 (q,2H), 2.3 (s, 3H), 2.0 (s,3H), 1.3 (t,3H) ppm.

To a solution of aluminum chloride (50.19 g, 0.376 mol) in dry dichloroethane (580 mL) at 25° C. was added slowly acetic anhydride (17.75 mL, 0.188 mol). The resulting mixture was stirred at room temp. for 10 minutes, then a solution of pyrrole 8b (10.49 g, 0.0627 mol) in dichloroethane (30 mL) was added and the reaction mixture was stirred at room temp. for 2 h. After an additional 3 h at 80° C., the mixture was poured into ice water and extracted with dichloromethane. The organic layer was dried with anhy. sodium sulfate and concentrated in vacuo to an orange residue. Short plug filtration over silica gel (30% ethyl acetate/70% hexanes) gave 7.5 g (60%) of ethyl-3-acetyl-4,5-dimethyl-2-pyrrole carboxylate 9b.

$^1$H NMR (CDCl$_3$) d 9.0 (bs,1H), 4.3 (q,2H), 2.7 (s,3H), 2.1 (s, 3H), 1.9 (s,3H), 1.3 (t,3H) ppm.

A mixture of pyrrole ester 9b (8.2 g, 0.0392 mol), in ethanol and 100 mL of 10% potassium hydroxide were refluxed for 1 h. The mixture was cooled and concentrated in vacuo to an oil. Water was added to the oil, the mixture acidified with dilute HCl and extracted with ether. The organic phase was dried with anhy. sodium sulfate and concentrated in vacuo to a solid residue. The compound was recrystallized in 80 mL of ethanol to give 5.8 g of pure 3-acetyl-4,5-dimethyl-2-pyrrole carboxylic acid 10b as a solid.

$^1$H NMR (DMSO-d$_6$) d 2.5 (s,3H), 2.2 (s,3H), 2.0 (s,3H) ppm.

Example 3

1-(2-{20[(3-Acetyl-4,5-dimethyl-1H-pyrrole-1H-2-carbonyl)-amino]-2-cyclohexyl-acetylamino}-3,3-dimethyl-butyryl)-octahydro-indole-2-carboxylic acid (1-cyclopropylaminooxalyl-butyl)-amide (25a).

Octahydro-indole-2-carboxylic acid 11b (5.0 g, 29.5 mmol, purchased from Bachem) was suspended in 200 mL of $CHCl_3$ then cooled in a dry ice/acetone bath. $H_2SO_4$ (120 uL/mmol) was added followed by bubbling in excess isobutylene. The mixture was sealed and the ice bath removed. The mixture was stirred at RT for 12 hours. The reaction mixture was carefully unsealed after cooling and concentrated. EtOAc was added and washed with saturated sodium bicarbonate soln, brine, dried over sodium sulfate, then filtered and concentrated to give octahydro-indole-2-carboxylic acid tert-butyl ester 12b (6.65 g, 29.5 mmol, 100%).

$^1$H-NMR ($CDCl_3$) d 1.22 (2H,m), 1.38 (2H,m), 1.48 (9H,s), 1.50 (2H,m), 1.66 (2H,m), 1.71 (1H,m), 2.02, (1H m), 2.18 (1H, m), 2.85 (1H,bs), 3.10 (1H m), 3.70 (1H,dd) ppm.

L-CBz-tert-butyl glycine (5.0 g, 11.2 mmol) was stirred in $CH_2Cl_2$ (40 mL). EDC (2.25 g, 11.7 mmol) and HOBt (1.58 g, 11.7 mmol) were added and the mixture stirred 15 minutes. This solution was cannulated into a solution of 12b (2.4 g, 10.6 mmol) in $CH_2Cl_2$ (20 mL) and stirred overnight. The reaction was monitored by HPLC observing the consumption of the amine. The mixture was concentrated, EtOAc added, followed by a 1.0N aqueous glycine sodium salt solution and the mixture stirred until all Cbz-tert-butyl glycine-OBt was consumed. The layers were separated and the organic phase washed with 1N HCl (3×), brine, 10% potassium carbonate (3×), and brine then dried over sodium sulfate, filtered and concentrated in vacuo. Chromatography through a silica gel plug (10%EA/Hex) gave 1-(2-benzyloxycarbonylamino-3,3-dimethyl-butyryl)-octahydro-indole-2-carboxylic acid tert-butyl ester 13b (4.4 g, 9.3 mmol, 88%).

$^1$H-NMR ($CDCl_3$) d 1.05 (9H,s), 1.30 (2H,m), 1.46 (9H, s), 1.50–1.72 (5H,m), 1.94–2.10 (3H,m), 2.30 (1H m), 4.18 (1H, m), 4.22, (1H,d), 4.28 (1H,dd), 5.05–5.17 (2H,dd), 5.30 (1H,d), 7.33 (5H,m) ppm.

Ester 13b (4.0 g, 8.4 mmol) was stirred in EtOH (40 mL) charged with 400 mg 10%Pd(OH)$_2$/C. H$_2$ gas was bubbled into the suspension until the reaction was complete. Catalyst was removed by filtration and the filtrate concentrated in vacuo to give 1-(2-amino-3,3-dimethyl-butyryl)-octahydro-indole-2-carboxylic acid tert-butyl ester 14b (2.8 g, 8.4 mmol, 100%) which was used as is in the next step without further purification.

$^1$H-NMR (CDCl$_3$) 3:2 ratio of rotamers, d 0.98 and 1.02 (9H, pair of singlets), 1.20–1.34 (2H,m), 1.47 and 1.50 (9H, pair of singlets), 1.58–1.78 (6H,m), 1.99 (1H,m), 2.1 (1H, m), 2.3 (1H,m), 2.4 (1H,m), 3.86 and 4.13 (1H,m), 4.32 (1H, m) ppm.

L-CBz-cyclohexyl glycine (3.0 g, 10.3 mmol) in $CH_2Cl_2$ (30 mL) was treated with EDC (2.07 g, 10.8 mmol) and HOBt (1.65 g, 10.8 mmol) and stirred for 15 minutes. The resulting mixture was added to a solution of 14b (3.32 g, 9.8 mmol in $CH_2Cl_2$ (20 mL) and stirred at RT, monitoring consumption of amine by HPLC. 1.0N glycine sodium salt solution was added until all L-CBz-cyclohexyl glycine-OBt was consumed (several hours) with monitoring by HPLC. The reaction mixture was washed with 1.0N HCl (3×), brine, 10% potassium carbonate (3×), and brine, then dried over sodium sulfate, filtered and concentrated in vacuo. The solid product obtained was recrystallized from hot IPA/H$_2$O (~3.3:1) by dissolving the compound in hot IPA and adding water slowly until product started to precipitate out. Cold filtration afforded 4.79 g (80%) of 1-[2-(2-benzyloxycarbonylamino-2-cyclohexyl-acetylamino)-3,3-dimethyl-butyryl]-octahydroindole-2-carboxylic acid tert-butyl ester 15b as a solid.

$^1$H-NMR (CDCl$_3$) d 0.98 (1H,m), 1.03 (9H,s), 1.12–1.32 (5H, m), 1.43 (9H,s), 1.59–1.79 (12H,m), 1.93–2.10 (3H,m), 2.20 (1H,m), 3.98 (1H,m), 4.12 (1H,m), 4.22 (1H m) 4.55 (1H,d), 5.10 (2H,m), 5.27 (1H,d), 6.25 (1H,d), 7.35 (5H,m) ppm.

CBz ester 15b (3.0 g, 4.9 mmol) was stirred in EtOH (25 mL) and charged with 300 mg 10%Pd(OH)$_2$/C. H$_2$ gas was bubbled into the suspension until the reaction was complete. Catalyst was removed by filtration and the filtrate concentrated in vacuo to give 1-[2-(2-amino-2-cyclohexyl-acetylamino)-3,3-dimethyl-butyryl]-octahydro-indole-2-carboxylic acid tert-butyl ester 16b (2.34 g, 4.9 mmol, 100%) which was used as is in the next step without further purification.

$^1$H-NMR (CDCl$_3$) d 1.08 (9H,s), 1.10–1.25 (7H,m), 1.44 (9H, s), 1.50–1.78 (10H,m), 1.94 (2H,m), 2.07 (2H,m), 2.30 (1H, m), 3.21 (1H,m), 4.22 (1H,m). 4.34 (1H,m), 4.52 (1H,d), 8.04 (1H,d) ppm.

3-acetyl-4,5-dimethyl-2-pyrrole carboxylic acid 10b (2.5 g, 13.7 mmol) in DMF (56 mL) was treated with EDC (2.75 g, 14.4 mmol) and HOBt (2.20 g, 14.4 mmol) and stirred at RT for 15 minutes. Amine 16b (6.23 g, 13.0 mmol) in DMF (10 mL) was added, the reaction mixture stirred at RT and monitored by HPLC. The mixture was concentrated in vacuo, then dissolved in EtOAc. 1.0N glycine sodium salt aqueous solution was added until all excess amino ester 16b was consumed (several hours). The mixture was washed with 1N HCl (3×), brine, bicarb (3×), and brine, then dried over sodium sulfate, filtered, and concentrated in vacuo. Purification through a short plug of silica gel (25%EA/Hex) afforded 7.08 g, (85%) of 1-(2-{2-[(3-acetyl-4,5-dimethyl-1H-pyrrole-2-carbonyl)-amino]-2-cyclohexyl-acetylamino}-3,3-dimethyl-butyryl)-octahydro-indole-2-carboxylic acid tert-butyl ester 17b.

$^1$H-NMR (CDCl$_3$) d 0.94 (9H,s), 0.99–1.33 (6H,m), 1.42 (9H, s), 1.45–2.22 (16H,m), 2.24 (3H,s), 2.28 (3H,s), 2.55 (3H, s), 4.30 (1H,m), 4.39 (1H,m), 4.73 (1H,d), 5.00 (1H,m), 11.30 (1H,d) ppm.

tert-Butyl ester 17b (3.0 g, 4.68 mmol) was stirred in $CH_2Cl_2$ (20 mL) in an ice bath and TFA (20 mL) was added slowly. The mixture was warmed to RT and stirred until ester was no longer observed by HPLC. Added toluene and concentrated in vacuo several times (3×). Most of the residual TFA was removed in vacuo to give 1-(2-{2-[(3-acetyl-4,5-dimethyl-1H-pyrrole-2-carbonyl)-amino]-2-cyclohexyl-acetylamino}-3,3-dimethyl-butyryl)-octahydro-indole-2-carboxylic acid tert-butyl ester 18b as a pink solid which was used in the next step without further purification.

Crude acid 18b from above in $CH_2Cl_2$ (20 mL) was treated with DIEA dropwise and stirred at RT until fuming ceased (from quenching excess TFA). EDC (0.99 g, 5.1 mmol) and HOBt (0.78 g, 5.1 mmol) were added and the mixture stirred for 15 minutes. 3-Amino-2-hydroxy-hexanoic acid cyclopropylamine 19b (950 mg, 5.1 mmol, prepared according to the methods described by U. Schoellkopf et al., *Justus Liebigs Ann. Chem.* GE, 1976, 183–202, and J. Stemple et al., *Organic Letters* 2000, 2(18), 2769–2772) in $CH_2Cl_2$ (10 mL) was added and the mixture stirred at RT overnight. The mixture was poured onto 1N HCl/EtOAc, the organic layer washed with 1N HCl (3×), brine, sat'd NaHCO$_3$ (3×), and brine, then dried over sodium sulfate, filtered, and concentrated in vacuo. Purification through a plug of silica gel eluting with 100% CH$_2$Cl$_2$-->>1% MeOH/CH$_2$Cl$_2$-->>>2% MeOH/CH$_2$Cl$_2$ afforded 3.0 g (85% for two steps) of 1-(2-{2-[(3-acetyl-4,5-dimethyl-1H-pyrrole-2-carbonyl)-amino]-2-cyclohexyl-acetylamino}-3,3-dimethyl-butyryl)-octahydro-indole-2-carboxylic acid[1-(cyclopropylcarbamoyl-hydroxy-methyl)-butyl]-amide 20b.

NMR $^1$H-NMR (CDCl$_3$) d 0.50 (2H,m), 0.67 (1H,m), 0.75 (1H,m), 0.85 (4H,m), 0.93 (8H,m), 1.03 (3H,m), 1.22 (2H,m), 1.30 (3H,m), 1.50–2.03 (18H,m), 2.25 (3H,s), 2,26 (3H,s), 2.60 (3H,s), 2.71 (1H,m), 3.89 and 3.91 (1H,bm), 4.10 and 4.21 (1H, pair of singlets), 4.38 (1H,m), 4.52 (1H,m), 4.67 and 4.71 (1H, pair of doublets), 4.80 (1H,m), 6.95 and 7.00 (1H, pair of doublets) ppm.

To a solution of EDC (38.2 g. 199.2 mmol) in dry EtOAc (98 mL) was added keto-alcohol 20b (10.0 g, 13.3 mmol) in dry EtOAc (52 mL). Dry DMSO (75 mL) was added, the mixture cooled to 7° C. and dichloroacetic acid (10.97 mL, 133 mmol) in dry EtOAc (31 mL) was added as quickly as possible allowing the temperature to go no higher than 25° C. The ice bath was removed and the mixture stirred for 15 minutes. TLC showed complete disappearance of 20b. The mixture was cooled to 15° C. before adding 1.0N HCl (200 mL) to quench as quickly as possible without allowing the temp. to go above 25° C. The organic layer was washed with water (3×), dried over sodium sulfate, filtered and concentrated in vacuo. Purification through a silica gel plug (100% CH$_2$Cl$_2$-->50%EtOAc/CH$_2$Cl$_2$) afforded a white solid which was stirred in Et$_2$O, filtered and dried in vacuo to remove residual dimethyl sulfide and dichloroacetic acid. Obtained 7.49 g (75%) of desired 1-(2-{2-[(3-acetyl-4,5-dimethyl-1H-pyrrole-2-carbonyl)-amino]-2-cyclohexyl-acetylamino}-3,3-dimethyl-butyryl)-octahydro-indole-2-carboxylic acid (1-cyclopropylaminooxalyl-butyl)-butyl)-amide 25a.

$^1$H-NMR (CDCl$_3$) d 0.61 (2H,m), 0.82 (2H,d), 0.91 (3H,t), 0.97 (7H,s), 1.05 (3H,m), 1.20 (2H,m), 1.32 (4H,m), 1.50 (5H,m), 1.68 (5H,m), 1.79 (3H,m), 1.89 (3H,m), 2.01 (1H, m), 2.18 (1H,m), 2.23 (3H,s), 2.24 (3H,s), 2.37 (1H,m), 2.59 (3H,s), 2.78 (1H,m), 4.41 (1H,m), 4.56 (1H,t), 4.85 (1H,d), 4.91 (1H,m), 5.31 (1H,m), 6.90 (1H, broad), 7.03 (1H, broad) ppm.

Example 4

3-Acetyl-1H-indole-2-carboxylic acid (cyclohexyl-{1-[2-(1-cyclopropylaminooxalyl-butylcarbamoyl)-octahydro-indole-1-carbonyl]-2,2-dimethyl-propyl-carbamoyl}-methyl)-amide (39a).

BOC-L-Octahydro-indole-2-carboxylic acid 21b (3.4 g, 12.6 mmol, purchased from Bachem), was suspended in 30 mL CH$_2$Cl$_2$ and cooled in a water/ice bath. N-methylmorpholine (3.0 eq., 4.2 mL, 38 mmol) was added followed by addition of solid PyBOP (1.1 eq., 7.2 g, 13.8 mmole). The ice bath was removed and the reaction stirred at RT for 1 hour under N$_2$. In a separate flask, 5.8 g of 3-amino-2-hydroxy-hexanoic acid cyclopropylamine 19b was dissolved in 30 mL of DMF and 10 mL of CH$_2$Cl$_2$ at RT. The acid (21b)/PyBOP/NMM solution was cannulated into the solution of amine 19b along with 20 mL of CH$_2$Cl$_2$ The reaction was stirred at RT for 16 hours, then quenched with aqueous sodium bicarbonate solution and concentrated in vacuo. The residue was extracted twice with EtOAc. The combined organic layers were washed with 10% citric acid solution, saturated sodium bicarbonate solution, water (5×), then brine, dried over sodium sulfate, filtered, and concentrated in vacuo. Flash chromatography on silica gel eluting with 30% EtOAc/hexanes to 100% EtOAc gave 4.35 g of 2-[1-(Cyclopropylcarbamoyl-hydroxy-methyl)-butylcarbamoyl]-octahydro-indole-1-carboxylic acid tert-butyl ester 22b. LC/MS M+H=438.2, M−H=436.3.

$^1$H-NMR (CDCl$_3$) d 0.50 (2H,m), 0.70 (2H,m), 0.91 (3H,t), 1.14 (1H,m), 1.2–1.37 (4H,m), 1.42 (9H,s), 1.59–1.71 (5H,m), 1.93 (2H,m), 2.10 (1H,bs), 2.22 (1H,m), 2.7 (1H,m), 3.8 (1H,bs), 3.98 (1H,bs) 4.02–4.2 (3H,m), 5.80 (1H,s), 7.1 (2H,bs) ppm.

BOC ester 22b (4.35 g, 7.43 mmol) was dissolved in 25 ml of CH$_2$Cl$_2$ and cooled in an ice water bath. 25 mL of TFA was added dropwise, the bath was removed and the reaction was allowed to warm to RT. TLC showed the BOC group removed after 30 minutes. After 1 hour, 25 mL of toluene was added and the reaction was concentrated to dryness and used as is in the next step.

L-CBz-tert-butyl glycine (3.16 g, 11.9 mmol) in CH$_2$Cl$_2$ (25 mL) was treated with solid PyBOP (6.7 g, 12.9 mmol) and DIEA (1.7 mL, 9.8 mmol) in 5 mL of CH$_2$Cl$_2$ The bath was removed and the reaction was allowed to warm to RT and stirred for 50 minutes. The crude free amine was dissolved in CH$_2$Cl$_2$ (25 mL), treated with DIEA (3.5 mL, 20 mmol) and then the mixture was cannulated into the Cbz-L-Tbg-OH/PyBOP solution with additional CH$_2$Cl$_2$ (40 mL) added and the mixture stirred overnight. After 21 hours, the reaction was quenched with saturated sodium bicarbonate solution and concentrated. The residue was partitioned between EtOAc and water and extracted twice with EtOAc, the combined organic layers were washed with 0.5N HCl, saturated sodium bicarbonate, water, and brine then dried over sodium sulfate, filtered, and concentrated in vacuo. Flash chromatography on silica gel eluting with 2% MeOH/EtOAc to 5% MeOH/EtOAc gave 4.2 g (72%) of (1-{2-[1-(Cyclopropylcarbamoyl-hydroxy-methyl)-butylcarbamoyl]-octahydro-indole-1-carbonyl}-2,2-dimethyl-propyl)-carbamic acid benzyl ester 23b. LC/MS M+H=585.4, M−H=583.3.

$^1$H-NMR (CDCl$_3$) d 0.55 (2H,m), 0.75 (2H,m), 0.88 (3H,t), 0.98 (9H,s), 1.22–1.41(5H,m), 1.71 (5H,m), 1.96 (2H,m), 2.21–2.44 (2H,m), 2.72(1H,m), 3.98 (1H,m), 4.07 (1H,s) 4.2–4.29 (2H,m), 4.39–4.49 (1H,m), 5.02–5.15 (2H, m), 5.4 (1H,m), 6.75(1H,m) 6.85(1H,m), 7.33 (5H,m) ppm.

Cbz ester 23b (4.2 g, 7.2 mmol) was stirred in EtOH (50 mL) and flushed with N$_2$. 800 mg of 10%Pd/C was added with EtOH (100 mL). The reaction was flushed with H$_2$ and left under an H$_2$ atmosphere overnight. After 18 hours, the reaction was filtered and concentrated, azeotroped first with CH$_3$CN then with CH$_2$Cl$_2$ and concentrated in vacuo to provide intermediate free amine (3.26 g 7.2 mmol, 100%) which was used as is in the next step.

2-(1H-benzotriazole-1-yl)-1,1,3,3-tetramethyluronium tetrafluoroborate (TBTU, 2.45 g, 7.6 mmol) was combined with DMF (20 mL) and CH$_2$Cl$_2$ (10 mL) and warmed slightly (45° C.) to dissolve all solids, then cooled in an ice water bath. A solution of L-CBz-cyclohexyl glycine (2.2 g, 7.6 mmol) in CH$_2$Cl$_2$ (30 mL) was added and the ice bath was removed. The reaction was warmed to 35° C. for 5 minutes. N-methylmorpholine (1.5 eq., 1.05 mL, 9.5 mmol) was added and the reaction stirred at RT for 30 minutes. A solution of the crude amine (2.85 g 6.32 mmol) obtained above in CH$_2$Cl$_2$ (20 mL) was cannulated into the reaction with additional CH$_2$Cl$_2$ (20 mL) and the reaction was stirred at RT overnight. After 19 hours, the reaction was quenched with saturated sodium bicarbonate solution and concentrated. The residue was partitioned between EtOAc and water and extracted twice with EtOAc. The combined organic layers were washed with 0.5N HCl, saturated sodium bicarbonate, water (4×). The water washes were back extracted with EtOAc and the combined organics were washed with brine, dried over sodium sulfate, filtered, and concentrated. Flash chromatography on silica gel eluting with 1% MeOH/CH$_2$Cl$_2$ to 4% MeOH/CH$_2$Cl$_2$ gave 2.8 g (61%) of [Cyclohexyl-(1-{2-[1-(cyclopropylcarbamoyl-hydroxy-methyl)-butylcarbamoyl]-octahydro-indole-1-carbonyl}-2,2-dimethyl-propylcarbamoyl)-methyl]-carbamic acid benzyl ester 24b. LC/MS M+H=724.2, M−H=722.3. $^1$H-NMR (CDCl$_3$) d 0.55 (2H,m), 0.74 (2H,m), 0.88 (3H,t), 1.02 (9H,s), 1.1–1.65 (22H,mm), 1.94 (2H,m), 2.12 (2H,m), 2.68–2.79(1H,m), 3.98–4.27 (4H,m), 4.46–4.6 (1H,m), 4.68 (1H,d) 4.55 (1H,d), 5.10 (2H,s), 5.40 (1H,s), 5.62 (1H,m), 6.96–7.1(2H,m), 7.3 (5H,m) ppm.

Cbz amine 24b (2.8 g, 3.9 mmol) was stirred in EtOH (60 mL) and treated with 520 mg of 10%Pd/C in EtOH (100 mL). The reaction was flushed with H$_2$ and left under H$_2$ atmosphere overnight. After 19 hours, the reaction was filtered and concentrated, azeotroped with CH$_2$Cl$_2$ and concentrated to obtain the intermediate free amine (2.33 g 3.9 mmol, 100%) which was used as is.

3-Acetyl-1H-indole-2-carboxylic acid 25b (67 mg, 0.33 mmol) in CH$_2$Cl$_2$ (2 mL) and DMF (2 mL) was treated with EDC (69 mg, 0.36 mmol) and HOAT (123 mg, 0.39 mmol) dissoleved in CH$_2$Cl$_2$(1 mL) and DIEA (160 ul, 0.9 mmol) and stirred at RT for 5 minutes. Crude amine obtained above (175 mg, 0.30 mmol) in CH$_2$Cl$_2$(5 mL) was added via cannula and the mixture stirred at RT. After 46 hours, the reaction was quenched with 0.5N HCl and concentrated. The residue was partitioned between EtOAc and water, extracted twice with EtOAc, the combined organic layers washed with 0.5N HCl, water (4×), brine then dried over sodium sulfate, filtered, and concentrated. Flash chromatography on silica gel eluting with EtOAc to 5% MeOH/EtOAc gave 166 mg (71%) of 3-acetyl-1H-indole-2-carboxylic acid [cyclohexyl-(1-{2-[1-(cyclopropylcarbamoyl-hydroxy-methyl)-butylcarbamoyl]-octahydro-indole-1-carbonyl}-2,2-dimethyl-propylcarbamoyl)-methyl]-amide 26b. FIA MS M+H=775.4, M−H=773.4, HPLC RT 8.75+8.85 (2 diastereomers). $^1$H-NMR was consistent for the desired product.

Keto alcohol 26b (166 mg, 0.21 mmol) was dissolved in dry EtOAc (6 mL), treated with EDC (605 mg, 3.15 mmol), dry DMSO (3 mL) was added and the reaction was cooled to 7° C. A solution of dichloroacetic acid (175 uL, 2.1 mmol) in dry EtOAc (1 mL) was added over 1 minute with a slight exotherm. Additional EtOAc (2 mL) was added and the ice bath was removed. After 1 hour, the reaction was cooled to 10° C., quenched with 1.0N HCl (2 mL), then extracted twice with EtOAc. The combined organics were washed with water (4×) and brine, then dried over sodium sulfate, filtered, and concentrated. Flash chromatography on silica gel eluting with 25% EtOAc/CH$_2$Cl$_2$ to 100% EtOAc followed by dissolving in CH$_3$CN/water and lyophilizing gave 139 mg (86%) of 3-acetyl-1H-indole-2-carboxylic acid (cyclohexyl-{1-[2-(1-cyclopropylaminooxalyl-butylcarbamoyl)-octahydro-indole-1-carbonyl]-2,2-dimethyl-propylcarbamoyl}-methyl)-amide 39a. LC/MS M+H=773.41, M−H=771.49, LC/MS RT=5.01 min, HPLC RT=9.53 min.

$^1$H-NMR (CDCl$_3$) d 0.50 (2H,m), 0.72 (5H,m), 0.92 (9H,s), 1.0–1.32 (10H,m), 1.47–1.75 (10H,m), 1.79–1.93 (3H,m), 2.03 (1H,m), 2.16 (1H,m), 2.32 (1H,dd), 2.68 (1H,m), 2.83 (3H, s), 4.4 (1H,m) 4.6 (1H,t), 4.8 (1H,d), 5.05 (1H,m), 5.3 (1H,m), 6.77 (1H,d), 7.02 (1H,m), 7.27 (2H,m), 7.61 (1H, d), 7.9 (1H,d) 8.86 (1H,bs) ppm.

Example 5

5-Acetyl-1H-indole-2-carboxylic acid (cyclohexyl-{1-[2-(1-cyclopropylaminooxalyl-butylcarbamoyl)-octahydro-indole-1-carbonyl]-2,2-dimethyl-propylcarbamoyl}-methyl)-amide (40a).

5-Acetyl-1H-indole-2-carboxylic acid 27b (67 mg, 0.33 mmol) stirred in CH$_2$Cl$_2$(2 mL) and DMF (2 mL) was treated with EDC (69 mg, 0.36 mmol) and HOAT (123 mg, 0.39 mmol) dissolved in CH$_2$Cl$_2$(1 mL) and DIEA (160 ul, 0.9 mmol) and the mixture stirred at RT for 5 minutes. Added crude intermediate amine (175 mg, 0.30 mmol, identically prepared above in example 4) in CH$_2$Cl$_2$(5 mL) via cannula and stirred at RT. After 45 hours, the reaction was quenched with 0.5N HCl solution and concentrated. The residue was partitioned between EtOAc and water, extracted twice with EtOAc, the combined organic layers washed with 0.5N HCl, water (4×), and brine, then dried over sodium sulfate, filtered, and concentrated in vacuo. Flash chromatography on silica gel eluting with neat EtOAc to 5% MeOH/EtOAc gave 142 mg (61%) of 5-acetyl-1H-indole-2-carboxylic acid [cyclohexyl-(1-{2-[1-(cyclopropylcarbamoyl-hydroxy-methyl)-butylcarbamoyl]-octahydro-indole-1-carbonyl}-2,2-dimethyl-propylcarbamoyl)-methyl]-amide 28b. LC/MS M+H=775.44, M−H=773.52, LC/MS RT=3.78 min., HPLC RT=7.70 min. $^1$H-NMR was consistent for the desired product.

Keto-alcohol 28b (142 mg, 0.18 mmol) was dissolved in dry EtOAC (10 mL) treated with EDC (520 mg, 2.7 mmol) and dry DMSO (5 mL) and then cooled to 7° C. A solution of dichloroacetic acid (150 uL, 1.8 mmol) in dry EtOAc (1 mL) was added over 1 minute giving a slight exotherm. EtOAc (1 mL) was added and the ice bath was removed. After 1 hour, the reaction was cooled to 10° C., quenched with 1.0N HCl (2 mL) and extracted twice with EtOAc. The combined organics were washed with water (4×) and brine, then dried over sodium sulfate, filtered and concentrated in vacuo. Flash chromatography on silica gel eluting with 10% EtOAc/CH$_2$Cl$_2$ to 75% EtOAc/CH$_2$Cl$_2$ followed by dissolving in CH$_3$CN/water and lyophilizing afforded 129 mg (93%) of 5-acetyl-1H-indole-2-carboxylic acid (cyclohexyl-{1-[2-(1-cyclopropylaminooxalyl-butylcarbamoyl)-octahydro-indole-1-carbonyl]-2,2-dimethyl-propylcarbamoyl}-methyl)-amide 40a. LC/MS M+H=773.44, M−H=771.48, LC/MS RT=4.99 min, HPLC RT=9.30 min.

$^1$H-NMR (CDCl$_3$) d 0.56 (2H,m), 0.8 (5H,m), 0.98 (9H, s), 1.0–2.2 (25H,m), 2.45(1H,m), 2.68(3H,s), 2.86(1H,m), 4.27 (1H, m) 4.72 (1H,t), 4.8 (1H,d), 5.18 (1H,m), 5.42 (1H,m), 6.92 (1H,d), 7.09 (2H,m), 7.21 (1H,m), 7.6 (1H,d), 7.91 (1H,d), 8.36 (1H,s), 9.1 (1H,bs), 11.32 (1H,bs) ppm.

Example 6

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml wit. 10,000 cells in 100 ul were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according to the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

Example 7

HCV Ki Assay Protocol

HPLC Microbore Method for Separation of 5AB Substrate and Products

Substrate:
NH$_2$-Glu-Asp-Val-Val-(alpha)Abu-Cys-Ser-Met-Ser-Tyr-COOH

A stock solution of 20 mM 5AB (or concentration of your choice) was made in DMSO w/ 0.2M DTT. This was stored in aliquots at −20 C.

Buffer: 50 mM HEPES, pH 7.8; 20% glycerol; 100 mM NaCl

Total assay volume was 100 µL

|  | X1 (µL) | conc. in assay |
|---|---|---|
| Buffer | 86.5 | see above |
| 5 mM KK4A | 0.5 | 25 µM |
| 1 M DTT | 0.5 | 5 mM |
| DMSO or inhibitor | 2.5 | 2.5% v/v |

-continued

|  | X1 (µL) | conc. in assay |
|---|---|---|
| 50 µM tNS3 | 0.05 | 25 nM |
| 250 µM 5AB (initiate) | 20 | 25 µM |

The buffer, KK4A, DTT, and tNS3 were combined; distributed 78 µL each into wells of 96 well plate. This was incubated at 30 C for ~5–10 min.

2.5 µL of appropriate concentration of test compound was dissolved in DMSO (DMSO only for control) and added to each well. This was incubated at room temperature for 15 min.

Initiated reaction by addition of 20 µL of 250 µM 5AB substrate (25 µM concentration is equivalent or slightly lower than the Km for 5AB).

Incubated for 20 min at 30 C.

Terminated reaction by addition of 25 µL of 10% TFA

Transferred 120 µL aliquots to HPLC vials

Separated SMSY product from substrate and KK4A by the following method:

Microbore Separation Method:

Instrumentation: Agilent 1100

Degasser G1322A

Binary pump G1312A

Autosampler G1313A

Column thermostated chamber G1316A

Diode array detector G1315A

Column:
Phenomenex Jupiter; 5 micron C18; 300 angstroms; 150×2 mm; P/O 00F-4053-B0

Column thermostat: 40 C

Injection volume: 100 µL

Solvent A=HPLC grade water+0.1% TFA

Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min

Post-run time: 10 min.

Table 5 below depicts Mass Spec., HPLC, Ki and IC$_{50}$ data for certain compounds of the invention.

Compounds with Ki's ranging from 1 µM to 5 µM are designated A. Compounds with Ki's ranging from 1 µM to 0.5 µM are designated B. Compounds with Ki's below 0.5 µM are designated C. Compounds with IC50's ranging from 1 µM to 5 µM are designated A. Compounds with IC50's ranging from 1 µM to 0.5 µM are designated B. Compounds with IC50's below 0.5 µM are designated C.

| Compound | MS+ | HPLC, R$_t$ (min) | Ki | IC$_{50}$ |
|---|---|---|---|---|
| 1a | 749 | 9.50 | C | ND |
| 2a | 640 | 3.51 | B | ND |
| 3a | 681 | 3.49 | C | A |
| 4a | 694 | 3.71 | C | B |
| 5a | 731 | 3.81 | C | ND |
| 6a | 745 | 4.02 | C | ND |
| 7a | 758 | 4.69 | C | ND |
| 8a | 782 | 4.23 | C | ND |
| 9a | 855 | 4.29 | C | C |
| 10a | 694 | 3.69 | C | B |
| 11a | 681 | 3.98 | C | C |
| 12a | 726 | 4.09 | C | C |
| 13a | 727 | 3.97 | C | B |
| 14a | 727 | 3.97 | C | A |
| 15a | 682 | 3.45 | C | C |
| 16a | 738 | 3.88 | C | A |
| 17a | 696 | 3.31 | A | ND |
| 18a | 749 | 4.16 | C | C |
| 19a | 736 | 4.84 | C | B |
| 20a | 736 | 4.80 | C | B |
| 21a | 735 | 4.60 | C | C |
| 22a | 700 | 3.77 | B | A |
| 23a | 688 | 3.97 | C | A |
| 24a | 686 | 4.55 | C | A |
| 25a | 751 | 4.61 | C | C |
| 26a | 682 | 3.96 | C | A |
| 27a | 682 | 4.01 | C | A |
| 28a | 737 | 3.35 | C | ND |
| 29a | 751 | 3.94 | C | B |
| 30a | 693 | 4.35 | B | A |
| 31a | 693 | 3.56 | C | A |
| 32a | 694 | 3.48 | C | A |
| 33a | 751 | 4.76 | C | C |
| 34a | 825 | 9.69 | C | A |
| 35a | 744 | 4.35 | C | A |
| 36a | 744 | 5.04 | C | A |
| 37a | 737 | 4.18 | C | C |
| 38a | 717 | 4.03 | B | ND |
| 39a | 773 | 5.02 | C | C |
| 40a | 773 | 4.37 | C | C |
| 41a | 751 | 4.70 | A | C |
| 42a | 751 | 4.30 | C | C |
| 43a | 750 | 4.59 | C | C |
| 44a | 737 | 4.25 | C | C |
| 45a | 805 | 8.41 | C | C |
| 46a | 733 | 4.41 | C | A |
| 47a | 725 | 3.58 | B | A |
| 48a | 738 | 3.99 | C | A |
| 49a | 738 | 3.99 | A | ND |
| 50a | 682 | 3.78 | A | ND |
| 51a | 694 | 4.05 | C | B |
| 52a | 762 | 4.05 | C | C |
| 53a | 814 | 4.70 | C | C |
| 54a | 739 | 3.57 | A | ND |
| 55a | 612 | 4.06 | A | ND |
| 56a | 761 | 4.99 | C | ND |
| 57a | 718 | 4.83 | C | ND |
| 58a | 711 | 4.50 | C | ND |
| 59a | 725 | 4.90 | C | ND |
| 60a | 694 | 4.10 | A | A |
| 61a | 773 | 4.20 | C | C |
| 62a | 738 | 5.29 | B | ND |
| 63 | 780 | 5.40 | C | B |
| 64 | 739 | 4.82 | C | C |
| 65 | 723 | 4.56 | C | C |
| 66 | 842 | 4.15 | C | C |
| 67 | 825 | 4.77 | C | C |
| 68 | 737 | 9.75 | C | C |

What is claimed is:

1. A compound of formula (IA):

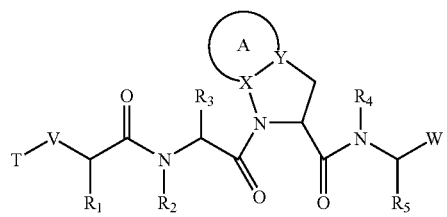

wherein:

A, together with X and Y, is:
a 3- to 6-membered aromatic or non-aromatic ring having up to 3 heteroatoms independently selected from N, NH, O, SO$_1$ or SO$_2$;
wherein said ring is optionally fused to a (C6–C10)aryl, (C5–C10)heteroaryl, (C3–C10)cycloalkyl, or (C3–C10)heterocyclyl;
wherein A has up to 3 substituents selected independently from J;
J is halogen, —OR', —NO$_2$, —CF$_3$, —OCF$_3$, —R', oxo, —OR', —O-benzyl, —O-phenyl, 1,2-methylenedioxy, —N(R')$_2$, —SR', —SOR', —SO$_2$R', —C(O)R', —COOR' or —CON(R')$_2$, wherein R' is independently selected from:
hydrogen,
(C1–C12)-aliphatic,
(C3–C10)-cycloalkyl or -cycloalkenyl,
[(C3–C10)-cycloalkyl or -cycloalkenyl]-(C1–C12)-aliphatic,
(C6–C10)-aryl,
(C6–C10)-aryl-(C1–C12)aliphatic,
(C3–C10)-heterocyclyl,
(C6–C10)-heterocyclyl-(C1–C12)aliphatic,
(C5–C10)-heteroaryl, or
(C5–C10)-heteroaryl-(C1–C12)-aliphatic;
R$_1$ and R$_3$ are independently:
(C1–C12)-aliphatic,
(C3–C10)-cycloalkyl or -cycloalkenyl,
[(C3–C10)-cycloalkyl or -cycloalkenyl]-(C1–C12)-aliphatic,
(C6–C10)-aryl,
(C6–C10)-aryl-(C1–C12)aliphatic,
(C3–C10)-heterocyclyl,
(C6–C10)-heterocyclyl-(C1–C12)aliphatic,
(C5–C10)-heteroaryl, or
(C5–C10)-heteroaryl-(C1–C12)-aliphatic,
wherein each of R$_1$ and R$_3$ is independently and optionally substituted with up to 3 substituents independently selected from J;
wherein up to 3 aliphatic carbon atoms in R$_1$ and R$_3$ may be replaced by a heteroatom selected from O, NH, S, SO, or SO$_2$ in a chemically stable arrangement;
R$_2$ and R$_4$ are independently
hydrogen,
(C1–C12)-aliphatic,
(C3–C10)-cycloalkyl-(C1–C12)-aliphatic, or
(C6–C10)aryl-(C1–C12)-aliphatic,
wherein each of R$_2$ and R$_4$ is independently and optionally substituted with up to 3 substituents independently selected from J;

wherein up to two aliphatic carbon atoms in $R_2$ and $R_4$ may be replaced by a heteroatom selected from O, NH, S, SO, or $SO_2$;

$R_5$ is (C1–C12)-aliphatic, wherein any hydrogen is optionally replaced with halogen, and wherein any hydrogen or halogen atom bound to any terminal carbon atom of $R_5$ is optionally substituted with sulfhydryl or hydroxy;

W is selected from:

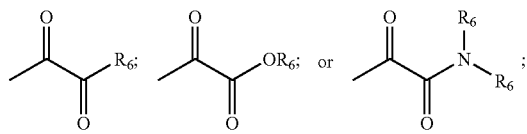

wherein each $R_6$ is independently:
hydrogen,
(C1–C12)-aliphatic,
(C6–C10)-aryl,
(C6–C10)-aryl-(C1–C12)aliphatic,
(C3–C10)-cycloalkyl or -cycloalkenyl,
[(C3-C10)-cycloalkyl or -cycloalkenyl]-(C1–C12)-aliphatic,
(C3–C10)-heterocyclyl,
(C3–C10)-heterocyclyl-(C1–C12)-aliphatic,
(C5–C10)heteroaryl, or
(C5–C10)heteroaryl-(C1–C12)-aliphatic, or
two $R_6$ groups, which are bound to the same nitrogen atom, form together with that nitrogen atom, a (C3–C10)-heterocyclic ring;
wherein $R_6$ is optionally substituted with up to 3 J substituents;

V is $-C(O)N(R_8)-$, $-S(O)N(R_8)-$, or $-S(O)_2N(R_8)-$;
wherein $R_8$ is hydrogen or (C1–C12)-aliphatic;

T is selected from:
(C5)-heterocyclyl,
(C5)-heterocyclyl-(C1–C12)-aliphatic,
(C5)heteroaryl, or
(C5)heteroaryl-(C1–C12)-aliphatic;
wherein each T is optionally substituted with up to 3 J substituents.

2. A compound of formula (IB):

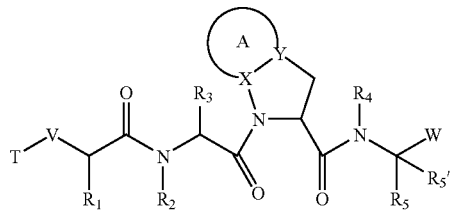

(IB)

wherein:
A, together with X and Y, is:
a 3- to 6-membered aromatic or non-aromatic ring having up to 3 heteroatoms independently selected from N, NH, O, S, SO, or $SO_2$;
wherein said ring is optionally fused to a (C6–C10)aryl, (C5–C10)heteroaryl, (C3–C10)cycloalkyl, or (C3–C10)heterocyclyl;

wherein A has up to 3 substituents selected independently from J and wherein the 5-membered ring to which A is fused has up to 4 substituents selected independently from J; and wherein X and Y are independently C(H) or N;

J is halogen, $-OR'$, $-OC(O)N(R')_2$, $-NO_2$, $-CN$, $-CF_3$, $-OCF_3$, $-R'$, oxo, thioxo, 1,2-methylenedioxy, 1,2-ethylenedioxy, $-N(R')_2$, $-SR'$, $-SOR'$, $-SO_2R'$, $-SO_2N(R')_2$, $-SO_3R'$, $-C(O)R'$, $-C(O)C(O)R'$, $-C(O)CH_2C(O)R'$, $-C(S)R'$, $-C(O)OR'$, $-OC(O)R'$, $-C(O)N(R')_2$, $-OC(O)N(R')_2$, $-C(S)N(R')_2$, $-(CH_2)_{0-2}NHC(O)R'$, $-N(R')N(R')COR'$, $-N(R')N(R')C(O)OR'$, $-N(R')N(R')CON(R')_2$, $-N(R')SO_2R'$, $-N(R')SO_2N(R')_2$, $-N(R')C(O)OR'$, $-N(R')C(O)R'$, $-N(R')C(S)R'$, $-N(R')C(O)N(R')_2$, $-N(R')C(S)N(R')_2$, $-N(COR')COR'$, $-N(OR')R'$, $-CN$, $-C(=NH)N(R')_2$, $-C(O)N(OR')R'$, $-C(=NOR')R'$, $-OP(O)(OR')_2$, $-P(O)(R')_2$, $-P(O)(OR')_2$, or $-P(O)(H)(OR')$;

wherein:
two R' groups together with the atoms to which they are bound form a 3- to 10-membered aromatic or non-aromatic ring having up to 3 heteroatoms independently selected from N, NH, O, S, SO, or $SO_2$, wherein the ring is optionally fused to a (C6–C10)aryl, (C5–C10)heteroaryl, (C3–C10)cycloalkyl, or a (C3–C10)heterocyclyl, and wherein any ring has up to 3 substituents selected independently from $J_2$; or
each R' is independently selected from:
hydrogen-,
(C1–C12)-aliphatic-,
(C3–C10)-cycloalkyl or -cycloalkenyl-,
[(C3–C10)-cycloalkyl or -cycloalkenyl]-(C1–C12)-aliphatic-,
(C6–C10)-aryl-,
(C6–C10)-aryl-(C1–C12)aliphatic-,
(C3–C10)-heterocyclyl-,
(C6–C10)-heterocyclyl-(C1–C12)aliphatic-,
(C5–C10)-heteroaryl-, or
(C5–C10)-heteroaryl-(C1–C12)-aliphatic-, wherein R' has up to 3 substituents selected independently from $J_2$;

$J_2$ is halogen, $-OR'$, $-OC(O)N(R')_2$, $-NO_2$, $-CN$, $-CF_3$, $-OCF_3$, $-R'$, oxo, thioxo, 1,2-methylenedioxy, $-N(R')_2$, $-SR'$, $-SOR'$, $-SO_2R'$, $-SO_2N(R')_2$, $-SO_3R'$, $-C(O)R'$, $-C(O)C(O)R'$, $-C(O)CH_2C(O)R'$, $-C(S)R'$, $-C(O)OR'$, $-OC(O)R'$, $-C(O)N(R')_2$, $-OC(O)N(R')_2$, $-C(S)N(R')_2$, $-(CH_2)_{0-2}NHC(O)R'$, $-N(R')N(R')COR'$, $-N(R')N(R')C(O)OR'$, $-N(R')N(R')CON(R')_2$, $-N(R')SO_2R'$, $-N(R')SO_2N(R')_2$, $-N(R')C(O)OR'$, $-N(R')C(O)R'$, $-N(R')C(S)R'$, $-N(R')C(O)N(R')_2$, $-N(R')C(S)N(R')_2$, $-N(COR')COR'$, $-N(OR')R'$, $-CN$, $-C(=NH)N(R')_2$, $-C(O)N(OR')R'$, $-C(=NOR')R'$, $-OP(O)(OR')_2$, $-P(O)(R')_2$, $-P(O)(OR')_2$, or $-P(O)(H)(OR')$;

$R_1$ and $R_3$ are independently:
(C1–C12)-aliphatic-,
(C3–C10)-cycloalkyl- or -cycloalkenyl-,
[(C3–C10)-cycloalkyl- or -cycloalkenyl]-(C1–C12)-aliphatic-,
(C6–C10)-aryl-,
(C6–C10)-aryl-(C1–C12)aliphatic-,
(C3–C10)-heterocyclyl-,
(C6–C10)-heterocyclyl-(C1–C12)aliphatic-,
(C5–C10)-heteroaryl-, or
(C5–C10)-heteroaryl-(C1–C12)-aliphatic-, wherein each of $R_1$ and $R_3$ is independently and optionally substituted with up to 3 substituents independently selected from J;

wherein up to 3 aliphatic carbon atoms in $R_1$ and $R_3$ may be replaced by a heteroatom selected from O, N, NH, S, SO, or $SO_2$ in a chemically stable arrangement;

$R_2$ and $R_4$ are independently:
hydrogen-,
(C1–C12)-aliphatic-,
(C3–C10)-cycloalkyl-(C1–C12)-aliphatic-, or
(C6–C10)aryl-(C1–C12)-aliphatic-,
wherein each of $R_2$ and $R_4$ is independently and optionally substituted with up to 3 substituents independently selected from J;

wherein up to two aliphatic carbon atoms in $R_2$ and $R_4$ may be replaced by a heteroatom selected from O, N, NH, S, SO or $SO_2$;

$R_5$ is (C1–C12)-aliphatic, wherein any hydrogen is optionally replaced with halogen, and wherein any terminal carbon atom of $R_5$ is optionally substituted with sulfhydryl or hydroxy;

$R_5$ is hydrogen or (C1–C12)-aliphatic, wherein any hydrogen is optionally replaced with halogen, and wherein any hydrogen or halogen atom bound to any terminal carbon atom of $R_{5'}$ is optionally substituted with sulfhydryl or hydroxy;

W is:

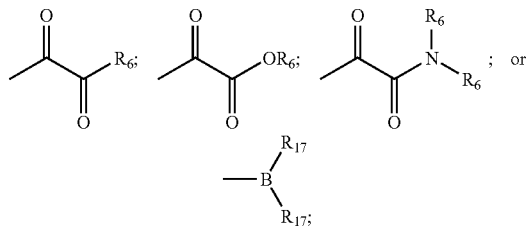

wherein each $R_6$ is independently:
hydrogen-,
(C1–C12)-aliphatic-,
(C6–C10)-aryl-,
(C6–C10)-aryl-(C1–C12)aliphatic-,
(C3–C10)-cycloalkyl- or cycloalkenyl-,
[(C3–C10)-cycloalkyl- or cycloalkenyl]-(C1–C12)-aliphatic-,
(C3–C10)-heterocyclyl-,
(C3–C10)-heterocyclyl-(C1–C12)-aliphatic-,
(C5–C10)heteroaryl-, or
(C5–C10)heteroaryl-(C1–C12)-aliphatic-, or
two $R_6$ groups, which are bound to the same nitrogen atom, form together with that nitrogen atom, a (C3–C10)-heterocyclic ring;
wherein $R_6$ is optionally substituted with up to 3 J substituents;

each $R_{17}$ is independently —OR'; or the $R_{17}$ groups together with the boron atom, is a (C3–C10)-membered heterocyclic ring having in addition to the boron up to 3 additional heteroatoms selected from N, NH, O, S, SO, and $SO_2$;

V is —C(O)N($R_8$)—, —S(O)N($R_8$)—, —S(O)$_2$N($R_8$)—, —OS(O)—, —OS(O)$_2$—, —OC(O)—, or —O—;
wherein $R_8$ is hydrogen or (C1–C12)-aliphatic;
T is:
(C5)-heterocyclyl-,
(C5)-heterocyclyl-(C1–C12)-aliphatic-,
(C5)-heteroaryl-, or
(C5)-heteroaryl-(C1–C12)-aliphatic-,
wherein each T is optionally substituted with up to 3 J substituents.

3. The compound according to claim 1 or claim 2, wherein A, together with X, Y and the ring containing the nitrogen atom, is:

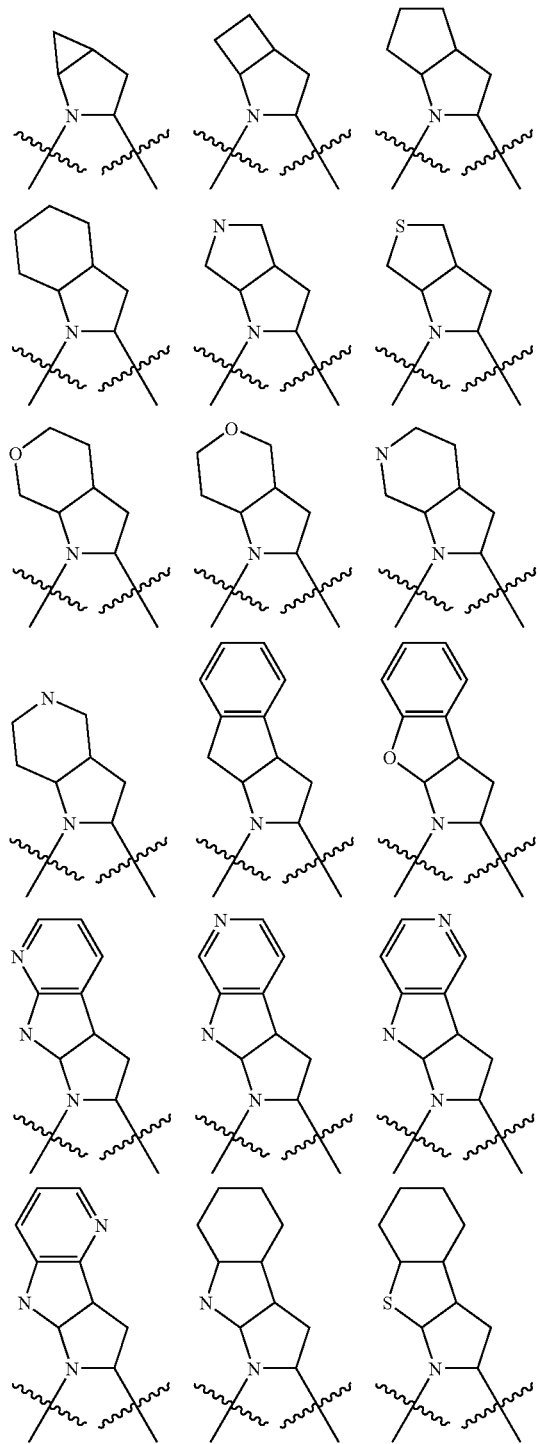

-continued
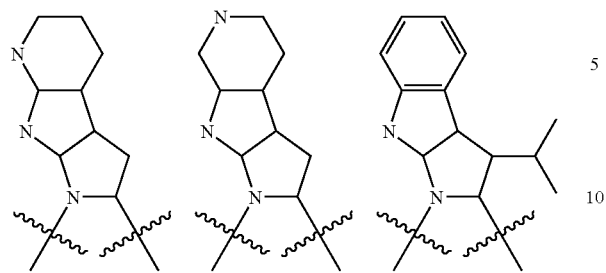
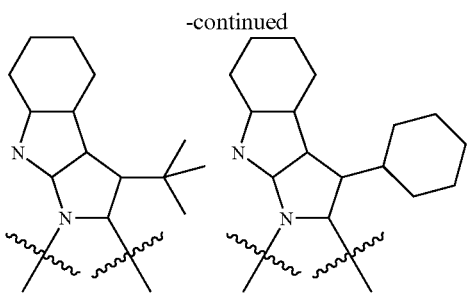
-continued
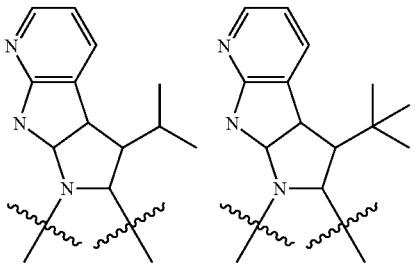
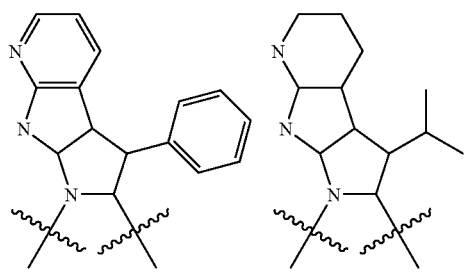
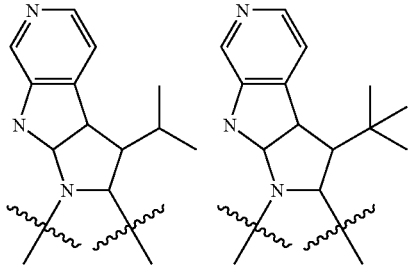
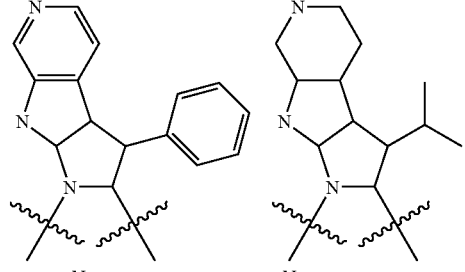
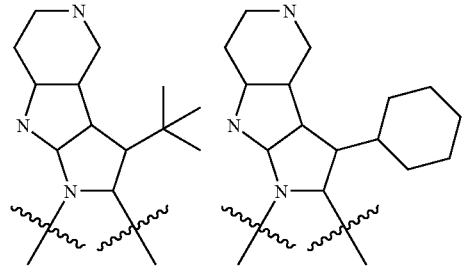

-continued
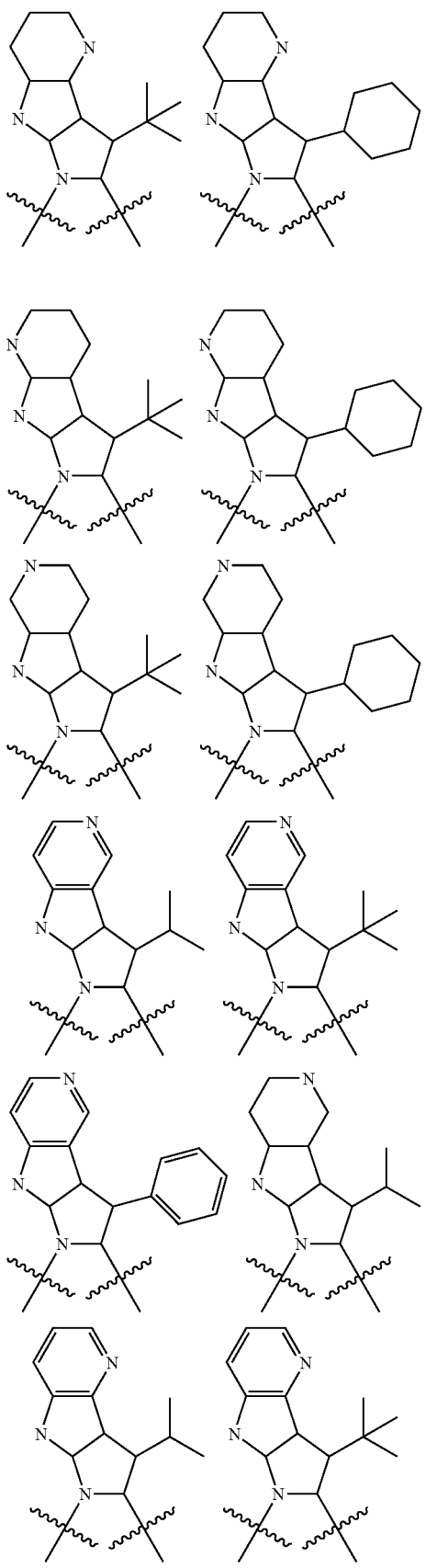
-continued
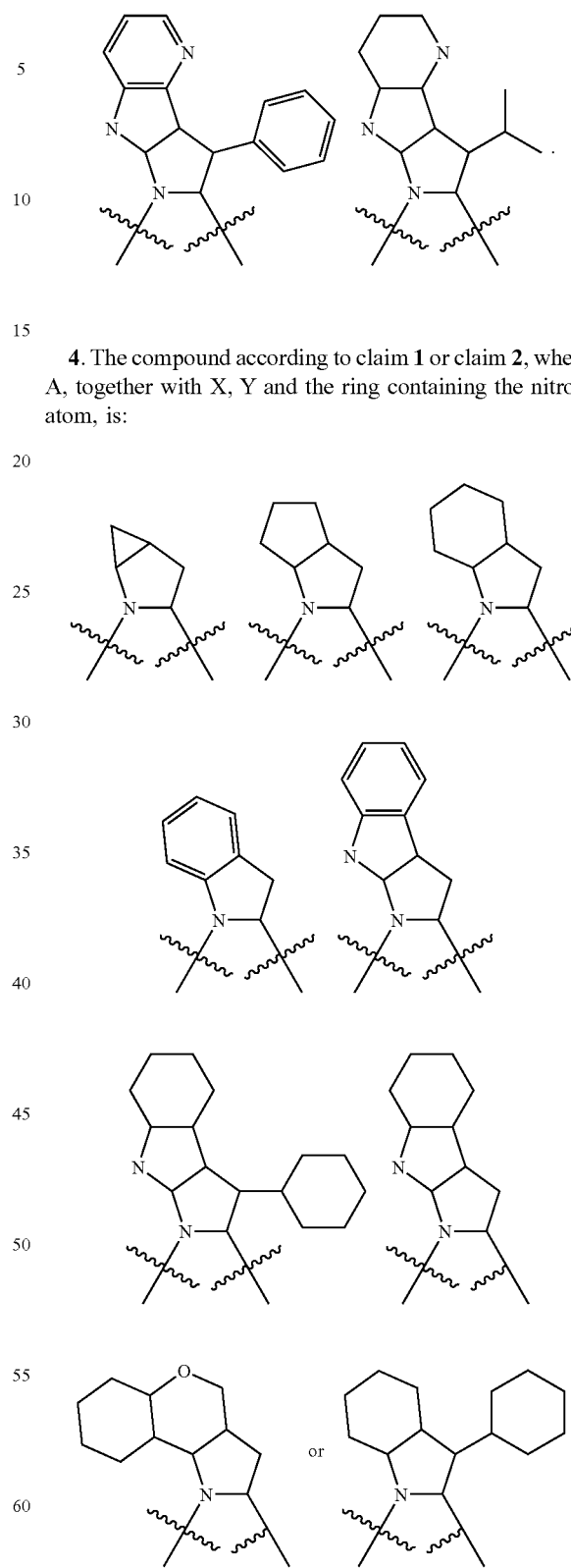
4. The compound according to claim 1 or claim 2, wherein A, together with X, Y and the ring containing the nitrogen atom, is:
5. The compound according to claim 4, wherein A, together with X, Y and the ring containing the nitrogen atom, is:

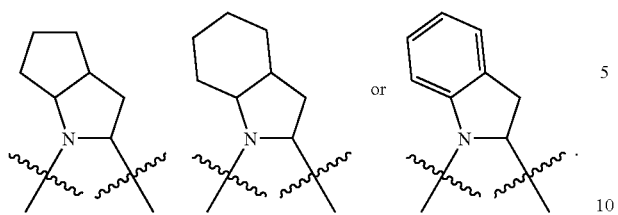

6. The compound according to claim 5, wherein A, together with X, Y and the ring containing the nitrogen atom, is:

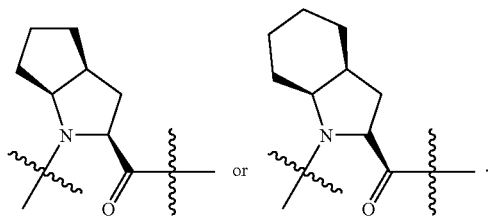

7. The compound according to claim 1, wherein T contains at least one hydrogen bond donor moiety selected from —NH$_2$, —NH—, —OH, and —SH.

8. The compound according to claim 7, wherein T is:

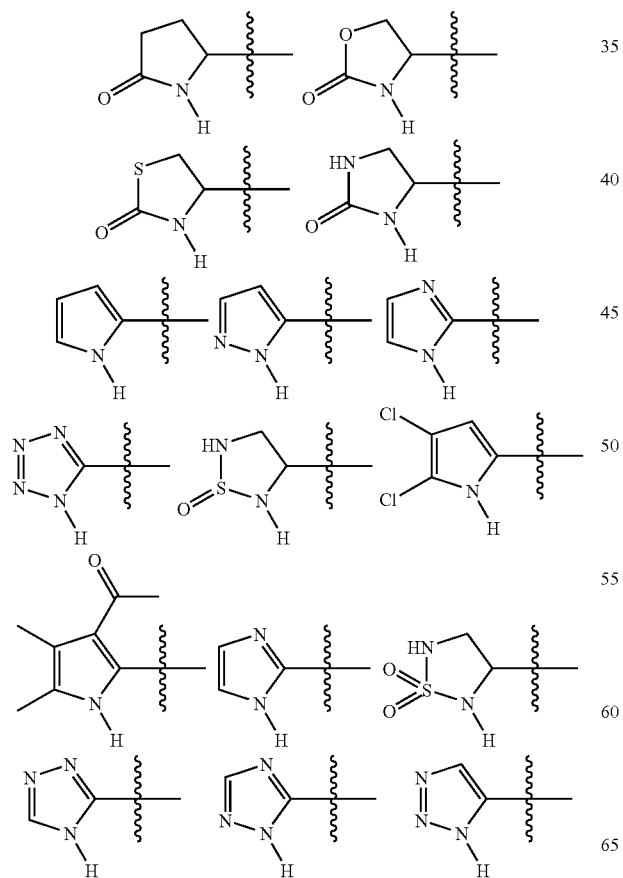

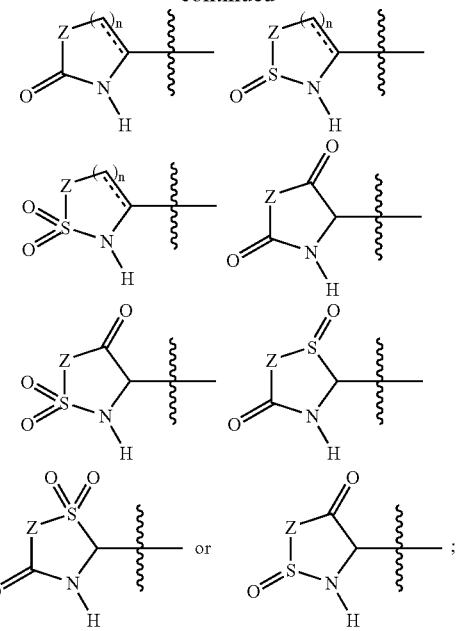

wherein:
T is optionally substituted with up to 3 J substituents, wherein J is as defined in claim 1;
Z is independently O, S, NR$_{10}$, C(R$_{10}$)$_2$;
R$_{10}$ is:
  hydrogen,
  (C1–C12)-aliphatic-,
  (C6–C10)-aryl-,
  (C6–C10)-aryl-(C1–C12)aliphatic-,
  (C3–C10)-cycloalkyl or -cycloalkenyl-,
  [(C3–C10)-cycloalkyl or -cycloalkenyl]-(C1–C12)aliphatic-,
  (C3–C10)-heterocyclyl-,
  (C3–C10)-heterocyclyl-(C1–C12)-aliphatic-,
  (C5–C10)-heteroaryl-, or
  (C5–C10)-heteroaryl-(C1–C12)-aliphatic-;
n is 1; and
⁻⁻⁻⁻⁻ is independently a single bond or a double bond.

9. The compound according to claim 8, wherein T is:

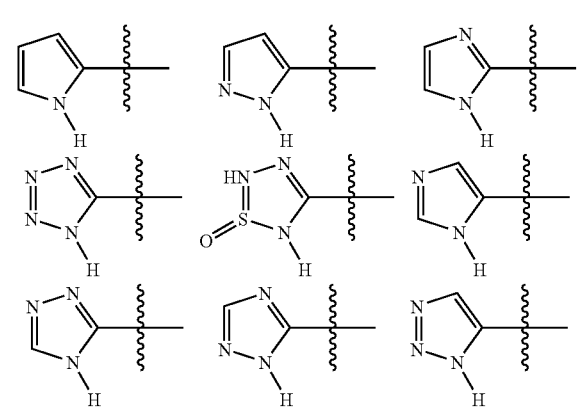

-continued
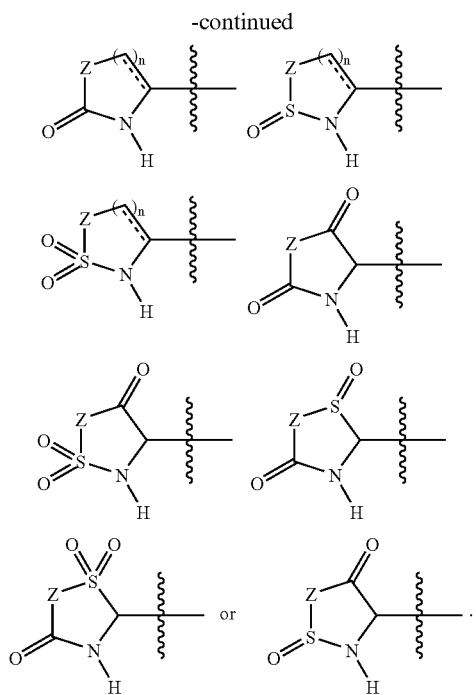
10. The compound according to claim 9, wherein T is:
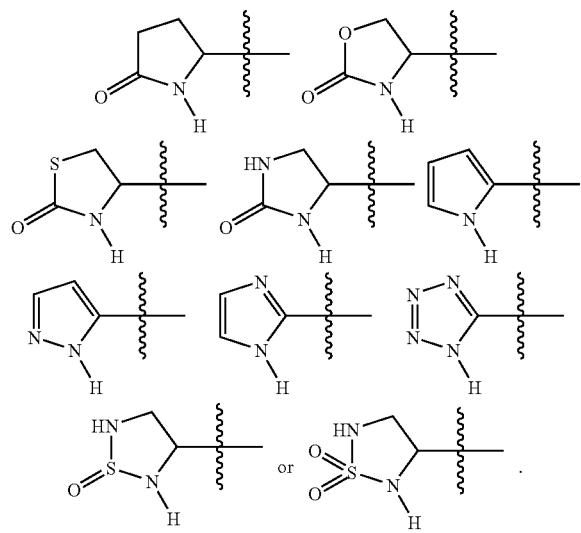
11. The compound according to claim 10, wherein T is:
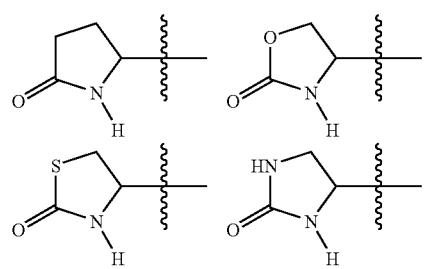
-continued
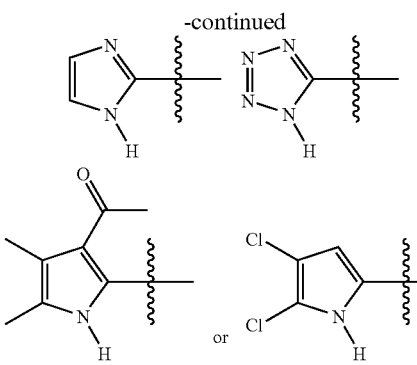
12. The compound according to claim 11, wherein T is:
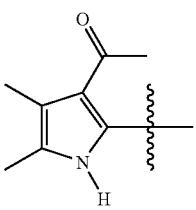
13. The compound according to any one of claims 1–2 or 5–12, wherein $R_1$ is:
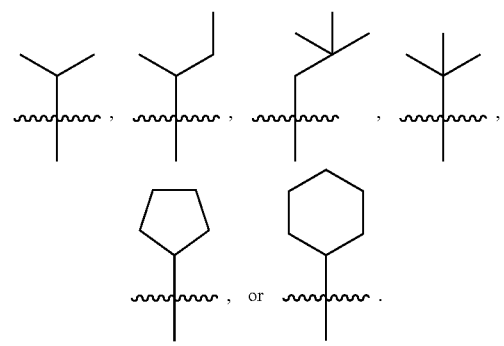
14. The compound according to any one of claims 1–2 or 5–12, wherein $R_3$:
15. The compound according to any one of claims 1–2 or 5–12, wherein $R_5$ is:

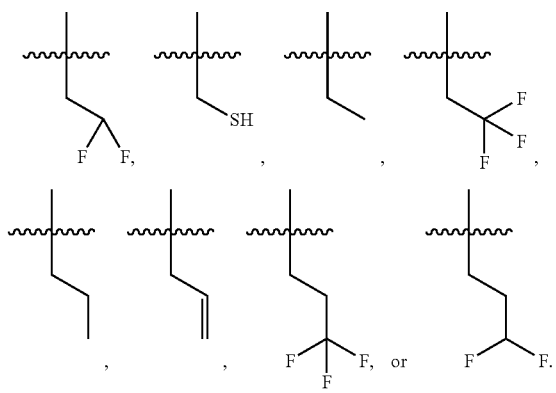

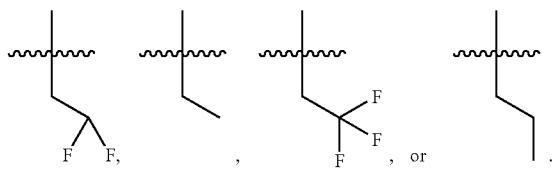

16. The compound according to claim 15, wherein $R_5$:

17. The compound according to any one of claims 1–2, or 5–12, wherein $R_2$ and $R_4$ are each independently H, methyl, ethyl or propyl.

18. The compound according to any one of claims 1–2, or 5–12, wherein V is —C(O)N($R_8$)— and $R_8$ is hydrogen.

19. The compound according to any one of claims 1–2, or 5–12, wherein W is:

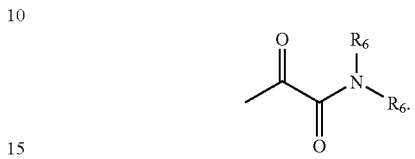

20. The compound according to claim 19, wherein one $R_6$ is hydrogen and the other $R_6$ is:
- (C6–C10)-aryl-(C1–C3)alkyl-, wherein the alkyl is optionally substituted with $CO_2H$,
- (C3–C6)cycloalkyl-,
- (C5)-heterocylyl-(C1–C3)alkyl-,
- (C3–C6)alkenyl-; or
- each $R_6$ is (C1–C6)-alkyl-.

21. The compound according to claim 1, wherein said compound is selected from:

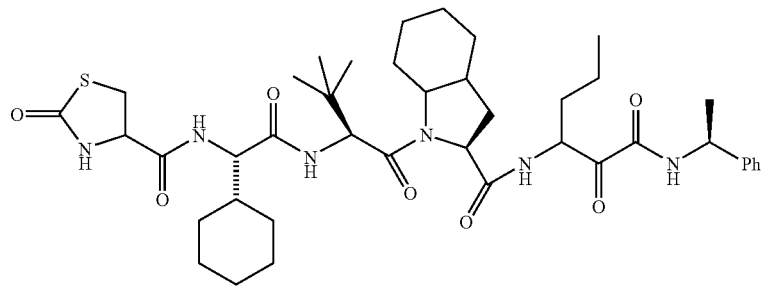

8

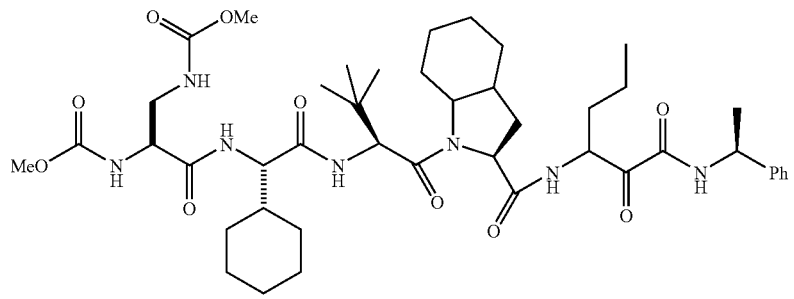

9

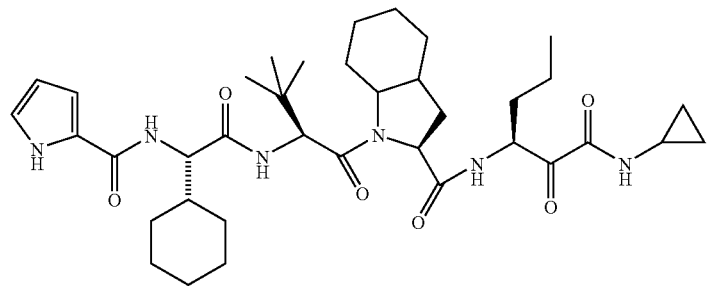
11
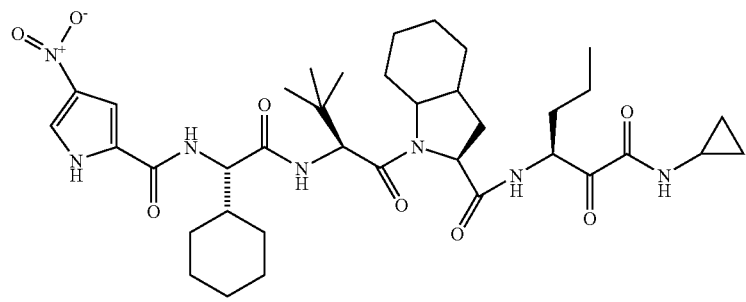
12
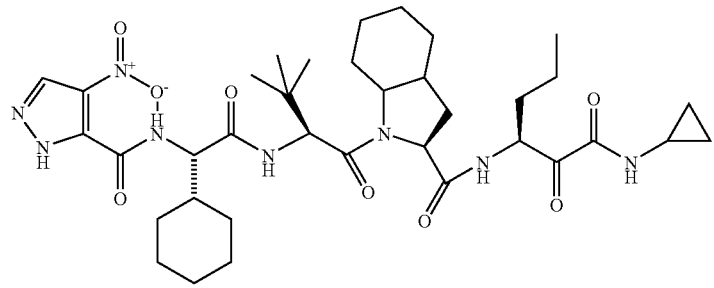
13
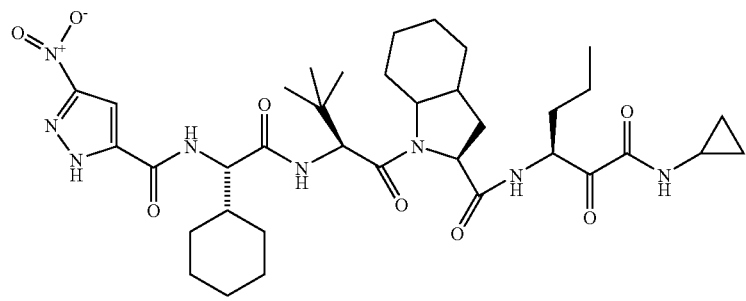
14
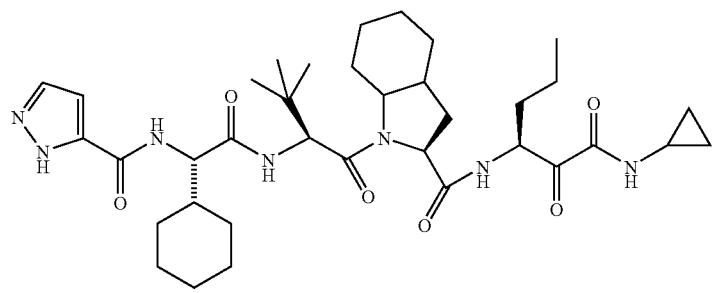
15

-continued
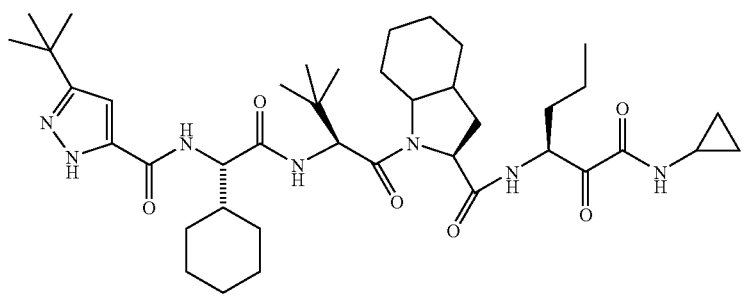
16
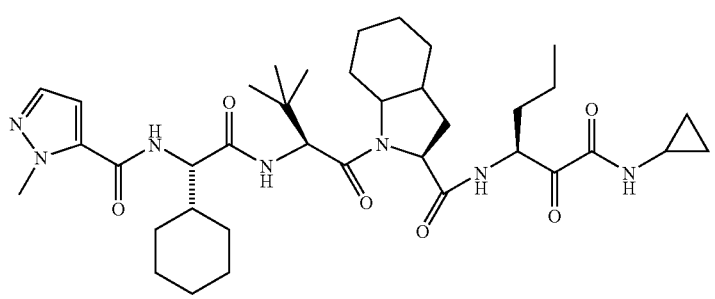
17
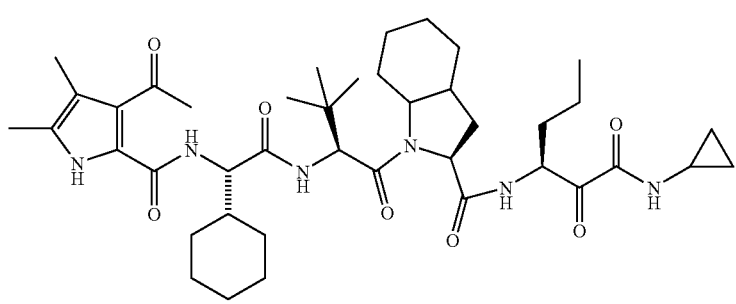
25
or
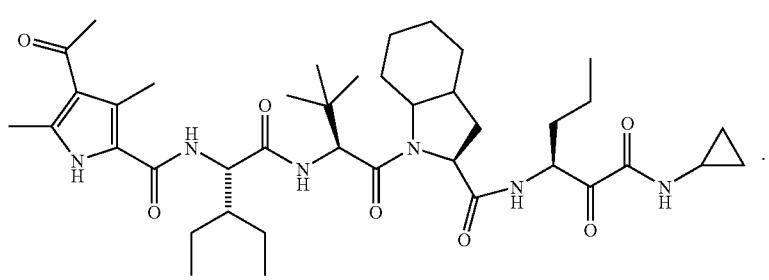
29
.
22. The compound according to claim 1, wherein the compound is selected from:
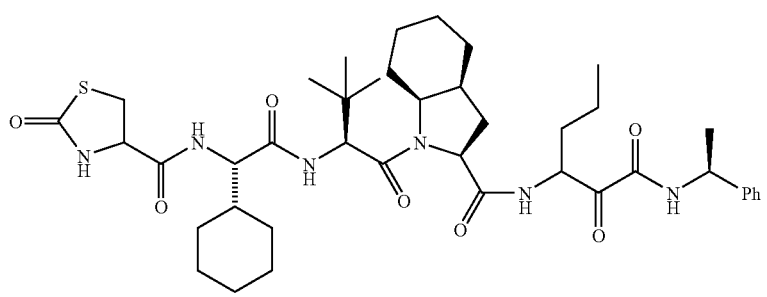
8a -continued
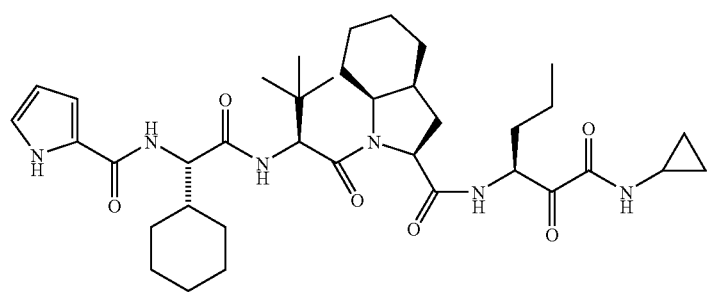
11a
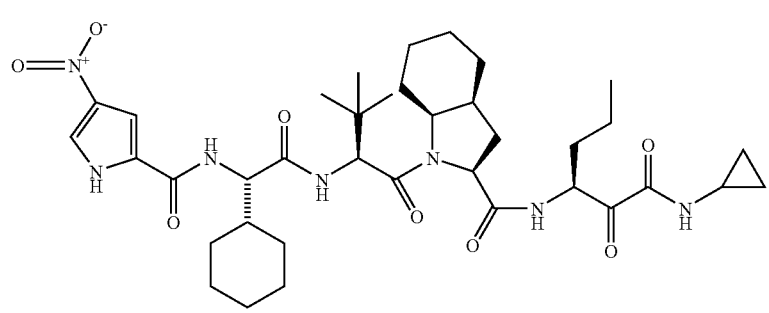
12a
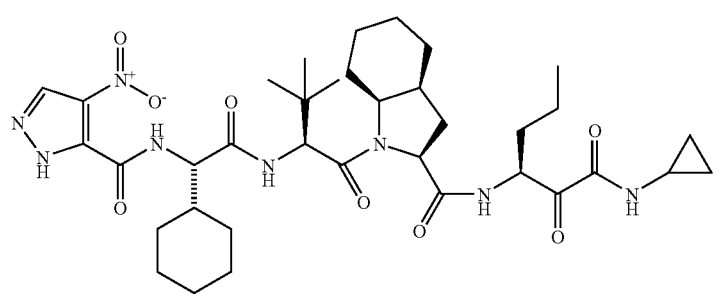
13a
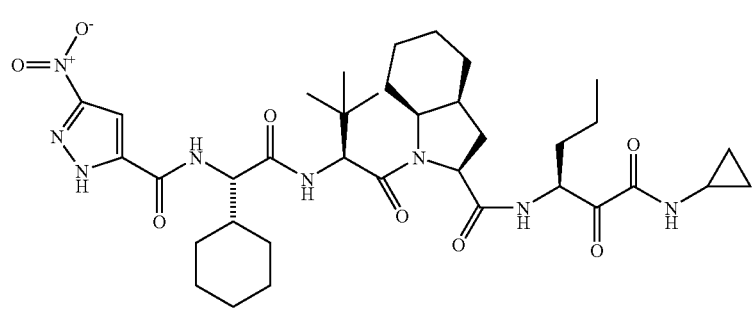
14a
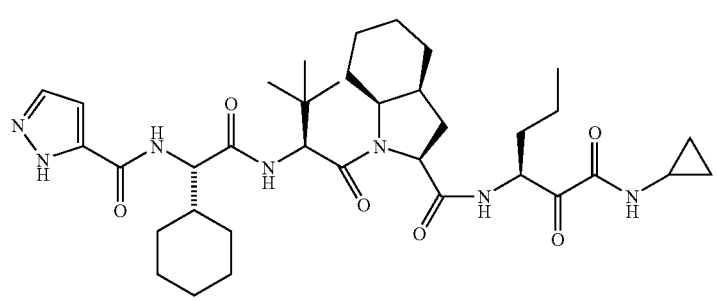
15a

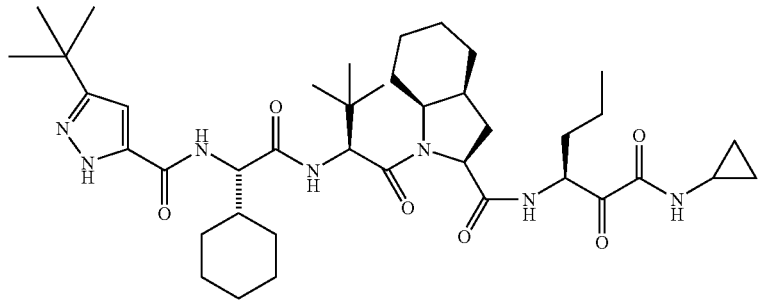
16a
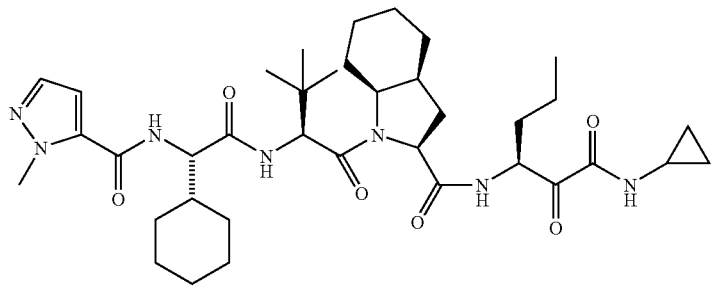
17a
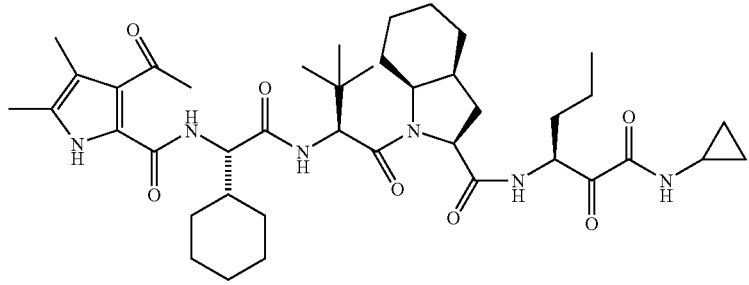
25a
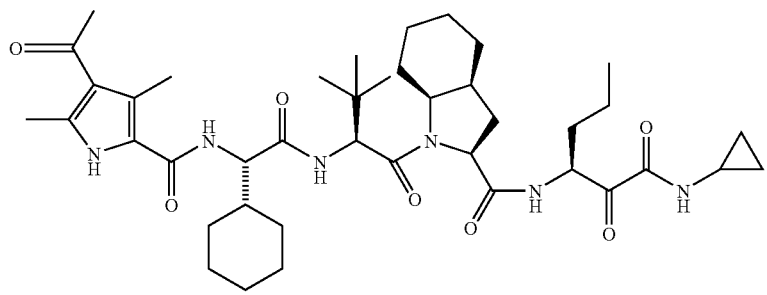
29a
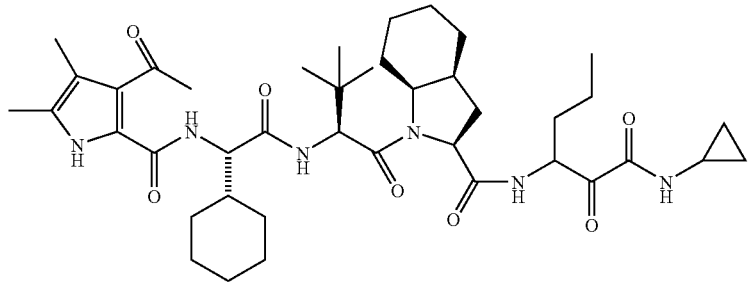
33a

-continued
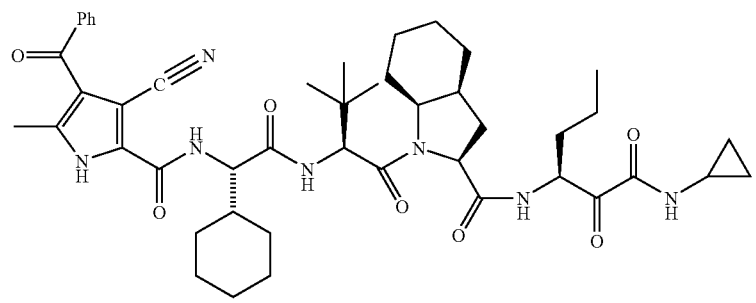
34a
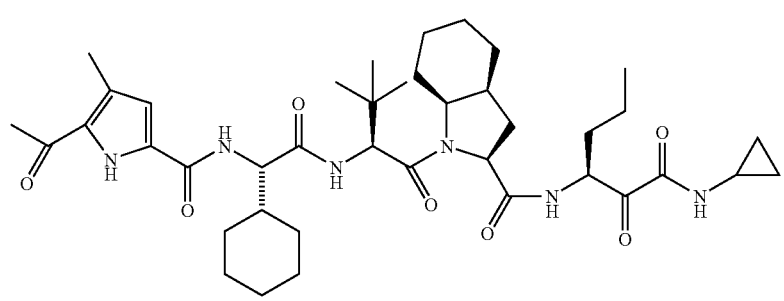
37a
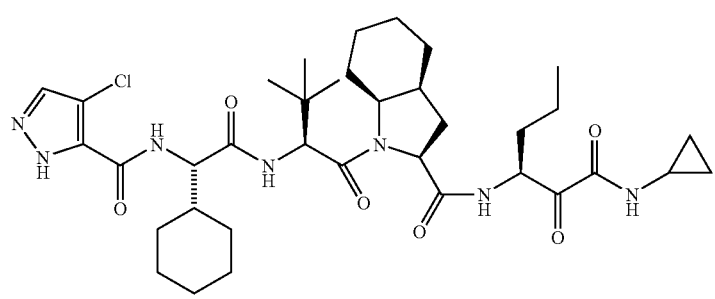
38a
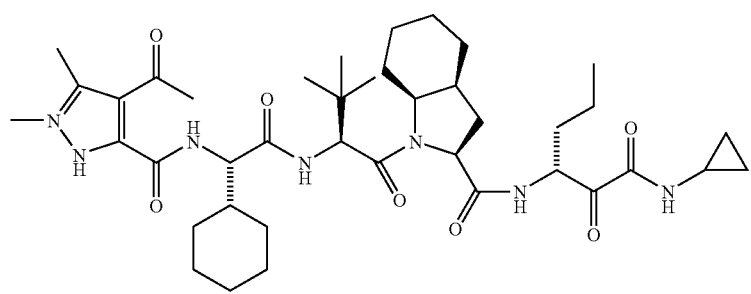
41a
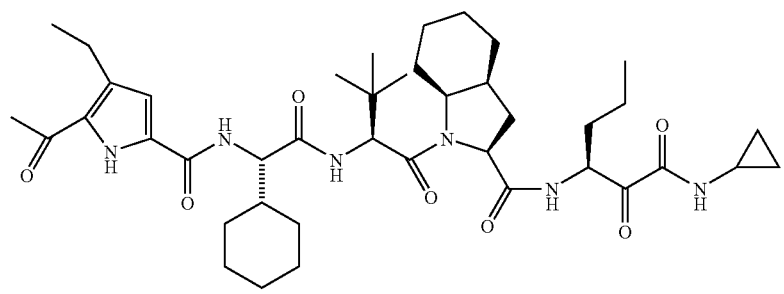
42a -continued
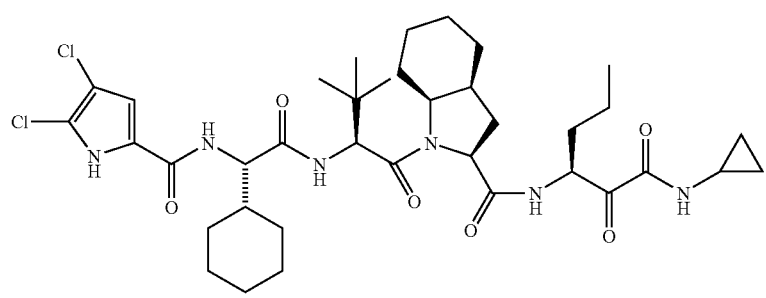
43a
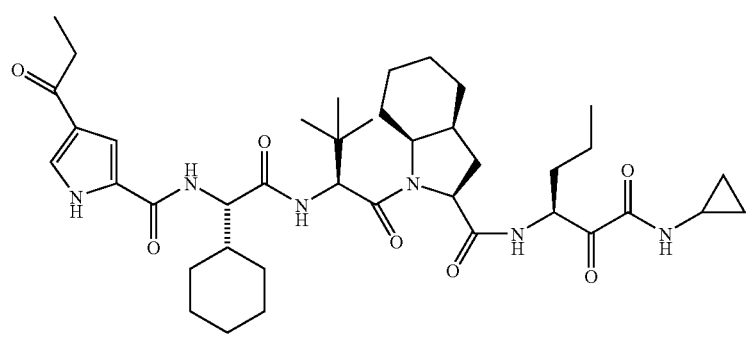
44a
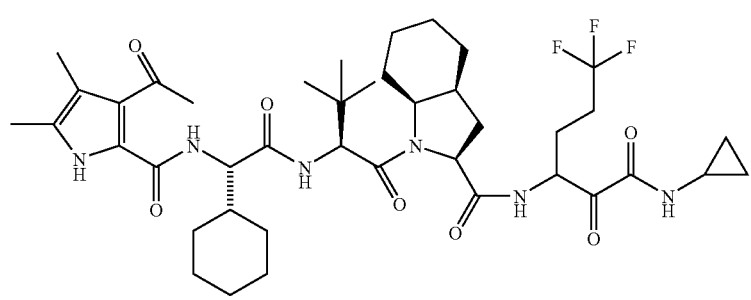
45a
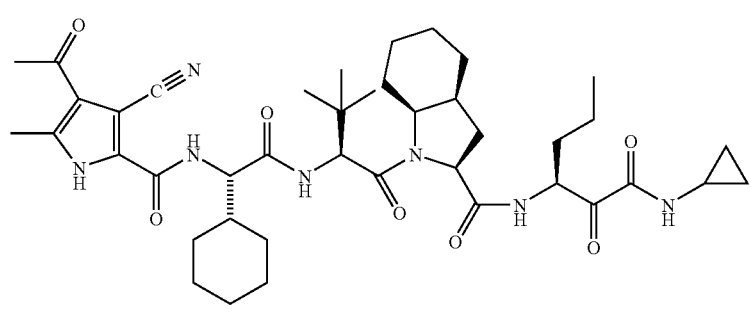
52a
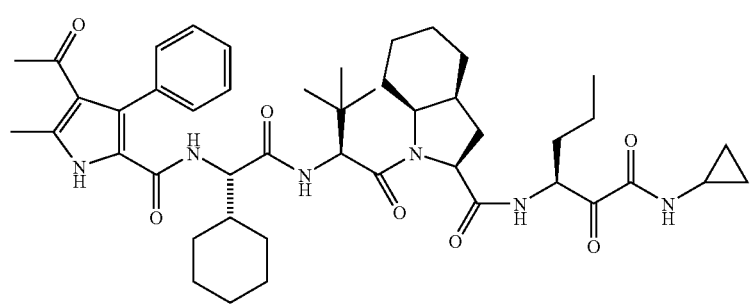
53a -continued
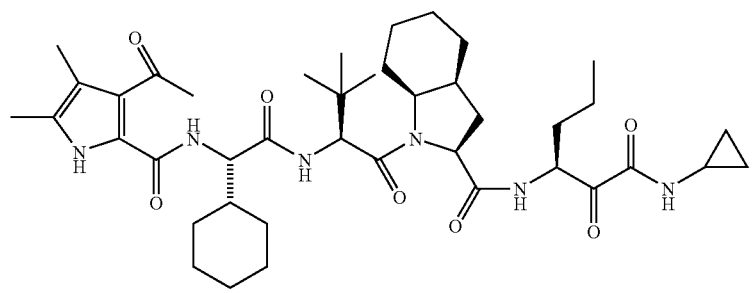
55a
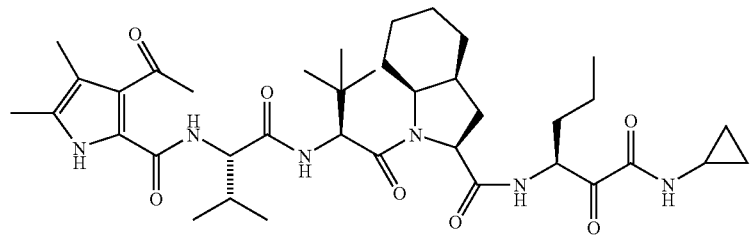
59a
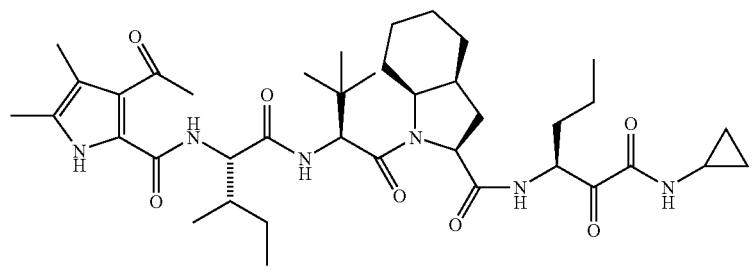
59a
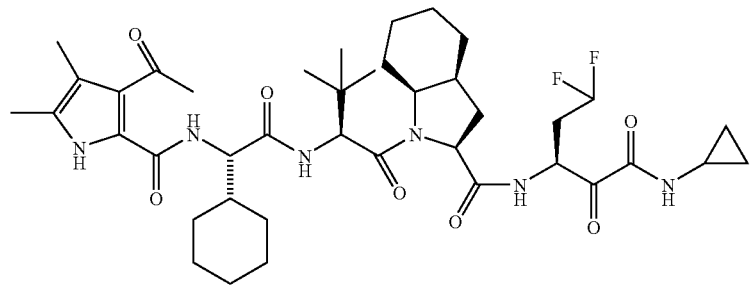
61a
or
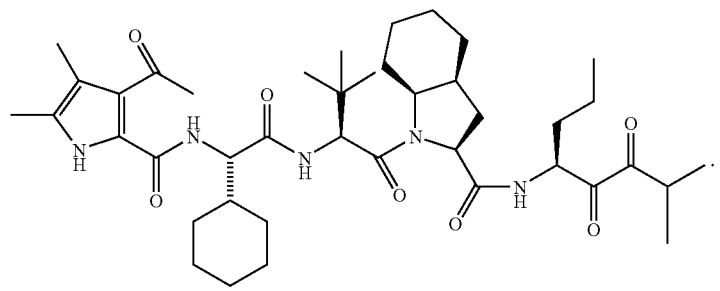
62a

23. The compound according to claim 1, wherein the compound is selected from:

25a

24. The compound according to claim 2, wherein T contains at least one hydrogen bond donor moiety selected from —NH$_2$, —NH—, —OH, and —SH.

25. The compound according to claim 24, wherein T is:

-continued wherein:
T is optionally substituted with up to 3 J substituents, wherein J is as defined in claim 2;
Z is independently O, S, NR$_{10}$, C(R$_{10}$)$_2$;
R$_{10}$ is:
  hydrogen,
  (C1–C12)-aliphatic-,
  (C6–C10)-aryl-,
  (C6–C10)-aryl-(C1–C12)aliphatic-,
  (C3–C10)-cycloalkyl or -cycloalkenyl-,
  [(C3–C10)-cycloalkyl or -cycloalkenyl]-(C1–C12)aliphatic-,
  (C3–C10)-heterocyclyl-,
  (C3–C10)-heterocyclyl-(C1–C12)-aliphatic-,
  (C5–C10)-heteroaryl-, or
  (C5–C10)-heteroaryl-(C1–C12)-aliphatic-;
n is 1; and
  ===== is independently a single bond or a double bond.

26. The compound according to claim 25, wherein T is:

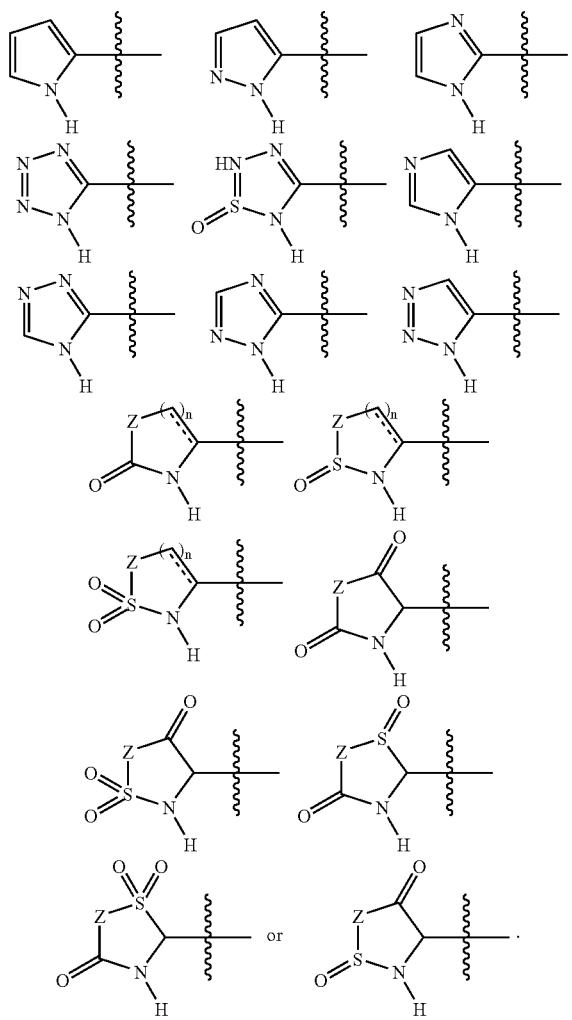

wherein:
T is optionally substituted with up to 4 J substituents, wherein J is as defined in claim 1;
Z is independently O, S, $NR_{10}$, $C(R_{10})_2$, SO, $SO_2$;
$R_{10}$ is:
  hydrogen,
  (C1–C12)-aliphatic-,
  (C6–C10)-aryl-,
  (C6–C10)-aryl-(C1–C12)aliphatic-,
  (C3–C10)-cycloalkyl or -cycloalkenyl-,
  [(C3–C10)-cycloalkyl or -cycloalkenyl]-(C1–C12)aliphatic-,
  (C3–C10)-heterocyclyl-,
  (C3–C10)-heterocyclyl-(C1–C12)-aliphatic-,
  (C5–C10)-heteroaryl-, or
  (C5–C10)-heteroaryl-(C1–C12)-aliphatic-;
n is 1; and
-----is independently a single bond or a double bond.

27. The compound according to claim 26, wherein T is:

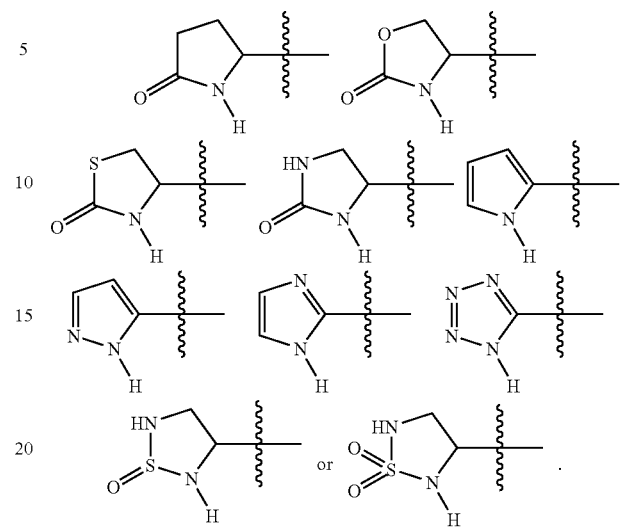

wherein:
T is optionally substituted with up to 4 J substituents, wherein J is as defined in claim 1.

28. The compound according to claim 27, wherein T is:

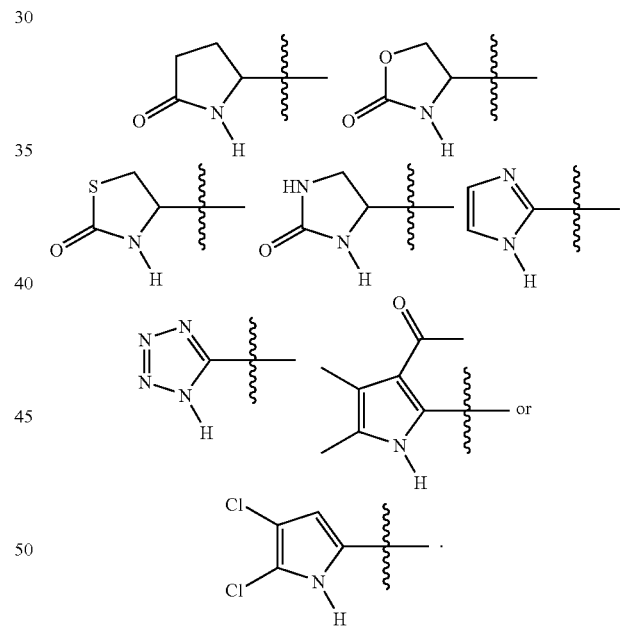

29. The compound according to claim 28, wherein T is:

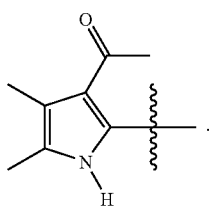

* * * * *